(12) United States Patent
Dhawan et al.

(10) Patent No.: US 10,995,323 B2
(45) Date of Patent: May 4, 2021

(54) TRANSAMINASE POLYPEPTIDES

(71) Applicant: Codexis Inc., Redwood City, CA (US)

(72) Inventors: Ish K. Dhawan, Foster City, CA (US); Gregory Miller, Redwood City, CA (US); Xiyun Zhang, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 16/717,596

(22) Filed: Dec. 17, 2019

(65) Prior Publication Data

US 2020/0109380 A1    Apr. 9, 2020

Related U.S. Application Data

(60) Continuation of application No. 16/399,488, filed on Apr. 30, 2019, now Pat. No. 10,550,370, which is a continuation of application No. 16/018,247, filed on Jun. 26, 2018, now Pat. No. 10,323,234, which is a continuation of application No. 15/912,892, filed on Mar. 6, 2018, now Pat. No. 10,323,233, which is a continuation of application No. 15/341,631, filed on Nov. 2, 2016, now Pat. No. 9,944,909, which is a division of application No. 14/684,916, filed on Apr. 13, 2015, now Pat. No. 9,512,410, which is a division of application No. 13/920,902, filed on Jun. 18, 2013, now Pat. No. 9,029,106, which is a continuation of application No. 12/684,864, filed on Jan. 8, 2010, now Pat. No. 8,470,564.

(60) Provisional application No. 61/143,401, filed on Jan. 8, 2009.

(51) Int. Cl.
 *C12N 9/10*    (2006.01)
 *C12P 13/00*   (2006.01)
 *C12P 41/00*   (2006.01)

(52) U.S. Cl.
 CPC .......... *C12N 9/1096* (2013.01); *C12P 13/001* (2013.01); *C12P 41/006* (2013.01); *C12Y 206/01* (2013.01); *C12Y 206/01018* (2013.01); *Y02P 20/52* (2015.11)

(58) Field of Classification Search
 None
 See application file for complete search history.

(56) References Cited

U.S. PATENT DOCUMENTS

| | | | |
|---|---|---|---|
| 4,518,692 A | 5/1985 | Rozzell | |
| 4,826,766 A | 5/1989 | Rozzell | |
| 4,950,606 A | 8/1990 | Stirling et al. | |
| 5,169,780 A | 12/1992 | Stirling et al. | |
| 5,300,437 A | 4/1994 | Stirling et al. | |
| 5,316,943 A | 5/1994 | Kidman et al. | |
| 5,346,828 A | 9/1994 | Stirling et al. | |
| 5,360,724 A | 11/1994 | Matcham et al. | |
| 5,814,473 A | 9/1998 | Patrick et al. | |
| 5,866,512 A | 2/1999 | Matcham et al. | |
| 5,965,432 A | 10/1999 | Kobayashi et al. | |
| 6,107,521 A | 8/2000 | Lin et al. | |
| 6,133,018 A | 10/2000 | Wu et al. | |
| 6,197,558 B1 | 3/2001 | Fotheringham | |
| 6,221,638 B1 | 4/2001 | Yamada et al. | |
| 6,344,351 B2 | 2/2002 | Yamada et al. | |
| 6,346,402 B1 | 2/2002 | Iwasaki et al. | |
| 6,413,752 B1 | 7/2002 | Takashima et al. | |
| 6,727,083 B2 | 4/2004 | Takashima et al. | |
| 7,169,592 B2 | 1/2007 | Yamada et al. | |
| 7,172,885 B2 | 2/2007 | Pannuri et al. | |
| 7,267,969 B2 | 9/2007 | Pannuri et al. | |
| 7,276,360 B2 | 10/2007 | Pannuri et al. | |
| 8,470,564 B2 | 6/2013 | Dhawan et al. | |
| 9,029,106 B2 | 5/2015 | Dhawan et al. | |
| 9,512,410 B2 | 12/2016 | Dhawan et al. | |
| 9,944,909 B2 | 4/2018 | Dhawan et al. | |
| 10,323,233 B2 | 6/2019 | Dhawan et al. | |
| 10,323,234 B2 | 6/2019 | Dhawan et al. | |
| 10,550,370 B2 * | 2/2020 | Dhawan | C12Y 206/01 |
| 2007/0259410 A1 | 11/2007 | Donaldson et al. | |
| 2008/0213845 A1 | 9/2008 | Fotheringham et al. | |
| 2009/0117627 A1 | 7/2009 | Doderer et al. | |
| 2014/0115737 A1 | 4/2014 | Abad | |
| 2016/0024540 A1 | 1/2016 | Debarge et al. | |

FOREIGN PATENT DOCUMENTS

| | | |
|---|---|---|
| EP | 1075534 A1 | 12/2001 |
| JP | 63273486 A | 11/1988 |
| KR | 2006007124 A | 1/2006 |
| WO | 99/46398 A1 | 9/1999 |

(Continued)

OTHER PUBLICATIONS

Cho, B.-K., et al., "Asymmetric Synthesis of L-Homophenylalanine by Equilibrium-Shift Using Recombinant Aromatic L-Amino Acid Transaminase", Biotechnology and Bioengineering, 83(2):226-234, 2003.

Cho, B.-K., et al., "Engineering Aromatic L-Amino Acid Transaminase for the Asymmetric Synthesis of Constrained Analogs of L-Phenylalanine", Biotechnology And Bioengineering, 94(5):842-850, 2006.

Cho, B.-K., et al., "Enzymatic Resolution for the Preparation of Enantiomerically Enriched D-β-Heterocyclic Alanine Derivatives Using *Escherichia coli* Aromatic L-Amino Acid Transaminase", Biotechnology and Bioengineering, 88 (4):512-519, 2004.

Cho, B.-K., et al., "Redesigning the Substrate Specificity of ω-Aminotransferase for the Kinetic Resolution of Aliphatic Chiral Amines", Biotechnology and Bioengineering, 99(2):275-284, 2008.

(Continued)

*Primary Examiner* — Hope A Robinson
(74) *Attorney, Agent, or Firm* — Codexis, Inc.

(57) ABSTRACT

The present disclosure provides engineered transaminase enzymes having improved properties as compared to a naturally occurring wild-type transaminase enzyme. Also provided are polynucleotides encoding the engineered transaminase enzymes, host cells capable of expressing the engineered transaminase enzymes, and methods of using the engineered transaminase enzymes to synthesize a variety of chiral compounds.

17 Claims, 1 Drawing Sheet
Specification includes a Sequence Listing.

(56) References Cited

FOREIGN PATENT DOCUMENTS

| WO | 00/23609 A1 | 4/2000 |
|---|---|---|
| WO | 00/66760 A1 | 11/2000 |
| WO | 2005/005633 A2 | 1/2005 |
| WO | 2006/063336 A2 | 6/2006 |
| WO | 2006/126498 A1 | 11/2006 |
| WO | 2007/093372 A1 | 8/2007 |
| WO | 2008/028654 A1 | 3/2008 |
| WO | 2008/127646 A2 | 10/2008 |
| WO | 2011/026556 A1 | 3/2011 |

OTHER PUBLICATIONS

Cho, B.-K., et al., "Simultaneous Synthesis of Enantiomerically Pure (S)-Amino Acids and (R)-Amines Using Coupled Transaminase Reactions", Biotechnology and Bioengineering, 81(7):783-789, 2003.
Christen, P., et al., "From Cofactor to Enzymes. The Molecular Evolution of Pyridoxal-5'-Phosphate-Dependent Enzymes", The Chemical Record, 1:436-447, 2001.
Crump, S.P. et al., "Biocatalytic Production of Amino Acids by Transamination", In Biocatalytic Production of Amino Acids and Derivatives; Rozzell, J. D., Wagner, F., Eds.; Wiley: New York, 1992; pp. 43-58.
C8 Eliot, A.C., et al., "The Dual-Specific Active Site of 7,8-Diaminopelargonic Acid Synthase and the Effect of the R391A Mutation", Biochemistry, 41:12582-12589, 2002.
Fadnavis, N.W., et al., "Asymmetric synthesis of nonproteinogenic amino acids with L-amino acid transaminase: synthesis of (2S)-2-amino-4-oxo-4-phenylbutyric and (3E,2S)-2-amino-4-phenylbutenoic acids", Tetrahedron: Asymmetry, 17:2199-2202, 2006.
Fernandez, F.J., et al., "Structural Studies of the Catalytic Reaction Pathway of a Hyperthermophilic Histidinol-phosphate Aminotransferase", The Journal of Biological Chemistry, 279(20):21478-21488, 2004.
Goto, M., et al., "Crystal Structures of Branched-Chain Amino Acid Aminotransferase Complexed with Glutamate and Glutarate: True Reaction Intermediate and Double Substrate Recognition of the Enzyme", Biochemistry, 42:3725-3733, 2003.
Haruyama, K, et al., "Structures of Escherichia coli Histidinol-Phosphate Aminotransferase and Its Complexes with Histidinol-Phosphate and N-(5'-Phosphopyridoxyl)-L-Glutamate: Double Substrate Recognition of the Enzyme", Biochemistry, 40:4633-4644, 2001.
Hirotsu, K., et al., "Dual Substrate Recognition of Aminotransferases", The Chemical Record, 5:160-172, 2005.
Höhne, M., et al., "Efficient Asymmetric Synthesis of Chiral Amines by Combining Transaminase and Pyruvate Decarboxylase", ChemBioChem, 9:363-365, 2008.
Hwang, B.-Y., et al., "High-throughput screening method for the identification of active and enantioselective ω-transaminases", Enzyme and Microbial Technology, 34:429-436, 2004.
Hwang, B.-Y., et al., "Revisit of aminotransferase in the genomic era and its application to biocatalysis", Journal of Molecular Catalysis B: Enzymatic, 37:47-55, 2005.
Hwang, J.-Y., et al., "Simultaneous Synthesis of 2-Phenylethanol and L-Homophenylalanine Using Aromatic Transaminase With Yeast Ehrlich Pathway", Biotechnology and Bioengineering, 102(5):1323-1329, 2009.
Käck, H., et al., "Crystal Structure of Diaminopelargonic Acid Synthase: Evolutionary Relationships between Pyridoxal-5'-phosphate-dependent Enzymes", J. Mol. Biol., 291:857-876, 1999.
Koszelewski, D., et al., "Asymmetric Synthesis of Optically Pure Pharmacologically Relevant Amines Employing ω-Transaminases", Adv. Synth. Catal., 350:2761-2766, 2008.
Koszelewski, D., et al., "Deracemisation of α-Chiral Primary Amines by a One-Pot, Two-Step Cascade Reaction Catalysed by ω-Transaminases", Eur. J. Org. Chem., pp. 2289-2292, 2009.
Koszelewski, D., et al., "Formal Asymmetric Biocatalytic Reductive Amination", Agnew. Chem. Int. Ed., 47:9337-9340, 2008.
Koszelewski, D., et al., "Synthesis of Optically Active Amines Employing Recombinant ω-Transaminases in E. coli Cells", ChemCatChem, 2: 73-77, 2010.
Liu, W., et al., "Crystal Structures of Unbound and Aminooxyacetate-Bound Escherichia coli γ-Aminobutyrate Aminotransferase", Biochemistry, 43:10896-10905, 2004.
Liu, W., et al., "Kinetic and Crystallographic Analysis of Active Site Mutants of Escherichia coli γ-Aminobutyrate Aminotransferase", 44:2982-2992, 2005.
Matsui, I., et al., "The Molecular Structure of Hyperthermostable Aromatic Aminotransferase with Novel Substrate Specificity from Pyrococcus horikoshii", The Journal of Biological Chemistry, 275(7): 4871-4879, 2000.
Mihara, H., et al., "N-Methyl-L-amino acid dehydrogenase from Pseudomonas putida. A novel member of an unusual NAD(P)-dependent oxidoreductase superfamily", FEBS Journal, 272:1117-1123, 2005.
Nobe, Y., et al., "The Novel Substrate Recognition Mechanism Utilized by Aspartate Aminotransferase of the Extreme Thermophile Thermus thermophilus HB8", The Journal of Biological Chemistry, 273(45):29554-29564, 1998.
Noland, B.W., et al., "Structural Studies of Salmonella typhimurium ArnB (PmrH) Aminotransferase: A 4-Amino-4-Deoxy-L-Arabinose Lipopolysaccharide-Modifying Enzyme", Structure, 10:1569-1580, 2002.
Okada, K., et al., "Structures of Escherichia coli Branched-Chain Amino Acid Aminotransferase and Its Complexes with 4-Methylvalerate and 2-Methylleucine: Induced Fit and Substrate Recognition of the Enzyme", Biochemistry, 40:7453-7463, 2001.
Okada, K., et al., "Three-Dimensional Structure of Escherichia coli Branched-Chain Amino Acid Aminotransferase at 2.5 Å Resolution", J. Biochem., 121:637-641, 1997.
Okamoto, A., et al., "Crystal Structures of Paracoccus denitrificans Aromatic Amino Acid Aminotransferase: A Substrate Recognition Site Constructed by Rearrangement of Hydrogen Bond Network", J. Mol. Biol., 280:443-461, 1998.
Okamoto, A., et al., "The Active Site of Paracoccus denitrificans Aromatic Amino Acid Aminotransferase Has Contrary Properties: Flexibility and Rigidity", Biochemistry, 38:1176-1184, 1999.
Oue, S., et al., "Paracoccus denitrificans Aromatic Amino Acid Aminotransferase: A Model Enzyme for the Study of Dual Substrate Recognition Mechanism", J. Biochem, 121:161-171, 1997.
Peisach, D., et al., "Crystallographic Study of Steps along the Reaction Pathway of D-Amino Acid Aminotransferase", Biochemistry, 37:4958-4967, 1998.
Sandmark, J., et al., "Conserved and Nonconserved Residues in the Substrate Binding Site of 7,8-Diaminopelargonic Acid Synthase from Escherichia coli Are Essential for Catalysis", Biochemistry, 43:1213-1222, 2004.
Sandmark, J., et al., "Structural Basis for the Inhibition of the Biosynthesis of Biotin by the Antibiotic Amiclenomycin", The Journal of Biological Chemistry, 277(45):43352-43358, 2002.
Shin J.-S., et al., "Purification, characterization, and molecular cloning of a novel amine:pyruvate transaminase from Vibrio fluvialis JS17", Appl. Microbiol. Biotechnol., 61:463-471, 2003.
Shin, J.-S., et al., "Asymmetric Synthesis of Chiral Amines With ω-Transaminase", Biotechnology and Bioengineering, 65(2):206-211, 1999.
Shin, J.-S., et al., "Exploring the Active Site of Amine: Pyruvate Aminotransferase on the Basis of the Substrate Structure-Reactivity Relationship: How the Enzyme Controls Substrate Specificity and Stereoselectivity", J. Org. Chem., 67:2848-2853, 2002.
Sivaraman, J., et al., "Crystal Structure of Histidinol Phosphate Aminotransferase (HisC) from Escherichia coli, and its Covalent Complex with Pyridoxal-5'-phosphate and L-Histidinol Phosphate", J. Mol. Biol., 311:761-776, 2001.
Sugio, S., et al., "Crystal structures of L201A mutant of D-amino acid aminotransferase at 2.0 Å resolution: implication of the structural role of Leu201 in transamination", Protein Engineering, 11(8):613-619, 1998.
Taylor, P.P., et al., "Novel biosynthetic approaches to the production of unnatural amino acids using transaminases", Tibtech, 16:412-418, 1998.

(56) References Cited

OTHER PUBLICATIONS

Truppo, M.D., et al., "Efficient kinetic resolution of racemic amines using a transaminase in combination with an amino acid oxidase", Chemical Communications, 2009, 2127-29.

Truppo, M.D., et al., "Efficient production of chiral amines at concentrations of 50g/L using transaminases", Organic Process Research & Development 14: 234-237, 2010.

Truppo, M.D., et al., "Rapid determination of both the activity and enantioselectivity of ketoreductases", Angew. Chem. Int. Ed. Engl., 47(14):2639-41, 2008.

Truppo, M.D., et al., "Rapid screening and scale-up of transaminase catalysed reactions," Organic & Biomolecular Chemistry, 7:395-398, 2009.

Ura, H., et al., "Substrate Recognition Mechanism of Thermophilic Dual-Substrate Enzyme", J. Biochem., 130:89-98, 2001.

Ura, H., et al., "Temperature Dependence of the Enzyme-Substrate Recognition Mechanism", J. Biochem., 129:173-178, 2001.

Van Ophem, P.W., et al., "Effects of the E177K Mutation in D-Amino Acid Transaminase. Studies on an Essential Coenzyme Anchoring Group That Contributes to Stereochemical Fidelity", Biochemistry, 38:1323-1331, 1999.

Yonaha, K., et al., "Properties of the Bound Coenzyme and Subunit Structure of ω-Amino Acid:Pyruvate Aminotransferase", The Journal of Biological Chemistry, 258(4):2660-2665, 1983.

Yun, H., et al., "Asymmetric synthesis of (S)-α-methylbenzylamine by recombinant *Escherichia coli* co-expressing omega-transaminase and acetolactate synthase", Biosci. Biotechnol. Biochem., 72(11):3030-3033, 2008.

Yun, H., et al., "Kinetic Resolution of (R,S)-sec-Butylamine Using Omega-Transaminase From Vibrio fluvialis JS17 Under Reduced Pressure", Biotechnology and Bioengineering, 87(6):772-778, 2004.

Yun, H., et al., "Synthesis of Enantiomerically Pure trans-(1R,2R)- and cis-(1S,2R)-1-Amino-2-Indanol by Lipase and ω-Transaminase", Biotechnology and Bioengineering, 93(2):391-395, 2006.

Yun, H., et al., "Use of Enrichment Culture for Directed Evolution of the Vibrio fluvialis JS17 ω-Transaminase, Which Is Resistant to Product Inhibition by Aliphatic Ketones", Applied and Environmental Microbiology, 71(8):4220-4224, 2005.

Yonaha, K. et al., "Monamine Transamination Catalyzed by omega-Amino Acid: Pyruvate Aminotransferase of *Pseudomonas* sp. F-126," Appl. Biol. Chem., 42(12)2363-2367, 1978.

Matcham, G.W. et al., "Biocatalysis for Chiral Intermediates: Meeting Commercial and Technical Challenges," CHIMICA OGGI/chemistry today, 1996.

Iwasaki, A., et al., "Microbial synthesis of chiral amines by (R)-specific transamination with *Arthrobacter* sp. KNK168", Applied Microbiology Biotechnology 69: 499-505, 2006.

Iwasaki, A., et al., "Microbial synthesis of (R)- and (S)-3,4-dimethoxyamphetamines through stereoselective transamination", Biotechnology Letters, 24: 1845-1846, 2003.

Genbank Accession No. ABA47738.1 GI7657826.3 dated Sep. 30, 2005.

Genbank Accession No. CAP44385.1 GI163262083 dated Dec. 18, 2007.

Genbank Accession No. YP002257813.1 GI207739420 dated Oct. 1, 2008.

Hwang, B.-Y., et al., "Identification of ω-Aminotransferase from Caulobacter crescentus and Site Directed Mutagenesis to Broader Substrate Specificity," J. Microbiol. Biotechnol. 18(1): 48-54, 2008.

Kaulmann, U. et al., "Substrate spectrum of ω-transaminase from Chromobacterium violaceum DSM30191 and its potential for biocatalysis," Enzyme Microbial Technol., 41:628-637, 2007.

Mehta P., et al., "Aminotransferases: demonstration of homology and division into evolutionary subgroups," Eur. J. Biochem., 214(2): 549-61, 1993.

Patel, R., et al., "Biocatalytic preparation of a chiral synthon for a vasopeptidase inhibitor: enzymatic conversion of N2-[(N-phenylmethoxy)carbonyl-L-homocysteinyl]-L-lysine(1-19)-disulfide to [4S-(4I,7I,10aJ)]1-octahydro-5-oxo-4-[phenylmethoxy)carbonyl]amino]-7H-pyrido-[2,1,-b][1,3]thiazepine-7-carboxylic acid methyl ester by a novel L-lysine e-aminotransferase," Enzyme and Microbial Technol. 27:376-89, 2000.

Sayer, C., et al., "Crystallization and preliminary X-ray diffraction analysis of ω-amino acid:pyruvate transaminase from Chromobacterium violaeceum," Acta Cryst. F63:117-19, 2007.

Shin, J.-S., et al., "Comparison of the ω-transaminases from Different Microorganisms and Application to Production of Chiral Amines," Biosci. Biotechnol. Biochem. 65:1782-88, 2001.

Yano, T., et al., "Directed evolution of an aspartate aminotransferase with new substrate specificities," Proc. Natl. Acad. Sci. USA, 95:5511-15, 1998.

Yi, S. -S., et al., "Covalent immobilization of ω-transaminase from Vibrio fluvialis JS17 on chitosan beads," Process Biochem., 42(5):895-98, 2007.

Yun, H., et al., "ω-Amino Acid:Pyruvate Transaminase from Alcaligenes denitrificans Y2k-2: a New Catalyst for Kinetic Resolution of β-Amino Acids and Amines," Appl. Environ. Microbiol., 70(4):2529-34, 2004.

Yonaha, K., et al., "Distribution of ω-Amino Acid: Pyruvate Transaminase and Aminobutyrate: α-Ketoglutarate Transaminase in Microorganisms," Agric. Biol. Chem., 47(10): 2257-65, 1983.

Truppo, M.D., "Rapid Screening and Process Development of Biocatalytic Reactions", Thesis submitted Univ. of Manchester, Faculty of Engineering and Physical Sciences, 1-296, 2009.

\* cited by examiner

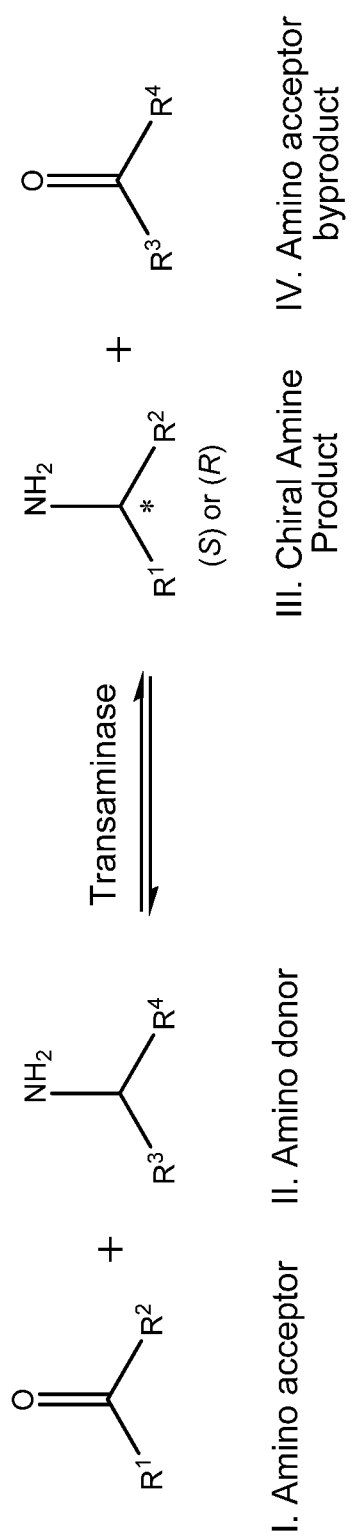

TRANSAMINASE POLYPEPTIDES

1. CROSS REFERENCE TO RELATED APPLICATIONS

This application is a Continuation of U.S. patent application Ser. No. 16/399,488, filed Apr. 30, 2019, now U.S. Pat. No. 10,550,370, which is a Continuation of U.S. patent application Ser. No. 16/018,247, filed Jun. 26, 2018, now U.S. Pat. No. 10,323,234, which is a Continuation of U.S. patent application Ser. No. 15/912,892, filed Mar. 6, 2018, now U.S. Pat. No. 10,323,233, which is a Continuation of U.S. patent application Ser. No. 15/341,631, filed Nov. 2, 2016, now U.S. Pat. No. 9,944,909, which is Divisional of U.S. patent application Ser. No. 14/684,916, filed Apr. 13, 2015, now U.S. Pat. No. 9,512,410, which claims priority to U.S. patent application Ser. No. 13/920,902, filed Jun. 18, 2013, now U.S. Pat. No. 9,029,106, which claims benefit under 35 U.S.C. § 120 of U.S. patent application Ser. No. 12/684,864, filed Jan. 8, 2010, now U.S. Pat. No. 8,470,564 on Jun. 25, 2013, and under 35 U.S.C. § 119(e) to U.S. Prov. Appln. Ser. No. 61/143,401, filed Jan. 8, 2009, the contents of each of which are incorporated herein by reference.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "376247-034.txt", a creation date of Jan. 8, 2010, and a size of 569 Kbytes. The Sequence Listing filed via EFS-Web is part of the specification and is incorporated in its entirety by reference herein.

3. BACKGROUND

Aminotransferases, also known as transaminases (E.C. 2.6.1) catalyze the transfer of an amino group, a pair of electrons, and a proton from a primary amine of an amino donor substrate to the carbonyl group of an amino acceptor molecule. Omega-transaminases (w-transaminases) transfer amine groups which are separated from a carboxyl group by at least one methylene insertion.

A general transaminase reaction is shown in Reaction I, below. In this reaction, an amino acceptor (I, keto, or ketone), which is the precursor of the desired amino acid product, is reacted with an amino donor (II). The transaminase enzyme exchanges the amino group of the amino donor with the keto group of the amino acceptor. The reaction therefore results in the desired chiral amine product (III) and a new amino acceptor (keto) compound (IV), which is a by-product.

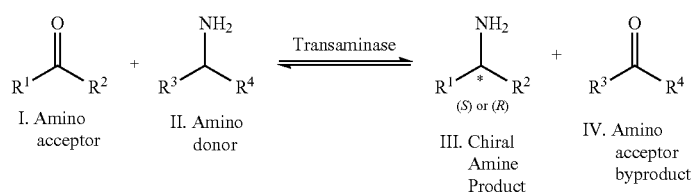

I. Amino acceptor
II. Amino donor
III. Chiral Amine Product
IV. Amino acceptor byproduct Various co-transaminases have been isolated from microorganisms, including, but not limited to, *Alcaligenes denitrificans, Bordetella bronchiseptica, Bordetella parapertussis, Brucella melitensis, Burkholderia malle, Burkholderia pseudomallei, Chromobacterium violaceum, Oceanicola granulosus* HTCC2516, *Oceanobacter* sp. RED65, *Oceanospirillum* sp. MED92, *Pseudomonas putida, Ralstonia solanacearum, Rhizobium meliloti, Rhizobium* sp. (strain NGR234), *Vibrio fluvialis, Bacillus thuringensis*, and *Klebsiella pneumoniae* (Shin et al., 2001, Biosci. Biotechnol, Biochem. 65:1782-1788).

Several aminotransferase gene and enzyme sequences have also been reported, e.g., *Ralstonia solanacearum* (Genbank Acc. No. YP_002257813.1, GI:207739420), *Burkholderia pseudomallei* 1710b (Genbank Acc. No. ABA47738.1, GI:76578263), and *Bordetella petrii* (Genbank Acc. No. AM902716.1, GI:163258032). Two transaminases, EC 2.6.1.18 and EC 2.6.1-19, have been crystallized and characterized (see Yonaha et al., 1983, Agric. Biol. Chem. 47 (10):2257-2265).

The enzyme ω-amino acid:pyruvate transaminase (ω-APT, E.C. 2.6.1.18) from *Vibrio fluvialis* JS17 carries out the following reaction

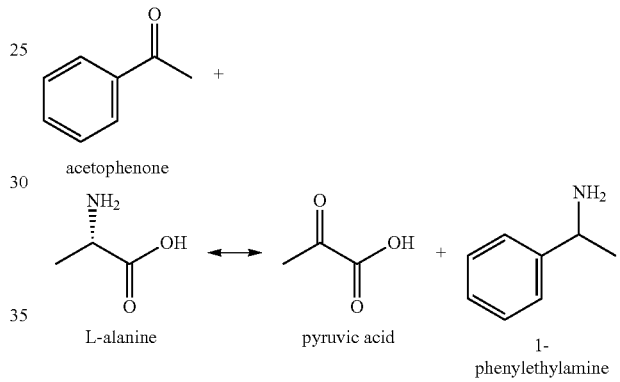

acetophenone
L-alanine
pyruvic acid
1-phenylethylamine using pyridoxal-5'-phosphate as a cofactor. The transaminase from *Vibrio fluvialis* has been reported to show catalytic activity toward aliphatic amines not bearing a carboxyl group.

Transaminase enzymes have potential industrial use for stereoselective synthesis of optically pure chiral amines and the enantiomeric enrichment of chiral amines and amino acids (Shin et al., 2001, Biosci. Biotechnol. Biochem. 65:1782-1788; Iwasaki et al., 2003, Biotech. Lett. 25:1843-1846; Iwasaki et al., 2004, Appl. Microb. Biotech. 69:499-505, Yun et al., 2004, Appl. Environ. Microbiol. 70:2529-2534; and Hwang et al., 2004, Enzyme Microbiol. Technol. 34:429-426). Chiral amines play an important role in the pharmaceutical, agrochemical and chemical industries and are frequently used as intermediates or synthons for the preparation of various pharmaceuticals, such as cephalosporine or pyrrolidine derivatives. Examples of the use of aminotransferases to generate useful chemical compounds include: preparation of intermediates and precursors of pregabalin (e.g., WO 2008/127646); the stereospecific synthesis and enantiomeric enrichment of β-amino acids (e.g., WO 2005/005633); the enantiomeric enrichment of amines (e.g., U.S. Pat. Nos. 4,950,606; 5,300,437; and 5,169,780); and the production of amino acids and derivatives (e.g., U.S. Pat. Nos. 5,316,943; 4,518,692; 4,826,766; 6,197,558; and 4,600,692).

In a great number of the various applications of chiral amines, only one particular optically active form, either the (R) or the (S) enantiomer is physiologically active. Hence, transaminases are useful for the enantiomeric enrichment and stereoselective synthesis of chiral amines.

However, transaminases used to mediate transamination reactions can have undesirable properties, such as instability and narrow substrate recognition profiles, thus making them undesirable for commercial applications. Thus, there is a need for other types of transaminases that can be used in processes for preparing chiral amines in an optically active form.

4. SUMMARY

The present disclosure provides transaminase polypeptides having the ability to catalyze the transfer of an amino group from a donor amine to an amine acceptor molecule, polynucleotides encoding such polypeptides, and methods for using the polypeptides. Generally, transaminase polypeptides are useful for the enantiomeric enrichment and stereoselective synthesis of chiral amines.

In one aspect, the transaminase polypeptides described herein have altered properties as compared to a reference enzyme, such as the naturally occurring transaminase obtained with *Vibrio fluvialis* (e.g., SEQ ID NO:2) or an engineered transaminase, such as the polypeptide of SEQ ID NO:18. Changes to enzyme properties can include, among others, improvements in enzymatic activity, stereoselectivity, sterospecificity, thermostability, solvent stability, and/or reduced substrate or product inhibition. In the embodiments herein, the altered properties are based on engineered transaminase polypeptides having residue differences at specific residue positions as compared to a reference sequence of a naturally occurring *Vibrio fluvialis* transaminase or a reference engineered transaminase, such as the sequence of SEQ ID NO:18. In some embodiments, the residue differences are present at one or more of the following residue positions: X4, X6, X9, X12, X21, X30, X31, X44, X45, X, 56, X57, X81, X82, X85, X86, X95, X112, X113, X127, X147, X153, X157, X166, X177, X181, X208, X211, X228, X233, X253, X272, X294, X297, X302, X311, X314, X316, X317, X318, X319, X320, X321, X324, X385, X391, X398, X407, X408, X409, X415, X417, X418, X420, X431, X434, X438, X444, and X446. Amino acid residues that can be present at the specified residue positions and the associated changes to enzyme properties are provided in the detailed description.

In some embodiments, the transaminase polypeptides of the disclosure are characterized by increased thermostability as compared to the wild-type polypeptide under the same reaction conditions. Thus, the polypeptides are capable of mediating transamination reactions (e.g., reaction schemes I, II or III), as indicated by the continued formation of products, at higher temperatures and for longer times than the wild-type polypeptide. In some embodiments, the transaminase polypeptides of the invention are improved in being able to retain activity under higher concentrations of the donor amine, such as 2 M concentration of isopropylamine. In some embodiments, the engineered transaminases with increased thermostability and/or increased isopropylamine stability comprises an amino acid sequence that is at least about 80%, 85%, 90%, 91%, 92%, 93%, 94%, 95%, 96%, 97%, 98%, 99% or more identical to the reference sequence of SEQ ID NO: 10, 16 or 18.

In some embodiments, the engineered transaminase polypeptide can have increased enzymatic activity as compared to the wild type transaminase enzyme or a reference engineered transaminase for transforming the substrates to the products. The amount of the improvement can range from more than 1.1 times (or fold) the enzymatic activity of the corresponding wild-type or reference transaminase enzyme, to as much as 2 times, 5 times, 10 times, 20 times, or more. In some embodiments, the engineered transaminase enzyme exhibits improved enzymatic activity that is at least 1.1-fold, 2-fold, 3-fold, 4-fold, 5-fold, 10-fold, 25-fold, 50-fold, 100-fold, 500-fold, or 1000-fold greater than that of the wild-type transaminase of SEQ ID NO:2 or a reference transaminase enzyme of SEQ ID NO:18. Improvements in enzyme activity may also have associated increases in stereoselectivity, stereospecificity, thermostability, solvent stability, and/or substrate binding, or reduced substrate and/or product inhibition.

In some embodiments, the engineered transaminases are characterized by activity on a variety of structurally different amine acceptor substrates. In some embodiments, the engineered transaminases are capable of stereoselectively converting substrates 3,4-dihydronaphthalen-1(2H)-one, 1-phenylbutan-2-one, 3,3-dimethylbutan-2-one, octan-2-one, 1-(4-bromophenyl)ethanone, 4-phenylbutan-2-one, ethyl 3-oxobutanoate, 1-(6-methoxynaphthalen-2-yl)ethanone, 1-(2,3-dihydrobenzo[b][1,4]dioxin-6-yl)ethanone, 1-(4-phenoxyphenyl)ethanone, (R)-4-oxotetrahydro-2H-pyran-3-yl benzoate and/or (R)-3-(benzyloxy)dihydro-2H-pyran-4(3H)-one to the corresponding amine product at a rate that is greater than the polypeptides of SEQ ID NO:2 and/or SEQ ID NO:18.

In some embodiments, the improved transaminase polypeptide comprises an amino acid sequence corresponding to SEQ ID NO: 4, 6, 8, 10, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198.

In some embodiments, the engineered transaminase enzymes described herein can be obtained by mutagenizing a gene encoding a naturally-occurring wild-type transaminase enzyme that is at least 80%, 81%, 82%, 83%, 84%, 85%, 86%, 87%, 88%, 89%, 90%, 91%, 92%, 93%, 94%, 95%, 96%, 97%, 98%, 99% or more identical to the amino acid sequence of *Vibrio fluvialis* transaminase (SEQ ID NO:2).

In another aspect, the present disclosure provides polynucleotides encoding the engineered transaminases described herein or polynucleotides that hybridize to such polynucleotides under highly stringent conditions. The polynucleotide can include promoters and other regulatory elements useful for expression of the encoded engineered transaminase, and can utilize codons optimized for specific desired expression systems.

In some embodiments, the polynucleotide encoding the improved transaminases comprises a sequence corresponding to SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, or 197.

In another aspect, the present disclosure provides host cells comprising the polynucleotides and/or expression vectors described herein. The host cells can be *Vibrio fluvialis* or they may be a different organism, such as *E. coli*. The host cells can be used for the expression and isolation of the engineered transaminase enzymes described herein, or, alternatively, they can be used directly for the conversion of the substrate to the stereoisomeric product.

In a further aspect, also provided are methods for carrying out reaction Schemes I, II or III (below) using any of the engineered transaminases described herein, which method comprises contacting or incubating the amino acceptor substrate with a transaminase polypeptide of the disclosure in presence of an amino donor under reaction conditions suitable for the conversion of the substrate to the amine product, thereby transforming the substrates to the product compounds. Whether carrying out the method with whole cells, cell extracts or purified transaminase enzymes, a single transaminase enzyme can be used or, alternatively, mixtures of two or more transaminase enzymes can be used.

5. BRIEF DESCRIPTION OF THE FIGURES

FIG. 1 illustrates the role of transaminases in the conversion of an amino acceptor (ketone) substrate of general formula I and an amino donor of general formula II to the chiral amine (III) product and an amino acceptor (ketone) byproduct (IV). This reaction uses a transaminase described herein and a co-factor such as pyridoxal-5'-phosphate.

6. DETAILED DESCRIPTION

6.1 Abbreviations

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

6.2 Definitions

As used herein, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Aminotransferase" and "transaminase" are used interchangeably herein to refer to a polypeptide having an enzymatic capability of transferring an amino group ($NH_2$), a pair of electrons, and a proton from a primary amine to a carbonyl group (C=O) of an acceptor molecule. More specifically, the transaminase polypeptides are capable of stereoselectively catalyzing the process of Scheme 1 (below). Transaminases as used herein include naturally occurring (wild type) transaminase as well as non-naturally occurring engineered polypeptides generated by human manipulation.

"Amino acceptor" and "amine acceptor", "keto substrate", "keto" and "ketone" are used interchangeably herein to refer to a carbonyl (keto, or ketone) compound which accepts an amino group from a donor amine. Amino acceptors are molecules of general Formula I,

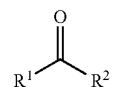

I in which each of $R^1$, $R^2$, when taken independently, is an alkyl, an alkylaryl group, or aryl group which is unsubstituted or substituted with one or more enzymatically acceptable groups. $R^1$ may be the same or different from $R^2$ in structure or chirality. $R^1$ and $R^2$, taken together, may form a ring that is unsubstituted, substituted, or fused to other rings. Amino acceptors include keto carboxylic acids and alkanones (ketones). Typical keto carboxylic acids are α-keto carboxylic acids such as glyoxalic acid, pyruvic acid, oxaloacetic acid, and the like, as well as salts of these acids. Amino acceptors also include substances which are converted to an amino acceptor by other enzymes or whole cell processes, such as fumaric acid (which can be converted to oxaloacetic acid), glucose (which can be converted to pyruvate), lactate, maleic acid, and others. Amino acceptors that can be used include, by way of example and not limitation, 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, 1-(4-bromophenyl)ethanone, 2-methyl-cyclohexamone, 7-methoxy-2-tetralone, 1-hydroxybutan-2-one, pyruvic acid, acetophenone, 2-methoxy-5-fluoroacetophenone, levulinic acid, 1-phenylpropan-1-one, 1-(4-bromophenyl)propan-1-one, 1-(4-nitrophenyl)propan-1-one, 1-phenylpropan-2-one, 2-oxo-3-methylbutanoic acid, 1-(3-trifluoromethylphenyl)propan-1-one, hydroxypropanone, methoxyoxypropanone, 1-phenylbutan-1-one, 1-(2,5-dimethoxy-4-methylphenyl)butan-2-one, 1-(4-hydroxyphenyl)butan-3-one, 2-acetylnaphthalene, phenylpyruvic acid, 2-ketoglutaric acid, and 2-ketosuccinic acid, including both (R) and (S) single isomers where possible.

"Amino donor" refers to an amino compound which donates an amino group to the amino acceptor, thereby becoming a carbonyl species. Amino donors are molecules of general Formula II,

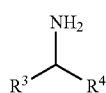

in which each of $R^3$, $R^4$, when taken independently, is an alkyl, an alkylaryl group, or aryl group which is unsubstituted or substituted with one or more enzymatically non-inhibiting groups. $R^3$ can be the same or different from $R^4$ in structure or chirality. $R^3$ and $R^4$, taken together, may form a ring that is unsubstituted, substituted, or fused to other rings. Typical amino donors that can be used with the invention include chiral and achiral amino acids, and chiral and achiral amines. Amino donors that can be used with the invention include, by way of example and not limitation, isopropylamine (also termed 2-aminopropane), α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, L-ornithine, β-alanine, taurine, n-octylamine, cyclohexylamine, 1,4-butanediamine, 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines.

"Chiral amine" refers to amines of general formula $R^1$—CH(NH$_2$)—$R^2$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^1$ and $R^2$ above) also can vary widely and include alkyl, aralkyl, aryl, halo, hydroxy, lower alkyl, lower alkoxy, lower alkylthio, cycloalkyl, carboxy, cabalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Pyridoxal-phosphate", "PLP", "pyridoxal-5'-phosphate", "PYP", and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7], Pyridoxal-5'-phosphate can be produced in vivo by phosphorylation and oxidation of pyridoxol (also known as Vitamin B$_6$). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces a chiral amine and regenerates the coenzyme. In some embodiments, the pyridoxal-5'-phosphate can be replaced by other members of the vitamin B$_6$ family, including pyridoxine (PN), pyridoxal (PL), pyridoxamine (PM), and their phosphorylated counterparts; pyridoxine phosphate (PNP), and pyridoxamine phosphate (PMP).

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity.

In some embodiments, a "reference sequence" can be based on a primary amino acid sequence, where the reference sequence is a sequence that can have one or more changes in the primary sequence. For instance, a "reference sequence based on SEQ ID NO:2 having at the residue corresponding to X85 an alanine or valine" refers to a reference sequence in which the corresponding residue at X85 in SEQ ID NO:2, which is a phenylalanine, has been changed to an alanine or valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diasteromers, commonly alternatively reported as the diastereomeric excess (d.e.). Enantiomeric excess and diastereomeric excess are types of stereomeric excess.

"Highly stereoselective" refers to a transaminase polypeptide that is capable of converting the substrate to the corresponding chiral amine product with at least about 85% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a transaminase polypeptide that exhibits an improvement in any enzyme property as compared to a reference transaminase. For the engineered transaminase polypeptides described herein, the comparison is generally made to the wild-type transaminase enzyme, although in some embodiments, the reference transaminase can be another improved engineered transaminase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), stereospecificity, and stereoselectivity (including enantioselectivity).

"Increased enzymatic activity" refers to an improved property of the engineered transaminase polypeptides, which can be represented by an increase in specific activity (e.g., product produced/time/weight protein) or an increase in percent conversion of the substrate to the product (e.g., percent conversion of starting amount of substrate to product in a specified time period using a specified amount of transaminase) as compared to the reference transaminase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 times the enzymatic activity of the corresponding wild-type transaminase enzyme, to as much as 2 times, 5 times, 10 times, 20 times, 25 times, 50 times, 75 times, 100 times, or more enzymatic activity than the naturally occurring transaminase or another engineered transaminase from which the transaminase polypeptides were derived. In specific embodiments, the engineered transaminase enzyme exhibits improved enzymatic activity in the range of 1.5 to 50 times, 1.5 to 100 times greater than that of the parent transaminase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}$ $s^{-1}$). Hence, any improvements in the enzyme activity of the transaminase will have an upper limit related to the diffusion rate of the substrates acted on by the transaminase enzyme. Transaminase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following o-phthaldialdehyde (OPA) derivitization. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a transaminase polypeptide can be expressed as "percent conversion" of the substrate to the product.

"Thermostable" refers to a transaminase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a transaminase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"pH stable" refers to a transaminase polypeptide that maintains similar activity (more than e.g., 60% to 80%) after exposure to high or low pH (e.g. 4.5-6 or 8 to 12) for a period of time (e.g. 0.5-24 hrs) compared to the untreated enzyme.

"Thermo- and solvent stable" refers to a transaminase polypeptide that is both thermostable and solvent stable.

"Derived from" as used herein in the context of engineered transaminase enzymes, identifies the originating transaminase enzyme, and/or the gene encoding such transaminase enzyme, upon which the engineering was based. For example, the engineered transaminase enzyme of SEQ ID NO:18 was obtained by artificially evolving, over multiple generations the gene encoding the *Vibrio fluvialis* transaminase enzyme of SEQ ID NO:2. Thus, this engineered transaminase enzyme is "derived from" the wild-type transaminase of SEQ ID NO:2.

"Hydrophilic Amino Acid or Residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained Amino Acid or Residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" represented by L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Amino acid difference" or "residue difference" refers to a change in the residue at a specified position of a polypeptide sequence when compared to a reference sequence. For example, a residue difference at position X9, where the reference sequence has an alanine, refers to a change of the residue at position X9 to any residue other than alanine. As disclosed herein, an enzyme can include one or more residue differences relative to a reference sequence, where multiple residue differences typically are indicated by a list of the specified positions where changes are made relative to the reference sequence.

"Conservative" amino acid substitutions or mutations refer to the interchangeability of residues having similar side chains, and thus typically involves substitution of the amino acid in the polypeptide with amino acids within the same or similar defined class of amino acids. However, in some embodiments, conservative mutations as used herein do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. The table below shows exemplary conservative substitutions.

| Residue | Possible Conservative Mutations |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the polypeptide of SEQ ID NO:2 or engineered transaminase of SEQ ID NO:10.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved transaminase enzymes may be present within a cell, present in the cellular medium, or prepared in various forms, such as lysates or isolated preparations. As such, in some embodiments, the improved transaminase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure transaminase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved transaminases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci USA 83:8893-8897; Freier et al., 1986, Proc. Natl. Acad. Sci USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered transaminase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the transaminases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Alkyl" by itself or as part of another substituent refers to a saturated or unsaturated branched, straight-chain or cyclic monovalent hydrocarbon radical having the stated number of carbon atoms (e.g., $C_1$-$C_6$ means one to six carbon atoms) that is derived by the removal of one hydrogen atom from a single carbon atom of a parent alkane, alkene or alkyne. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups composed of from 1 to 6 carbon atoms, preferably 1-4 carbon atoms.

"Alkanyl" by itself or as part of another substituent refers to a saturated branched, straight-chain or cyclic alkyl derived by the removal of one hydrogen atom from a single carbon atom of a parent alkane. Alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are ($C_1$-$C_6$) alkyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is ($C_2$-$C_6$) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, the alkynyl group is ($C_2$-$C_6$) alkynyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Aryl" by itself or as part of another substituent refers to a monovalent aromatic hydrocarbon group having the stated number of carbon atoms (e.g., $C_5$-$C_{15}$ means from 5 to 15 carbon atoms) derived by the removal of one hydrogen atom from a single carbon atom of a parent aromatic ring system. In some embodiments, the aryl group is ($C_5$-$C_{15}$) aryl, with ($C_5$-$C_{10}$) being even more preferred. In some embodiments, the aryls are cyclopentadienyl, phenyl and naphthyl.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. In some embodiments, the heteroaryl group is a 5-14 membered heteroaryl. In some embodiments, the heteroaryl group is a 5-10 membered heteroaryl.

"Alkoxy" by itself or as part of another substituent refers to —$OR^7$, where $R^7$ represents an alkyl or cycloalkyl group as defined herein. Typical alkoxy groups include, but are not limited to, methoxy, ethoxy, propoxy, butoxy, cyclohexyloxy, and the like.

"Alkylcarbonyl" by itself or as part of another substituent refers to —C(O)—$R^8$, where $R^8$ is an alkyl, as defined above. Typical alkoxycarbonyl include, but are not limited to, acetyl, ethylcarbonyl, n-propylcarbonyl, and the like.

"Alkoxycarbonyl" by itself or as part of another substituent, refers to C(O)$OR^9$ where $R^9$ represents an alkyl or cyclalkyl group as defined herein. Typical alkoxycarbonyl groups include, but are not limited to, methoxycarbonyl, ethoxycarbonyl, proproxycarbonyl, butoxycarbonyl, cyclohexyloxycarbonyl, and the like.

"Amino" by itself or as part of another substituent refers to the group —$NH_2$. Substituted amino refers to the group —$NHR^{10}$, $NR^{10}R^{10}$, and $NR^{10}R^{10}R^{10}$, where each $R^{10}$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylamino, triethylamino, methylsulfonylamino, furanyl-oxy-sulfamino, and the like.

"Substituted alkyl, aryl, arylalkyl, heteroaryl or heteroarylalkyl" refers to an alkyl, aryl, arylalkyl, heteroaryl or heteroarylakyl group in which one or more hydrogen atoms is replaced with another substituent group. Exemplary substituent groups include, but are not limited to, —$OR^{11}$, —$SR^{11}$, —$NR^{11}R^{11}$, —$NO_2$, —NO, —CN, —$CF_3$, halogen (e.g., —F, —Cl, —Br and —I), —C(O)$R^{11}$, —C(O)$OR^{11}$, —C(O)$NR^{11}$, —S(O)$_2R^{11}$, —S(O)$_2NR^{11}R^{11}$, where each $R^{10}$ is independently selected from the group consisting of hydrogen and ($C_1$-$C_6$) alkyl.

"Substituted" as used herein means one or more hydrogen atoms (e.g., 1, 2, 3, 4, 5, or 6 hydrogen atoms) of the group is replaced with a substituent atom or group commonly used in pharmaceutical chemistry. Each substituent can be the same or different. Examples of suitable substituents include, but are not limited to, alkyl, alkenyl, alkynyl, cycloalkyl, aryl, aralkyl, cycloheteroalkyl, heteroaryl, $OR^{12}$ (e.g., hydroxyl, alkoxy (e.g., methoxy, ethoxy, and propoxy), aryloxy, heteroaryloxy, aralkyloxy, ether, ester, carbamate, etc.), hydroxyalkyl, alkoxycarbonyl, alkoxyalkoxy, perhaloalkyl, perfluoroalkyl (e.g., $CF_3$, $CF_2$, $CF_3$), perfluoroalkoxy (e.g., $OCF_3$, $OCF_2CF_3$), alkoxyalkyl, $SR^{12}$ (e.g., thiol, alkylthio, arylthio, heteroarylthio, aralkylthio, etc.), $S^+R^{11}{}_2$, S(O)$R^{12}$, $SO_2R^{12}$, $NR^{12}R^{12}$ (e.g., primary amine (i.e., $NH_2$), secondary amine, tertiary amine, amide, carbamate, urea, etc.), hydrazide, halide, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. In embodiments in which a functional group with an aromatic carbon ring is substituted, such substitutions will typically number about 1 to 5, with about 1 or 2 substitutions being preferred.

6.3 Transaminase Enzymes

The present disclosure provides transaminase polypeptides having the ability to catalyze the transfer of an amino group from a donor amine to an amine acceptor molecule, polynucleotides encoding such polypeptides, and methods for using the polypeptides. Transaminase polypeptides are useful for the enantiomeric enrichment and stereoselective synthesis of chiral amines.

The transaminase enzymes described herein are capable of catalyzing the transfer of an amino group from an amino donor of general Formula II to an amino acceptor (ketone substrate) of general Formula I. The products of this reaction are a chiral amine (III) having a stereogenic carbon atom indicated by the * and an amino acceptor (ketone) byproduct (IV), as shown in Scheme 1:

Scheme 1

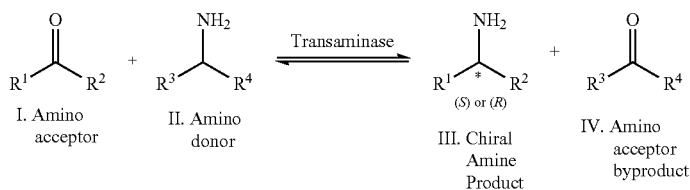

I. Amino acceptor
II. Amino donor
III. Chiral Amine Product
IV. Amino acceptor byproduct where the chiral carbon to which the amine is bonded has is predominantly (S) or (R) stereochemistry. As such, the chiral amine product is produced in stereomeric excess.

In some embodiments, the transaminase enzymes described herein are capable of catalyzing the transfer of an amino group from an amino donor of general Formula II to an amino acceptor (ketone substrate) of general Formula I and stereoselectively forming a chiral amine ($III_S$) in which the chiral carbon to which the amine is bonded has predominately (S) stereochemistry, and an amino acceptor (ketone) byproduct (IV), as shown in Scheme 2:

Scheme 2

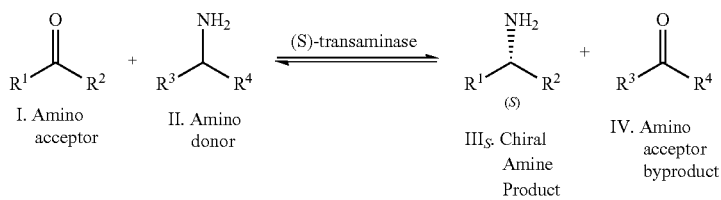

I. Amino acceptor
II. Amino donor
$III_S$. Chiral Amine Product
IV. Amino acceptor byproduct In some embodiments, the transaminase enzymes described herein are capable of catalyzing the transfer of an amino group from an amino donor of general Formula II to an amino acceptor (ketone) of general Formula I, in which the products of the reaction are a chiral amine ($III_R$) having predominately (R) stereochemistry, and an amino acceptor (ketone) byproduct (IV), as shown in Scheme 3:

Scheme 3

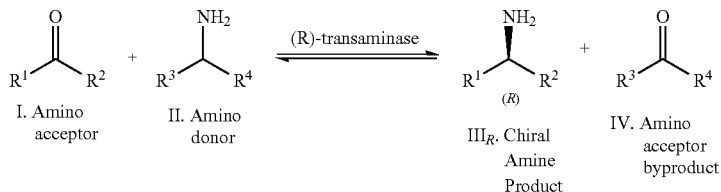

I. Amino acceptor
II. Amino donor
$III_R$. Chiral Amine Product
IV. Amino acceptor byproduct Each of $R^1$, $R^2$, $R^3$ and $R^4$, when taken independently, can be an alkyl, an alkylaryl group, or aryl group which is unsubstituted or substituted with one or more enzymatically non-inhibiting groups, where $R^1$ is different from $R^2$ in structure or chirality, or $R^1$ and $R^2$, taken together, are a hydrocarbon chain of 4 or more carbon atoms containing a center of chirality. In some embodiments, the alkyl group can be a substituted or unsubstituted branched or straight chain alkyl. $R_3$ may be the same or different from $R^4$ in structure or chirality. In some embodiments, $R^3$ and $R^4$, taken together, may form a ring that is unsubstituted, substituted, or fused to other rings. In some embodiments, the rings can be substituted or unsubstituted cycloalkyl or heterocycloalkyl. In some embodiments for $R^3$ and $R^4$, the alkyl, either alone or as a substituted or unsubstituted alkylaryl is a lower alkyl.

In general, the enzymatic process operates on only one chiral form of an amine, or operates on one chiral form to a far greater extent than the other. Thus, the transaminase polypeptides described herein are capable of performing stereoselective synthesis, in which one of the chiral amine products ($III_S$ or $III_R$) illustrated above is produced in an amount substantially greater than the other. "Substantially greater" as used herein refers to a percentage of the combined amount of both chiral forms that is at least about 51% (e.g., at least 51, 55, 60, 65, 70, 75, 80, 85, 90, 91, 92, 93, 94, 95, 96, 97, 98, or 99%). As such, in some embodiments, the product of the transaminase can be in a stereomeric excess of at least 5%, 10%, 20%, 30%, 40%, 50%, 60%, 70%, 80%, 90% 95%, 96%, 97%, 98%, or 99% or greater.

Reactions shown in Schemes 1 to 3 use an amino acceptor substrate and an amino donor substrate. Amino acceptors are compounds of general Formula I:

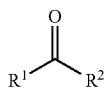

$$\text{I}$$

in which each of $R^1$, $R^2$, when taken independently, can be an alkyl, an alkylaryl group, or aryl group which is unsubstituted or substituted with one or more enzymatically non-inhibiting groups. As noted above, $R^1$ may be the same or different from $R^2$ in structure or chirality. In some embodiments, $R^1$ and $R^2$, taken together, may form a ring that is unsubstituted, substituted, or fused to other rings. In some embodiments, the amino acceptor is any compound according to Formula 1, above.

Amino donors are compounds of general Formula II:

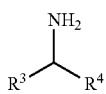

$$\text{II}$$

in which each of $R^3$, $R^4$, when taken independently, is an alkyl, an alkylaryl group, or aryl group which is unsubstituted or substituted with one or more enzymatically non-inhibiting groups. $R_3$ may be the same or different from $R_4$ in structure or chirality. $R^3$ and $R^4$, taken together, may form a ring that is unsubstituted, substituted, or fused to other rings. In some embodiments for $R^3$ and $R^4$, the alkyl, either alone or as a substituted or unsubstituted alkylaryl is a lower alkyl. The amino donors can include all salt forms of the compounds of Formula II.

In some embodiments, the amino donor is any compound according to Formula II, above and all possible salt forms. Exemplary amino donors include, among others, isopropylamine (2-amino propane), D-alanine, L-alanine, or D,L-alanine, and all possible salts of these amino donors.

As illustrated, the reaction can proceed in either the forward or reverse direction. In some embodiments, either the forward or reverse reactions can be favored by adding or removing starting materials or reaction products. For example, when one stereoselectively synthesizes one chiral form of an amine ($III_S$ or $III_R$), as shown in Reactions I and II, additional amino acceptor (ketone) or amino donor can be added (up to saturation) and/or the chiral amine or ketone by product formed can be removed.

For performing the transamination reactions, the present disclosure provides engineered transaminase enzymes that are capable of stereoselectively converting an amino acceptor to the corresponding chiral amino product and which have an improved property when compared with the naturally-occurring enzyme obtained from *Vibrio fluvialis* (SEQ ID NO:2) or when compared with other engineered transaminase enzymes (e.g., SEQ ID NO:18).

In the characterizations of the transaminases herein, the polypeptides can be described in reference to the amino acid sequence of a naturally occurring transaminase of *Vibrio fluvialis* or another engineered transaminase. As such, the amino acid residue position is determined in the transaminases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. A substitution mutation, which is a replacement of an amino acid residue in a reference sequence with a different amino acid residue may be denoted by the symbol "→", or by conventional notations used in the art, for example, Y(number)Z, where Y is the amino acid residue in the reference sequence, the "number" refers to the residue position, and Z is the amino residue substitution.

The polynucleotide sequence encoding the naturally occurring transaminase of *Vibrio fluvialis* JS17 is described in Shin et al., 2003, "Purification, characterization, and molecular cloning of a novel amine:pyruvate transaminase from *Vibrio fluvialis* JS17" Appl Microbiol Biotechnol. 61(5-6):463-471). The polynucleotide and amino acid sequence of the *Vibrio fluvialis* transaminase is also presented herein as SEQ ID NO:1 and SEQ ID NO:2, respectively.

As noted above, the transaminases of the disclosure are characterized by an improved enzyme property as compared to the naturally occurring parent enzyme or another engineered transaminase polypeptide. In the embodiments herein, the improved property of the transaminase can be with respect to, among others, enzyme activity, stability (e.g., solvent- and/or thermostability), stereoselectivity, stereospecificity, inhibitor resistance, and substrate recognition. In some embodiments, the transaminase polypeptides can have more than one improved property, such as increased stability and substrate recognition.

In some embodiments, the engineered transaminases have various residue differences as compared to a reference sequence (e.g., naturally-occurring polypeptide of SEQ ID NO:2 or an engineered polypeptide of SEQ ID NO:18) that result in changes to the enzyme properties. The residue differences can be characterized as "modifications" of the reference sequence, where the modifications include amino acid substitutions, deletions, and insertions. Any one or a combination of modifications can be present to generate the improved engineered transaminases. These residue differences can also be described as particular features of the improved engineered polypeptides at specified residue positions.

In some embodiments, the number of residue differences from the reference transaminase polypeptide that provides an improved transaminase property can comprise differences at one or more residue positions, 2 or more residue positions, 3 or more residue positions, 5 or more residue positions, 10 or more residue positions, or 20 or more residue positions, up to 10% of the total number of amino acids, up to 20% of the total number of amino acids, or up to 30% of the total number of amino acids of the reference enzyme sequence. In some embodiments, the number of residue differences as compared to the reference sequence can be about 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue positions. In some embodiments, the number of differences as compared to the reference sequence can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue positions.

In some embodiments, the residue differences comprise substitutions as compared to the reference sequence. In some embodiments, the substitutions as compared to the reference sequence can be at one or more residue positions, 2 or more residue positions, 3 or more residue positions, 5 or more residue positions, 10 or more residue positions, or 20 or more residue positions, up to 10% of the total number of amino acids, up to 20% of the total number of amino acids, or up to 30% of the total number of amino acids of the reference enzyme sequence. In some embodiments, the number of substitutions as compared to the reference sequence can be substitutions about 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue positions. In some embodiments, the number of substitutions as compared to the reference sequence can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue positions.

In some embodiments, the residue differences of the engineered transaminases of the disclosure can occur at one or more of the following residue positions: X4, X9, X12, X21, X30, X31, X44, X45, X, 56, X57, X81, X82, X85, X86, X95, X112, X113, X127, X147, X153, X157, X166, X177, X181, X208, X211, X228, X233, X253, X272, X294, X297, X302, X311, X314, X316, X317, X318, X319, X320, X321, X324, X385, X391, X398, X407, X408, X409, X415, X417, X418, X420, X431, X434, X438, X444, and X446. As described herein, the presence of particular amino acid residues at these residue positions is associated with changes to properties of the transaminases. In some embodiments, the number of residue differences can be at least 2, 3, 4, 5, or 6 or more of the specified residue positions.

In some embodiments, the choice of amino acid residues for the specified residue positions can be based on the following features. X4 is a basic residue; X9 is a polar residue; X12 a non-polar residue; X21 is a polar residue; X30 is an aliphatic or non-polar residue; X31 is an aliphatic or non-polar residue; X44 is an aliphatic or non-polar residue; X45 is a constrained residue; X56 is a non-polar or aliphatic residue; X57 is an aromatic, aliphatic, non-polar, polar or cysteine residue; X81 is an acidic residue; X82 is an aromatic or constrained residue; X85 is an aliphatic, non-polar, polar, or cysteine residue; X86 is a constrained, aromatic, or polar residue; X95 is a polar residue; X112 is a non-polar or aliphatic residue; X113 is a cysteine, aromatic or constrained residue; X127 is an aliphatic or non-polar residue; X147 is a non-polar residue; X153 is an aliphatic, non-polar, or polar residue; X157 is a polar residue; X166 is a polar residue; X177 is a non-polar or aliphatic residue; X181 is a basic residue; X208 is a non-polar or aliphatic residue; X211 is an acidic residue; X228 is a non-polar residue; X233 is a polar or aliphatic residue; X253 is a non-polar residue; X272 is a non-polar or aliphatic residue; X294 is a non-polar or aliphatic residue; X297 is an aliphatic residue; X302 is an acidic residue; X311 is an aliphatic residue; X314 is an aliphatic or polar residue; X316 is an acidic residue; X317 is an aromatic, non-polar or aliphatic residue; X318 is an aromatic, basic or non-polar residue; X319 is a non-polar, aliphatic, or polar residue; X320 is an aliphatic residue; X321 is an aliphatic residue; X324 is a non-polar residue; X385 is a basic residue; X398 is a basic residue; X407 is a polar residue; X408 is an aliphatic residue; X409 is non-polar residue; X415 is a non-polar residue; X417 is a non-polar, aliphatic, polar, acidic, or cysteine residue; X418 is a non-polar or aliphatic residue; X420 is a polar residue; X431 is an acidic residue; X434 is an aliphatic residue; X438 is an aliphatic residue; X444 is a non-polar or aliphatic residue; and X446 is a non-polar or aliphatic residue. In some embodiments, where the amino acid residue at the corresponding residue position of the reference sequence are encompassed within the category of amino acids described for the specified position, a different amino acid within that amino acid category can be used in light of the guidance provided herein.

In some embodiments, the transaminase polypeptides can have additionally one or more residue differences at residue positions not specified by an X above as compared to a reference sequence, for example SEQ ID NO:2. In some embodiments, the differences can be 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue differences at other amino acid residue positions not defined by X above. In some embodiments, the number of differences can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue differences at other amino acid residue positions. In some embodiments, the differences comprise conservative mutations.

In some embodiments, the amino acid residues at the specified positions can be selected from one or more of the following features: X4 is R; X9 is T; X12 is G; X21 is N; X30 is A; X31 is A; X44 is A; X45 is H; X56 is V; X57 is L, I, F, A, S, or C; X81 is D; X82 is H; X85 is A, S, V, T, N, or C; X86 is S, H, N, F, G, or A; X95 is T; X112 is I; X113 is H or C; X127 is L; X147 is G; X153 is A, S T, N, G, Q, or C; X157 is T; X166 is S; X177 is L; X181 is R; X208 is I; X211 is K; X228 is G; X233 is T, S or L; X253 is M; X272 is A; X294 is V; X297 is A; X302 is K; X311 is V; X314 is V or T; X316 is K; X317 is L, Y or M; X318 is G, R, or F; X319 is V or Q; X320 is A; X321 is L; X324 is G; X385 is R; X391 is A; X398 is R; X407 is S; X408 is A; X409 is G; X415 is M; X417 is F, A, I, C, T, S, or C; X418 is V; X420 is N; X431 is D; X434 is V; X438 is L; X444 is V; and X446 is V. In some embodiments, the transaminase polypeptides can have additionally one or more residue differences at residue positions not specified by an X above as compared to a reference sequence, for example SEQ ID NO:2. In some embodiments, the differences can be 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue differences at other amino acid residue positions not defined by X above. In some embodiments, the number of differences can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue differences at other amino acid residue positions. In some embodiments, the differences comprise conservative mutations. In some embodiments, the engineered transaminases can comprise an amino acid sequence that is at least 80%, 85%, 86%, 87%, 88%, 89%, 90%, 91%, 92%, 93%, 94%, 95%, 96%, 97%, 98%, 99%, or more identical to a reference based on SEQ ID NO:2 having one or more of the preceding features, and is characterized one or more of the improved enzyme properties described herein.

In some embodiments, the improved transaminase polypeptides comprise an amino acid sequence having at least one or more residue differences as compared to the reference sequence, e.g., naturally occurring sequence of SEQ ID NO:2 or an engineered transaminase sequence of SEQ ID NO:18, at the following residue positions: X57, X85, X86, X153, X228, X233, X317, X318, and X417. In some embodiments, the residues at these residue positions can be selected from the following features: X57 is an aromatic, aliphatic, non-polar, polar or cysteine residue; X85 is an aliphatic, non-polar, polar, or cysteine residue; X86 is a constrained, aromatic, or polar residue; X153 is an aliphatic, non-polar, or polar residue; X228 is a non-polar residue; X233 is a polar or aliphatic residue; X317 is an aromatic, non-polar or aliphatic residue; X318 is an aromatic, basic or non-polar residue; and X417 is a non-polar, aliphatic, polar, acidic, or cysteine residue. In some embodiments, the residues at these residue positions can be selected from the following features: X57 is L, I, F, A, S, or C; X85 is A, S, V, T, N, or C; X86 is S, H, N, F, G, or A; X153 is A, S T, N, G, Q, or C; X228 is G; X233 is T, S or L; X317 is L, Y or M; X318 is G, R, or F; and X417 is F, A, I, C, T, S, or C. In some embodiments, the engineered transaminases can comprise an amino acid sequence that is at least 80%, 85%, 86%, 87%, 88%, 89%, 90%, 91%, 92%, 93%, 94%, 95%, 96%, 97%, 98%, 99%, or more identical to a reference based on SEQ ID NO:2 having one or more of the preceding features, and is characterized one or more of the improved enzyme properties described herein.

In some embodiments, the improved transaminase polypeptide can comprise an amino acid sequence that is at least 80%, 85%, 86%, 87%, 88%, 89%, 90%, 91%, 92%, 93%, 94%, 95%, 96%, 97%, 98%, 99%, or more identical to a sequence corresponding to SEQ ID NO: 4, 6, 8, 10, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198. In some of these embodiments, the transaminase polypeptides can have one or more of the improved properties described herein.

In some embodiments, the improved transaminase polypeptides comprises an amino acid sequence corresponding to the sequence of SEQ ID NO: 4, 6, 8, 10, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198.

In some embodiments, the improved property of the transaminase polypeptide is with respect to its stability, such as thermostability and/or solvent stability. It is advantageous for transaminase polypeptides to be able to retain enzymatic activity at elevated temperatures and solvent conditions in order to drive the reaction to completion. For example, the transaminase polypeptide of SEQ ID NO:2 may lose activity at elevated temperature (e.g., 40-45° C.) or in presence of reaction components, e.g., amine donor isopropylamine. In some embodiments, the thermostable polypeptides of the disclosure are characterized by higher retention of activity when treated for about 0.5 to 24 hours at about 35° C. to 50° C., at a pH of about 7.5 to 9.0, as compared to transaminase of SEQ ID NO:2. In some embodiments, the amount of enzymatic activity remaining, i.e., residual activity, following treatment at the defined elevated temperature can be at least 5%, 10%, 20%, 30%, 40%, 50% or more of the activity of an untreated polypeptide as assayed at a defined condition. In some embodiments, the elevated temperature condition is 50° C. for 23 hrs. Under the latter condition, the naturally-occurring transaminase of SEQ ID NO:2 has no residual activity following treatment at the defined condition while the engineered transaminases of the disclosure retains significant activity. For example, the transaminase of SEQ ID NO:16 or 18 following treatment at 50° C. for 23 hrs is capable of converting 10% and 23%, respectively, of the substrate pyruvate to product alanine in presence of amino donor isopropylamine, under the assay condition described in the Examples.

In some embodiments, the engineered transaminase polypeptides are characterized by resistance against inactivation by a solvent or reaction component, e.g., isopropylamine. In some embodiments, the engineered transaminase enzymes are resistant to inactivation by up to 1 M or by up to 2 M isopropylamine. In some embodiments, the amount of enzymatic activity remaining, i.e., residual activity, following treatment with solvent or reaction component (e.g., isopropylamine) can be at least 5%, 10%, 20%, 30%, 40%, 50% or more of the activity of an untreated polypeptide.

In some embodiments, the improved transaminase polypeptide characterized by increased thermo- and/or solvent stability comprises an amino acid sequence that is at least 80%, 85%, 90%, 91%, 92%, 93%, 94%, 95%, 96%, 97%, 98%, 99% or more identical to the sequence of SEQ ID NO: 10, 16, or 18. In some embodiments, the transaminase polypeptide characterized by increased thermostability corresponds to the sequence of SEQ ID NO: 10, 16, or 18.

In some embodiments, the transaminase polypeptides having improved thermostability (as compared to SEQ ID NO:2) can have residue differences as compared to SEQ ID NO:2 at one or more of the following residue positions: X4, X9, X12, X21, X45, X86, X157, X177, X208, X211, X253, X272, X294, X302, X316, X324, X391, X398, X418, X420, X431, X444, and X446. In some embodiments, the number of residue differences can be at least 2, 3, 4, 5, or 6 or more of the specified residue positions associated with increased thermostability.

In some embodiments, the transaminase polypeptides improved as compared to SEQ ID NO:2 with respect to their thermostability have one or more of the following features: X4 is R, Q, or L; X9 is T; X12 is K; X21 is N; X45 is H; X86 is Y; X157 is T; X177 is L; X208 is I; X211 is K; X253 is M; X272 is A; X294 is V; X302 is K; X316 is K; X324 is G; X391 is A; X398 is R; X418 is V; X420 is N; X431 is D; X444 is V; and X446 is V.

In some embodiments, the improved transaminase polypeptide characterized by increased thermostability includes, but are not limited to, an amino acid sequence having one of the following feature or set of features: X45 is H, X86 is Y, X177 is L, X211 is K, X294 is V, X324 is G, X391 is A, X398 is R, and X420 is N; X9 is T, X45 is H, X86 is Y, X177 is L, X211 is K, X294 is V, X324 is G, and X391 is A; X21 is N, X45 is H, X177 is L, X208 is I, X211 is K, X324 is G, X391 is A; and X9 is T, X21 is N, X86 is Y, X208 is I, and X294 is V.

In some embodiments, the transaminase polypeptide is improved with respect to, among other properties, enzyme activity, substrate recognition, stereospecificity and/or stereoselectivity. These characteristics can be present in the context of a thermo- and/or solvent stable engineered transaminase, such as SEQ ID NO: 10, 16 or 18. For example, the thermo/solvent stable transaminases can be modified to have improvements in other enzyme properties while retaining its thermo/solvent stable characteristics. A significant advantage of having a thermo- and/or solvent stable transaminase as a basis for obtaining improvements in other enzyme properties, e.g., substrate recognition, enzyme activity, stereoselectivity, stereospecificity, is that the engineered transaminase can be used under a process condition that is unsuitable for the naturally occurring enzyme, for example, among others, (a) screening for activity on various substrates at conditions of elevated temperature and/or high solvent concentrations; (b) scale-up conditions where transamination reactions may be carried out for longer time periods, and/or (c) under high substrate loading conditions. In some embodiments, screening with substrates at the elevated temperature and/or higher solvent concentration maintains the thermo- and/or solvent stable features of the transaminase polypeptide while allowing for identification of improvements in other enzyme properties.

However, in some embodiments, the improvements in other enzyme properties can be in the context of the naturally occurring transaminase polypeptide, such as the sequence of SEQ ID NO:2. Accordingly, in some embodiments, the engineered transaminase polypeptides characterized by improvements in enzyme activity, substrate recognition or stereoselectivity can comprise an amino acid sequence that is at least 80%, 85%, 90%, 91%, 92%, 93%, 94%, 95%, 96%, 97%, 98%, 99% or more identical to the sequence of SEQ ID NO:2 and having the indicated improved property.

In some embodiments, the improved property of the transaminase polypeptide is with respect to an increase in its rate of conversion of the substrate to the product. This improvement in enzymatic activity can be manifested by the ability to use less of the improved polypeptide as compared to the wild-type (SEQ ID NO:2), or other reference sequence (e.g., SEQ ID NO:18), to produce the same amount of product in a given amount of time. In some embodiments, the improvement in enzymatic activity can be manifested by the ability to convert a greater percentage of the substrate to product in a defined time with the same amount of enzyme as compared to the wild type or reference enzyme. In some embodiments, the transaminase polypeptides are capable of converting the substrate to products at a rate that is at least 1.1-fold, 1.5 fold, 2 fold, 3 fold, 4 fold, 5-fold, 10-fold, 25-fold, 50-fold, 75-fold, 100-fold, 150-fold, 200-fold, 250-fold, 300-fold, 500-fold, 1000-fold or more over the rate of SEQ ID NO:2 or SEQ ID NO:18.

In some embodiments, the transaminase polypeptides characterized by improved enzymatic activity, i.e., greater rate of converting the substrates to products as compared to SEQ ID NO:2 and/or SEQ ID NO:18, can comprise an amino acid sequence having one or more of the following features: X30 is A; X31 is A; X44 is A; X45 is N; X56 is V; X57 is, A, C, F, I, L, or S; X81 is D; X82 is H; X85 is A, C, S, N, T, G, or V; X86 is F, S, N, A, G, or H; X95 is T; X112 is I; X113 is C or H; X127 is L; X147 is G; X153 is A, C, G, N, M, Q, S, or T; X166 is S; X177 is V; X181 is R; X208 is I; X211 is R; X228 is G or T; X233 is L, S, I, V, N, G, or T; X294 is M; V297 is A, S, T, I, M, Q, C, or G; X311 is V; X314 is T or V; X317 is L, M, or Y; X318 is G, F, C, K, W, or R; X319 is Q, G, M, N, or V, X320 is A or K; X321 is L, M, or I; X324 is S; X385 is R; X398 is R; X407 is S; X408 is A; X409 is G; X415 is M; X417 is A, C, E, F, I, N, Q, Y, S, T, or V; X420 is N; X434 is V; and X438 is L.

In some embodiments, transaminase polypeptides that are capable of an increased enzymatic activity can comprise an amino acid sequence having one or more of the following features: X30 is A; X31 is A; X56 is V; X81 is D; X82 is H; X95 is T; X113 is C or H.

In some embodiments, the transaminase polypeptides that are improved as compared to SEQ ID NO:2, and/or SEQ ID NO:18 with respect to their rate of enzymatic activity, e.g., their rate of converting the substrates to products can comprise an amino acid sequence having one of the following set of features: X12 is G and X434 is V; X44 is A and X166 is S; X57 is I and X153 is S; X81 is D and X86 is H; X82 is H and X417 is F; X85 is A and X317 is L; X85 is S and X153 is A; X85 is A and X153 is A; X85 is S and X153 is S. X86 is S and X153 is S; X86 is H and X153 is A; X112 is I and X317 is L; or X113 is H and X407 is S; X153 is S and X233 is S; X311 is V and X314 is T; X314 is V and X409 is G; and X318 is G and X408 is A.

In some embodiments, the transaminase polypeptides that are improved as compared to SEQ ID NO:2, and/or SEQ ID NO:18 with respect to their rate of enzymatic activity, i.e., their rate of converting the substrates to products can comprise an amino acid sequence having at least one of the following set of features: X57 is A, X153 is S and X318 is G; X57 is F, X86 is H and X153 is Q; X57 is I, X86 is F and X320 is A; X57 is F, X86 is F and X153 is Q; X57 is A, X153 is C and X321 is L; X57 is C, X86 is S and X417 is T; X57 is C, X86 is A and X317 is L; X57 is F, X318 is F and X417 is S; X57 is L, X86 is S and X153 is A; X57 is F, X318 is G and X417 is I; X57 is L, X86 is F and X318 is F; X57 is L, X417 is C and X438 is L; X57 is F, X127 is L and X417 is C; X57 is S, X233 is L and X417 is V; X57 is S, X86 is G and X417 is C; X85 is A, X147 is G and X153 is A; X85 is S, X153 is A and X233 is T; X85 is A, X153 is S and X417 is S; X86 is H, X153 is A and X417 is C; X86 is H, X153 is S and X417 is C; X86 is F, X153 is C and X297 is A; X86 is S, X153 is T and X297 is A; X86 is H, X233 is L and X417 is A; X86 is F, X318 is R and X417 is A; X86 is N, X228 is G and X317 is L; X95 is T, X153 is A and X417 is C; X113 is C, X385 is R and X417 is C; X153 is A, X317 is L and X318 is G; X153 is A, X233 is T and X417 is C; X153 is S, X318 is R and X417 is E; X153 is C, X233 is L and X318 is R; X153 is T, X228 is G and X321 is L; X153 is S, X317 is L and X417 is C; X153 is T, X319 is V and X417 is I; X153 is S, X228 is G and X417 is V; X153 is C, X317 is Y and X319 is Q; X153 is T, X228 is G and X417 is A; X228 is G, X317 is L and X417 is C; X228 is G, X318 is G and X417 is C; X233 is L, X321 is L and X417 is I; and X317 is L, X318 is R and X417 is T.

In some embodiments, the transaminase polypeptides that are improved as compared to SEQ ID NO:2 and/or SEQ ID NO:18 with respect to their rate of enzymatic activity, i.e., their rate of converting the substrates to products, can comprise an amino acid sequence having one the following set of features: X57 is L and X86 is F and X153 is S and X233 is T and X417 is T; X86 is H and X153 is A and XA228 is G and X417 is I; and X86 is H and X153 is S and X181 is R and X417 is T.

In some embodiments, the transaminase polypeptides described herein are capable of stereoselectively converting amino acceptor substrates to the corresponding chiral amine products, at a rate that is greater than the wild-type transaminase of *Vibrio fluvialis* (SEQ ID NO:2). Polypeptides that are capable of the above reaction include, but are not limited to, a polypeptide comprising an amino acid sequence corresponding to SEQ ID NO:18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, or 192. Activities of the engineered transaminases with respect to specific substrates are described in further detail below.

In some embodiments, the improved property of the transaminase polypeptide is with respect to an increase of its stereoselectivity for converting the amino acceptor substrate to a chiral amino product. In some embodiments, the improved property of the transaminase is with respect to an increase in stereoselectivity, i.e., herein, an increase in the stereomeric excess of the product. In some embodiments, the improved property of the transaminase property is with respect to producing the S enantiomers of chiral amines in stereomeric excess. In some embodiments, the improved property of the transaminase property is with respect to producing the R enantiomers of chiral amines in stereomeric excess.

In some embodiments, the transaminase polypeptides are characterized by the ability to convert amino acceptor substrates to the chiral amine products of the (R) configuration in stereomeric excess greater than the polypeptide of SEQ ID NO:18. In some embodiments, the R-selective transaminase polypeptides comprise an amino acid sequence having one or more of the following features: X57 is L; X81 is D; X82 is H; X85 is A, C, N, T, or V; X86 is S, F, or H; X95 is T; X112 is I; X147 is G; X153 is A, S, N, G, or T; X233 is S or T; X317 is L, X318 is G or R; and X319 is V.

In some embodiments, the transaminase polypeptides capable of converting amino acceptor substrates to the chiral amine products of predominately the (R) configuration at a rate that is greater than the thermostable polypeptide of SEQ ID NO:18 can comprise an amino acid sequence having one of the following features: X85 is A; X85 is A and X153 is A; and X85 is S and X153 is A.

In some embodiments, the transaminase polypeptide capable of converting amino acceptor substrates to the chiral amine products of predominately the (R) configuration at a rate that is greater than the polypeptide of SEQ ID NO:18 comprises an amino acid sequence, corresponding to SEQ ID NO: 22, 30, 32, 34, 36, 40, 44, 48, 56, 58, 60, 62, 64, 66, 68, 70, 72, 76, 84, 88, 90, 92, 104, 108, 110, 120, 122, 124, 126, 128, 132, 160, or 176.

In some embodiments, the transaminase polypeptide capable of converting amino acceptor substrates to the chiral amine products of predominately the (R) configuration at a rate that is greater than the thermostable polypeptide of SEQ ID NO:18 comprises an amino acid sequence corresponding to SEQ ID NO: 32, 36, 40, 56, 58, 60, 62, 64, 66, 122, 124, 126, 128, or 132

In some embodiments, the transaminase polypeptide capable of converting amino acceptor substrates to the chiral amine products of predominately the (R) configuration, at a rate that is greater than the thermostable polypeptide of SEQ ID NO:18 comprises an amino acid sequence corresponding to SEQ ID NO: 122, 124, 126, 128, 130, or 132.

In some embodiments, the engineered transaminase polypeptides are capable of binding and converting structurally diverse substrates. In some instances, the conversion rates for structurally different substrates for the naturally occurring *V fluvialis* enzyme may be insignificant. Accordingly, in some embodiments, the engineered transaminase polypeptides are characterized by increased conversion rates for substrates that are not converted at significant rates by the polypeptide of SEQ ID NO:2 or another engineered transaminase, such as SEQ ID NO:18.

In some embodiments, the transaminase polypeptides are characterized by the capability of stereoselectively converting the substrate 3,4-dihydronaphthalen-1(2H)-one, to the product (S)-1,2,3,4-tetrahydronaphthalen-1-amine, as below,

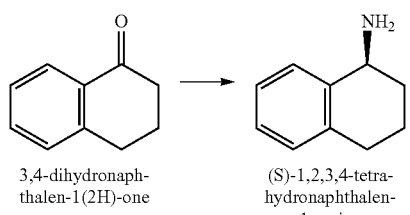

3,4-dihydronaph-
thalen-1(2H)-one (S)-1,2,3,4-tetra-
hydronaphthalen-
1-amine at a rate that is greater than the polypeptide of SEQ ID NO:2 and/or SEQ ID NO:18. Residue positions associated with increase in activity on substrate 3,4-dihydronaphthalen-1 (2H)-one include one or more of the following: X30, X44, X57, X82, X85, X113, X153, X166, X233, X314, X311, X317, X318, X319, X320; X407, X409, and X417.

In some embodiments, the transaminase polypeptides capable of converting 3,4-dihydronaphthalen-1(2H)-one to (S)-1,2,3,4-tetrahydronaphthalen-1-amine at a rate greater than SEQ ID NO:2 or SEQ ID NO:18 comprises an amino acid sequence having at least one or more of the following features or set of features: X30 is A; X31 is A; X57 is I; X82 is H; X85 is V; X85 is C; X153 is S; X317 is M; X317 is Y; X417 is A; X319 is Q; X320 is A; X417 is I; X113 is H and X407 is S; X44 is A and X166 is S; X314 is V and X409 is G; X153 is S and X233 is S; X311 is V and X314 is T; X153 is S, X318 is R and X417 is E; X153 is C, X233 is L and X318 is R; X153 is S, X317 is L and X417 is C; X233 is L, X321 is L, and X417 is I; and X153 is C, X317 is Y and X319 is Q.

In some embodiments, the transaminase polypeptides capable of converting 3,4-dihydronaphthalen-1(2H)-one to (S)-1,2,3,4-tetrahydronaphthalen-1-amine at a rate greater than SEQ ID NO:2 and/or SEQ ID NO:18 comprises an amino acid sequence corresponding to SEQ ID NO: 38, 42, 44, 52, 56, 66, 74, 76, 78, 80, 82, 84, 94, 96, 98, 100, 104, 118, 160, 164, 172, 184, or 188.

In some embodiments, the transaminase polypeptide is capable of stereoselectively converting 3,4-dihydronaphthalen-1(2H)-one to (S)-1,2,3,4-tetrahydronaphthalen-1-amine at a rate that is at least 5-fold or greater than the polypeptide of SEQ ID NO:2 and/or SEQ ID NO:18. Polypeptides that are capable of the above reaction include, but are not limited to, a polypeptide comprising an amino acid sequence corresponding to SEQ ID NO: 44, 104, 164, 172, 184, or 188.

In some embodiments, the transaminase polypeptide is capable of stereoselectively converting 3,4-dihydronaphthalen-1(2H)-one to (S)-1,2,3,4-tetrahydronaphthalen-1-amine at a rate that is at least 10 fold greater than the polypeptide of SEQ ID NO:2 and/or SEQ ID NO:18. Polypeptides that are capable of the above reaction include, but are not limited to, a polypeptide comprising an amino acid sequence corresponding to SEQ ID NO: 164 or 188.

In some embodiments, the transaminase polypeptide is capable of stereoselectively converting the substrate 1-phenylbutan-2-one to the product (S)-1-phenylbutan-2-amine, as below

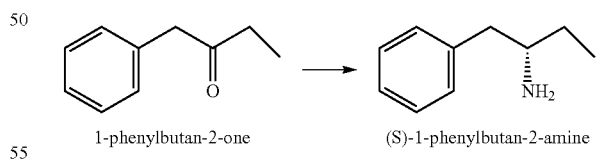

1-phenylbutan-2-one (S)-1-phenylbutan-2-amine at a rate that is greater than the polypeptide of SEQ ID NO:2 and/or SEQ ID NO:18. Residue positions associated with increase in activity on substrate 1-phenylbutan-2-one include one or more of the following: X57; X81; X86; X153; X181; X228; X233; X317; X318; X319; X321; and X417.

In some embodiments, the transaminase polypeptides capable of converting 1-phenylbutan-2-one, to the product (S)-1-phenylbutan-2-amine at a rate that is greater than the wild-type *Vibrio fluvialis* (SEQ ID NO:2) comprise an amino acid sequence having at least one of the following features or set of features: X81 is D and X86 is H; X86 is H and X153 is A; X86 is H, X153 is A and X417 is C; X86 is H, X153 is S and X417 is C; X86 is H, X153 is A, X228 is G and X417 is I; X86 is H, X153 is S, X181 is R and X417 is T; X228 is G, X317 is L and X417 is C; X57 is A, X153 is S and X318 is G; X57 is F, X86 is H, and X153 is Q; X57 is A X153 is C and X321 is L; X86 is F, X318 is R and X417 is A; X228 is G, X318 is G and X417 is C; X153 is S, X318 is R and X417 is E; X153 is C, X233 is L and X318 is R; X86 is N, X228 is G and X317 is L; X153 is T, X228 is G and X321 is L; X153 is S, X317 is L, X417 is C; X57 is L, X86 is S and X153 is A; X153 is S, X228 is G and X417 is V; X153 is C, X317 is Y and X319 is Q; and X153 is T, X228 is G and X417 is A.

In some embodiments, the transaminase polypeptide capable of stereoselectively converting 1-phenylbutan-2-one, to the (S)-1-phenylbutan-2-amine comprises an amino acid sequence corresponding to SEQ ID NO: 22, 88, 90, 92, 106, 110, 138, 140, 142, 148, 150, 152, 160, 164, 168, 170, 172, 178, 182, 188, or 190.

In some embodiments, the transaminase polypeptide is capable of stereoselectively converting 1-phenylbutan-2-one, to (S)-1-phenylbutan-2-amine at a rate that is at least 5-fold or greater than the polypeptide of SEQ ID NO:2 and/or SEQ ID NO:18. In some embodiments, the transaminase polypeptide capable of stereoselectively converting 1-phenylbutan-2-one to the (S)-1-phenylbutan-2-amine at a rate at least 5 times greater than the polypeptide of SEQ ID NO:2 or SEQ ID NO:8 comprises an amino acid sequence corresponding to SEQ ID NO: 22, 88, 90, 92, 106 or 110.

In some embodiments, the transaminase polypeptide described herein is capable of stereoselectively converting the substrate 3,3-dimethylbutan-2-one, to the product (S)-3,3-dimethylbutan-2-amine, as below:

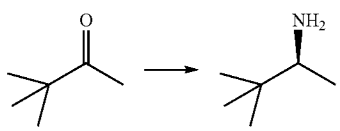

3,3-dimethylbutan-2-one (S)-3,3-dimethylbutan-2-amine at a rate that is greater than the polypeptide of SEQ ID NO:2 and/or SEQ ID NO:18. Residue positions associated with increase in activity on substrate 3,3-dimethylbutan-2-one include one or more of the following: X12, X30, X31, X44, X57, X81, X82, X85, X86, X95, X112, X113, X127, X153, X166, X181, X228, X233, X297, X311, X314, X317, X318, X319, X320, X321, X385, X407, X408, X409, X417, X434, and X438.

In some embodiments, the transaminase polypeptides capable of converting 3,3-dimethylbutan-2-one, to the product (S)-3,3-dimethylbutan-2-amine at a rate that is greater than the polypeptide of SEQ ID NO:2 and/or SEQ ID NO:18 comprises an amino acid sequence having at least one of the following features or set of features: X30 is A; X31 is A; X57 is L; X57 is I; X82 is H; X85 is V; X85 is S; X85 is T; X85 is A; X85 is N; X85 is C; X86 is S; X86 is N; X86 is F; X153 is T; X153 is N; X153 is G; X153 is S; X317 is M; X317 is Y; X319 is Q; X320 is A; X417 is A; X417 is I; X417 is C; X12 is G and X434 is V; X44 is A and X166 is S; X57 is I and X153 is S; X81 is D and X86 is H; X82 is H and X417 is F; X85 is S and X153 is A; X85 is A and X153 is A; X85 is A and X317 is L; X86 is H and X153 is A; X86 is S and X153 is S; X112 is I and X317 is L; X113 is H and X407 is S; X153 is S and X233 is S; X311 is V and X314 is T; X314 is V and X409 is G; X318 is G and X408 is A; X57 is L, X417 is C and X438 is L; X57 is F, X127 is L and X417 is C; X57 is S, X233 is L and X417 is V; X57 is A, X153 is S and X318 is G; X57 is F, X86 is H and X153 is Q; X57 is I, X86 is F and X320 is A; X57 is F, X86 is F and X153 is Q; X57 is C, X86 is S and X417 is T; X57 is F, X318 is F and X417 is S; X57 is L, X86 is S and X153 is A; X57 is L, X86 is F and X318 is F; X57 is F, X318 is G and X417 is I; X86 is H, X153 is S and X417 is C; X86 is H, X153 is A and X417 is C; X86 is F, X153 is C and X297 is A; X86 is H, X233 is L and X417 is A; X86 is N, X228 is G and X317 is L; X95 is T, X153 is A, and X417 is C; X113 is C, X385 is R and X417 is C; X153 is A, X317 is L and X318 is G; X153 is A, X233 is T and X417 is C; X153 is C, X233 is L and X318 is R; X153 is T, X228 is G, and X321 is L; X153 is S, X317 is L, and X417 is C; X153 is T, X319 is V and X417 is I; X153 is S, X228 is G and X417 is V; X153 is C, X317 is Y, and X319 is Q; X153 is T, X228 is G and X417 is A; X233 is L, X321 is L and X417 is I; X228 is G, X318 is G and X417 is C; X317 is L, X318 is R and X417 is T; X86 is H, X153 is A, X228 is G and X417 is I; and X86 is H, X153 is S, X181 is R and X417 is T.

In some embodiments, the transaminase polypeptide capable of stereoselectively converting 3,3-dimethylbutan-2-one to (S)-3,3-dimethylbutan-2-amine comprises an amino acid sequence corresponding to SEQ ID NO: 20, 22, 24, 26, 28, 30, 32, 34, 36, 38, 40, 42, 44, 46, 48, 50, 52, 54, 56, 58, 60, 62, 64, 66, 70, 72, 74, 76, 78, 80, 82, 84, 86, 88, 90, 92, 94, 96, 98, 100, 102, 104, 106, 108, 110, 112, 114, 116, 118, 120, 134, 140, 142, 144, 146, 152, 154, 156, 158, 162, 164, 168, 170, 172, 174, 176, 178, 180, 182, 184, 186, 188, 190, or 192.

In some embodiments, the transaminase polypeptide is capable of stereoselectively converting 3,3-dimethylbutan-2-one to (S)-3,3-dimethylbutan-2-amine, at a rate that is at least 1.1 fold or greater than the polypeptide of SEQ ID NO:2 and/or SEQ ID NO:18. In some embodiments, the transaminase polypeptide capable of stereoselectively converting 3,3-dimethylbutan-2-one to (S)-3,3-dimethylbutan-2-amine at a rate that is at least 1.1 fold or greater than the polypeptide of SEQ ID NO:2 and/or SEQ ID NO:18 comprises an amino acid sequence corresponding to SEQ ID NO: 30, 34, 38, 44, 52, 54, 70, 72, 74, 76, 80, 82, 96, 98, 100, 104, 118, 120, 164, 178, or 188.

In some embodiments, the transaminase polypeptide described herein is capable of stereoselectively converting the substrate octan-2-one, to the product (S)-octan-2-amine, as below:

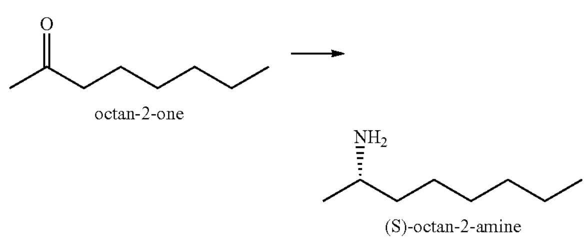

octan-2-one (S)-octan-2-amine at a rate that is greater than the polypeptide of SEQ ID NO:2 and/or SEQ ID NO:18. Residue positions associated with increase in activity on substrate octan-2-one include one or more of the following: X12, X30, X31, X44, X57, X81, X82, X85, X86, X95, X112, X113, X127, X153, X166, X181, X228, X233, X297, X311, X314, X317, X318, X319, X320, X321, X385, X407, X408, X409, X417, X434, and X438.

In some embodiments, the transaminase polypeptides capable of converting octan-2-one, to the product (S)-octan-2-amine comprises an amino acid sequence having at least one of the following features or set of features: X30 is A; X31 is A; X57 is I; X57 is L; X82 is H; X85 is V; X85 is S; X85 is T; X85 is A; X85 is N; X85 is C; X86 is S; X86 is N; X86 is F; X153 is S; X153 is T; X153 is N; X153 is G; X317 is M; X317 is Y; X417 is A; X319 is Q; X320 is A; X417 is I; X417 is C; X12 is G and X434 is V; X44 is A and X166 is S; X57 is I and X153 is S; X81 is D and X86 is H; X82 is H and X417 is F; X85 is A and X317 is L; X85 is S and X153 is A; X85 is A and X153 is A; X86 is H and X153 is A; X86 is S and X153 is S; X112 is I and X317 is L; X113 is H and X407 is S; X153 is S and X233 is S; X311 is V and X314 is T; X314 is V and X409 is G; X318 is G and X408 is A; X57 is L, X417 is C and X438 is L; X57 is F, X127 is L and X417 is C; X57 is S, X233 is L and X417 is V; X57 is S, X86 is G and X417 is C; X57 is A, X153 is S and X318 is G; X57 is F, X86 is H and X153 is Q; X57 is I, X86 is F and X320 is A; X57 is F, X86 is F and X153 is Q; X57 is A, X153 is C and X321 is L; X57 is C, X86 is S and X417 is T; X57 is C, X86 is A and X317 is L; X57 is F, X318 is F and X417 is S; X57 is L, X86 is S and X153 is A; X57 is L, X86 is F and X318 is F; X57 is F, X318 is G and X417 is I; X86 is F, X318 is R and X417 is A; X86 is F, X153 is C and X297 is A; X86 is S, X153 is T and X297 is A; X86 is H, X233 is L and X417 is A; X86 is N, X228 is G, and X317 is L; X86 is H, X153 is A and X417 is C; X86 is H, X153 is S and X417 is C; X95 is T, X153 is A and X417 is C; X113 is C, X385 is R and X417 is C; X153 is A, X233 is T and X417 is C; X153 is S, X318 is R and X417 is E; X153 is C, X233 is L and X318 is R; X153 is S, X228 is G and X417 is V; X153 is C, X317 is Y and X319 is Q; X153 is T, X228 is G, and X417 is A; X153 is T, X319 is V and X417 is I; X153 is T, X228 is G and X321 is L; X153 is S, X317 is L and X417 is C; X153 is A, X317 is L and X318 is G; X228 is G, X318 is G and X417 is C; X228 is G, X317 is L and X417 is C; X233 is L, X321 is L and X417 is I; X317 is L, X318 is R and X417 is T; X86 is H, X153 is A, X228 is G and X417 is I; and X86 is H, X153 is S, X181 is R and X417 is T.

In some embodiments, the transaminase polypeptide capable of stereoselectively converting octan-2-one to (S)-octan-2-amine comprises an amino acid sequence corresponding to SEQ ID NO: 20, 22, 24, 26, 28, 30, 32, 34, 36, 38, 40, 42, 44, 46, 48, 50, 52, 54, 56, 58, 60, 62, 64, 66, 70, 72, 74, 76, 78, 80, 82, 84, 86, 88, 90, 92, 94, 96, 98, 100, 102, 104, 106, 108, 110, 112, 114, 116, 118, 120, 134, 136, 138, 140, 142, 144, 146, 152, 154, 156, 158, 160, 162, 164, 166, 168, 170, 172, 174, 178, 180, 182, 184, 186, 188, 190, or 192.

In some embodiments, the transaminase polypeptide is capable of stereoselectively converting octan-2-one to (S)-octan-2-amine at a rate that is at least 1.1 fold or greater than the polypeptide of SEQ ID NO:2 and/or SEQ ID NO:18. In some embodiments, the transaminase polypeptide capable of steroselectively converting octan-2-one to (S)-octan-2-amine at a rate that is at least 1.1 fold greater than the polypeptide of SEQ ID NO:2 and/or SEQ ID NO:18 comprises an amino acid sequence corresponding to SEQ ID NO: 20, 22, 24, 26, 28, 30, 34, 38, 42, 44, 46, 48, 52, 54, 70, 72, 74, 76, 80, 82, 84, 86, 92, 96, 98, 102, 104, 108, 110, 112, 114, 116, 134, 136, 138, 140, 142, 144, 146, 152, 154, 156, 164, 166, 168, 170, 172, 174, 178, 180, 182, 184, 188, 190, or 192.

In some embodiments, the transaminase polypeptide is capable of stereoselectively converting octan-2-one to (S)-octan-2-amine at a rate that is at least 5 fold or greater than the polypeptide of SEQ ID NO:2 and/or SEQ ID NO:18. Exemplary polypeptides that are capable of stereoselectively converting octan-2-one (S)-octan-2-amine at a rate that is at least 5 fold greater than the polypeptide of SEQ ID NO:2 and/or SEQ ID NO:18 comprises an amino acid sequence corresponding to SEQ ID NO: 22 or 192.

In some embodiments, the transaminase polypeptides described herein are capable of stereoselectively converting the substrate 1-(4-bromophenyl)ethanone, to the product (S)-1-(4-bromophenyl)ethanamine, as below

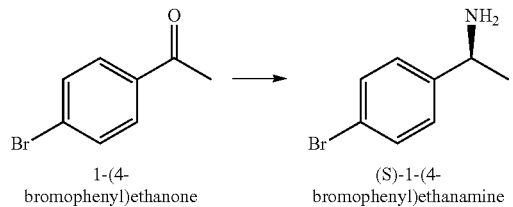

1-(4-bromophenyl)ethanone        (S)-1-(4-bromophenyl)ethanamine at a rate that is greater than the polypeptide of SEQ ID NO:2 and/or SEQ ID NO:18. Residue positions associated with increase in activity on substrate 1-(4-bromophenyl)ethanone include one or more of the following: X12, X30, X31, X44, X57, X81, X82, X85, X86, X95, X112, X113, X127, X153, X153, X166, X181, X228, X233, X297, X311, X314, X317, X318, X319, X320, X321, X385, X407, X408, X409, X417, X434, and X438.

In some embodiments, the transaminase polypeptide capable of stereoselectively converting 1-(4-bromophenyl)ethanone, to (S)-1-(4-bromophenyl)ethanamine comprises an amino acid sequence having at least one of the following features or set of features: X30 is A; X57 is L; X57 is I; X82 is H; X85 is V; X85 is T; X85 is A; X85 is N; X86 is N; X86 is F; X86 is S; X153 is S; X153 is T; X153 is N; X153 is G; X317 is M; X317 is Y; X319 is Q; X320 is A; X417 is A; X417 is I; X417 is C; X12 is G and X434 is V; X44 is A and X166 is S; X57 is I and X153 is S; X81 is D and X86 is H; X82 is H and X417 is F; X85 is S and X153 is A; X85 is A and X153 is A; X86 is S and X153 is S; X86 is H and X153 is A; X112 is I and X317 is L; X113 is H and X407 is S; X153 is S and X233 is S; X314 is V and X409 is G; X318 is G and X408 is A; X31 is A, X311 is V and X314 is T; X57 is L, X417 is C and X438 is L; X57 is F, X127 is L and X417 is C; X57 is I, X86 is F and X320 is A; X57 is S, X86 is G and X417 is C; X57 is C, X86 is S and X417 is T; X57 is C, X86 is A and X317 is L; X57 is F, X318 is F and X417 is S; X57 is L, X86 is S and X153 is A; X57 is F, X318 is G and X417 is I; X86 is H, X153 is A and X417 is C; X86 is H, X153 is S and X417 is C; X86 is F, X318 is R and X417 is A; X86 is F, X153 is C and X297 is A; X86 is S, X153 is T and X297 is A; X86 is N, X228 is G and X317 is L; X86 is H, X233 is L and X417 is A; X95 is T, X153 is A and X417 is C; X113 is C, X385 is R and X417 is C; X153 is A, X233 is T and X417 is C; X153 is A, X317 is L and X318 is G; X153 is S, X318 is R and X417 is E; X153 is T, X228 is G and X321 is L; X153 is S, X317 is L and X417 is C; X153 is C, X233 is L and X318 is R; X153 is S, X228 is G and X417 is V; X153 is T, X319 is V and X417 is I; X153 is C, X317 is Y and X319 is Q; X153 is T, X228 is G and X417 is A; X228 is G, X317 is L and X417 is C; X228 is G, X318 is G and X417 is C; X233 is L, X321 is L and X417 is I; X317 is L, X318 is R and X417 is T; X86 is H, X153 is A, X228 is G and X417 is I; and X86 is H, X153 is S, X181 is R and X417 is T.

In some embodiments, the transaminase polypeptide capable of converting 1-(4-bromophenyl)ethanone to (S)-1-(4-bromophenyl)ethanamine comprises an amino acid sequence corresponding to SEQ ID NO: 20, 22, 24, 26, 28, 30, 34, 36, 38, 40, 42, 44, 46, 48, 50, 52, 54, 56, 60, 62, 64, 68, 70, 72, 74, 76, 78, 80, 82, 84, 86, 88, 90, 92, 94, 96, 98, 100, 102, 104, 106, 108, 110, 112, 114, 116, 118, 120, 136, 138, 144, 150, 152, 154, 156, 158, 160, 162, 164, 166, 168, 170, 172, 174, 176, 178, 182, 184, 186, 188, 190, or 192.

In some embodiments, the transaminase polypeptide is capable of converting 1-(4-bromophenyl)ethanone to (S)-1-(4-bromophenyl)ethanamine at a rate that is at least 1.1 fold or greater than the polypeptide of SEQ ID NO:2 and/or SEQ ID NO:18. In some embodiments, the transaminase polypeptide capable of converting 1-(4-bromophenyl)ethanone to (S)-1-(4-bromophenyl)ethanamine at a rate that is at least 1.1 fold or greater than the polypeptide of SEQ ID NO:2 and/or SEQ ID NO:18 comprises an amino acid sequence corresponding to SEQ ID NO: 20, 22, 24, 26, 28, 34, 38, 42, 44, 46, 48, 50, 52, 54, 68, 70, 72, 74, 76, 78, 80, 82, 84, 86, 88, 92, 94, 96, 98, 100, 102, 104, 108, 110, 112, 114, 116, 118, 136, 150, 152, 154, 156, 160, 164, 166, 170, 172, 174, 182, 184, 186, 188, or 192.

In some embodiments, the transaminase polypeptide is capable of converting 1-(4-bromophenyl)ethanone to the product (S)-1-(4-bromophenyl)ethanamine at a rate that is at least 5 fold or greater than the polypeptide of SEQ ID NO:2 and/or SEQ ID NO:18. In some embodiments, the transaminase polypeptide capable of converting 1-(4-bromophenyl)ethanone to (S)-1-(4-bromophenyl)ethanamine at a rate that is at least 5-fold or greater than the polypeptide of SEQ ID NO:2 and/or SEQ ID NO:18 comprises an amino acid sequence corresponding to SEQ ID NO: 84, 102, 108, 120, 122, 124, 128, 132, 172, 184, or 186.

In some embodiments, the transaminase polypeptide described herein are capable of stereoselectively converting the substrate 4-phenylbutan-2-one, to the product (R)-4-phenylbutan-2-amine, as below:

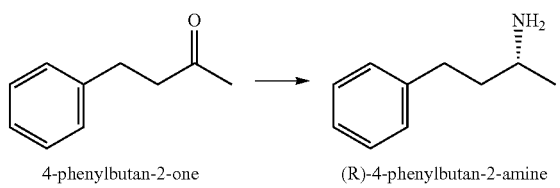

4-phenylbutan-2-one                (R)-4-phenylbutan-2-amine at a rate that is greater than the polypeptide of SEQ ID NO:2 and/or SEQ ID NO:18. Residue positions associated with increase in activity on substrate 4-phenylbutan-2-one include one or more of the following: X30, X31, X44, X57, X81, X82, X85, X86, X113, X153, X166, X181, X228, X233, X297, X317, X318, X319, X320, X321, X385, X407, X408, X417, and X438.

In some embodiments, the transaminase polypeptide capable of stereoselectively converting 4-phenylbutan-2-one to (R)-4-phenylbutan-2-amine comprises an amino acid sequence having at least one of the following features or set of features: X30 is A; X31 is A; X57 is L; X57 is I; X82 is H; X85 is V; X85 is S; X85 is T; X85 is A; X86 is S; X86 is N; X86 is F; X153 is S; X153 is T; X153 is N; X153 is G; X319 is Q; X317 is M; X317 is Y; X320 is A; X417 is A; X417 is I; X417 is C; X44 is A and X166 is S; X57 is I and X153 is S; X81 is D and X86 is H; X82 is H and X417 is F; X85 is A and X153 is A; X85 is A and X317 is L; X85 is S and X153 is A; X86 is S and X153 is S; X86 is H and X153 is A; X113 is H and X407 is S; X318 is G and X408 is A; X153 is S and X233 is S; X57 is A, X153 is S and X318 is G; X57 is F, X86 is H and X153 is Q; X57 is I, X86 is F and X320 is A; X57 is F, X86 is F, and X153 is Q; X57 is A, X153 is C and X321 is L; X57 is L, X417 is C and X438 is L; X57 is S, X233 is L and X417 is V; X57 is C, X86 is S, and X417 is T; X57 is S, X86 is G and X417 is C; X57 is C; X86 is A and X317 is L; X57 is F, X318 is F and X417 is S; X57 is L, X86 is S and X153 is A; X57 is L, X86 is F and X318 is F; X57 is F, X318 is G and X417 is I; X86 is H, X153 is S and X417 is C; X86 is H, X153 is A and X417 is C; X86 is F, X318 is R and X417 is A; X86 is F, X153 is C and X297 is A; X86 is S, X153 is T and X297 is A; X86 is H, X233 is L and X417 is A; X86 is N, X228 is G and X317 is L; X113 is C, X385 is R and X417 is C; X153 is A, X233 is T and X417 is C X153 is A, X317 is L and X318 is G; X153 is S, X318 is R and X417 is E; X153 is C, X233 is L and X318 is R; X153 is T, X228 is G and X321 is L; X153 is S, X317 is L and X417 is C; X153 is S, X228 is G and X417 is V; X153 is C, X317 is Y and X319 is Q; X153 is T, X228 is G and X417 is A; X228 is G, X317 is L and X417 is C; X228 is G, X318 is G and X417 is C; X233 is L, X321 is L and X417 is I; X317 is L, X318 is R and X417 is T; X86 is H, X153 is A, X228 is G and X417 is I; and X86 is H, X153 is S, X181 is R and X417 is T.

In some embodiments, the transaminase polypeptide capable of stereoselectively converting 4-phenylbutan-2-one to (R)-4-phenylbutan-2-amine comprises an amino acid sequence corresponding to SEQ ID NO: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 134, 136, 138, 140, 142, 144, 146, 148, 150, 152, 154, 156, 158, 160, 162, 164, 166, 168, 170, 172, 174, 178, 182, 184, 186, 188, 190, or 192.

In some embodiments, the transaminase polypeptide is capable of stereoselectively converting 4-phenylbutan-2-one to (R)-4-phenylbutan-2-amine at a rate that is at least 1.1 fold or greater than the polypeptide of SEQ ID NO:2 and/or SEQ ID NO:18. In some embodiments, the transaminase polypeptide capable of stereoselectively converting 4-phenylbutan-2-one to (R)-4-phenylbutan-2-amine at a rate that is at least 1.1 fold or greater than the polypeptide of SEQ ID NO:2 and/or SEQ ID NO:18 comprises an amino acid sequence corresponding to SEQ ID NO: 20, 22, 24, 26, 28, 30, 34, 42, 44, 46, 52, 68, 72, 74, 76, 78, 80, 82, 84, 86, 88, 90, 92, 94, 96, 98, 102, 104, 110, 112, 114, 134, 136, 138, 140, 142, 144, 146, 148, 150, 154, 156, 158, 162, 164, 166, 168, 172, 174, 178, 182, 184, 186, 188, 190, or 192.

In some embodiments, the transaminase polypeptide is capable of stereoselectively converting 4-phenylbutan-2-one, to (R)-4-phenylbutan-2-amine at a rate that is at least 5-fold or greater than the polypeptide of SEQ ID NO:2 and/or SEQ ID NO:18. In some embodiments, the transaminase polypeptide capable of stereoselectively converting 4-phenylbutan-2-one to (R)-4-phenylbutan-2-amine at a rate that is at least 5-fold or greater than the polypeptide of SEQ ID NO:2 and/or SEQ ID NO:18, comprises an amino acid sequence corresponding to SEQ ID NO: 154, 172, or 178.

In some embodiments, the transaminase polypeptides described herein are capable of stereoselectively converting the substrate ethyl 3-oxobutanoate, to the product (R)-ethyl 3-aminobutanoate, as below

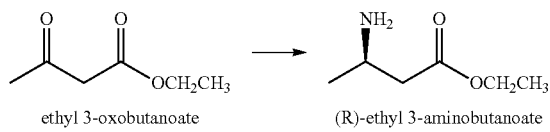

ethyl 3-oxobutanoate    (R)-ethyl 3-aminobutanoate at a rate that is greater than the polypeptide of SEQ ID NO:2 and/or SEQ ID NO:18. Residue positions associated with increase in activity on substrate ethyl 3-oxobutanoate include one or more of the following: X57, X85, X86, X147, X153, X233, X317, X318, and X417.

In some embodiments, the transaminase polypeptide capable of stereoselectively converting ethyl 3-oxobutanoate to (R)-ethyl 3-aminobutanoate comprises an amino acid sequence having at least one of the following features or set of features: X85 is V; X85 is S; X85 is T; X85 is A; X85 is N; X85 is C; X153 is T; X153 is N; X153 is G; X153 is S; X417 is C; X85 is S and X153 is A; X85 is A and X153 is A; X85 is A and X317 is L; X86 is H and X153 is A; X85 is A, X153 is S and X417 is S; X85 is S, X153 is A and X233 is T; X85 is A, X147 is G and X153 is A; X86 is H, X153 is A and X417 is C; X86 is H, X153 is S and X417 is C; X153 is A, X317 is L and X318 is G; X57 is I, X85 is A, X86 is H and X417 is C; and X57 is L, X86 is F, X153 is S, X233 is T and X417 is T.

In some embodiments, the transaminase polypeptide capable of stereoselectively converting ethyl 3-oxobutanoate to (R)-ethyl 3-aminobutanoate comprises an amino acid sequence corresponding to SEQ ID NO: 32, 34, 36, 40, 44, 56, 58, 60, 62, 64, 66, 68, 70, 72, 86, 88, 90, 92, 122, 126, 128, 130, or 132.

In some embodiments, the transaminase polypeptide is capable of stereoselectively converting ethyl 3-oxobutanoate to (R)-ethyl 3-aminobutanoate at a rate that is at least 5-fold or greater than the polypeptide of SEQ ID NO:2 and/or SEQ ID NO:18. Polypeptides that are capable of the above reaction include, but are not limited to, a polypeptide comprising an amino acid sequence corresponding to SEQ ID NO: 32, 36, 40, 56, 58, 60, 62, 64, 66, 126, 128, or 130.

In some embodiments, the transaminase polypeptides described herein are capable of stereoselectively converting the substrate ethyl 3-oxobutanoate, to the product (S)-ethyl 3-aminobutanoate, as below:

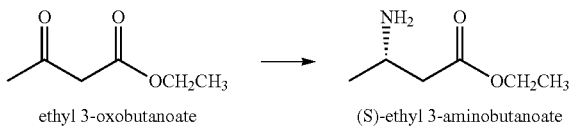

ethyl 3-oxobutanoate    (S)-ethyl 3-aminobutanoate at a rate that is greater than the polypeptide of SEQ ID NO:2 and/or SEQ ID NO:18. Residue positions associated with increase in activity on substrate ethyl 3-oxobutanoate include one or more of the following: X12, X30, X31, X44, X57, X81, X82, X85, X86, X112, X113, X127, X153, X166, X228, X233, X297, X311, X314, X317, X318, X319, X320, X321, X385, X407, X408, X409, X417, X434, and X438.

In some embodiments, the transaminase polypeptide capable of converting ethyl 3-oxobutanoate to (S)-ethyl 3-aminobutanoate comprises an amino acid sequence having at least one of the following features or set of features: X30 is A; X31 is A; X57 is I; X57 is L; X82 is H; X86 is S; X86 is N; X86 is F; X317 is M; X417 is A; X319 is Q; X320 is A; X12 is G and X434 is V; X44 is A and X166 is S; X57 is I and X153 is S; X81 is D and X86 is H; X82 is H and X417 is F; X85 is S and X153 is S; X86 is S and X153 is S; X112 is I and X317 is L; X113 is H and X407 is S; X318 is G and X408 is A; X314 is V and X409 is G; X311 is V and X314 is T; X57 is L, X417 is C and X438 is L; X57 is F, X127 is L and X417 is C; X57 is S, X233 is L and X417 is V; X57 is S, X86 is G and X417 is C; X57 is A, X153 is S and X318 is G; X57 is F, X86 is H and X153 is Q; X57 is I, X86 is F and X320 is A; X57 is F, X86 is F and X153 is Q; X57 is A. X153 is C and X321 is L; X57 is C, X86 is A and X317 is L; X57 is F, X318 is F and X417 is S; X57 is L, X86 is S and X153 is A; X57 is L, X86 is F and X318 is F; X57 is C, X86 is S and X417 is T; X57 is F, X318 is G and X417 is I; X86 is F, X318 is R and X417 is A; X86 is N, X228 is G and X317 is L; X86 is F, X153 is C and X297 is A; X86 is S, X153 is T and X297 is A; X86 is H, X233 is L and X417 is A; X113 is C, X385 is R and X417 is C; X153 is A, X233 is T and X417 is C; X153 is C, X233 is L and X318 is R; X153 is T, X228 is G and X321 is L; X153 is S, X317 is L and X417 is C; X153 is S, X228 is G and X417 is V; X153 is C, X317 is Y and X319 is Q; X153 is T, X228 is G and X417 is A; X228 is G, X317 is L and X417 is C; X228 is G, X318 is G and X417 is C; X233 is L, X321 is L and X417 is I; X317 is L, X318 is R and X417 is T; and X86 is H, X153 is A, X228 is G and X417 is I.

In some embodiments, the transaminase polypeptide capable of stereoselectively converting ethyl 3-oxobutanoate to (S)-ethyl 3-aminobutanoate comprises an amino acid sequence corresponding to SEQ ID NO: 20, 22, 24, 26, 28, 30, 38, 42, 46, 48, 50, 52, 54, 74, 78, 80, 82, 94, 96, 98, 100, 102, 106, 112, 114, 116, 118, 120, 124, 134, 136, 138, 140, 142, 144, 146, 148, 150, 152, 154, 156, 158, 162, 164, 166, 168, 170, 172, 174, 178, 180, 182, 184, 186, 188, 190 or 192.

In some embodiments, the transaminase polypeptide is capable of stereoselectively converting ethyl 3-oxobutanoate to (S)-ethyl 3-aminobutanoate at a rate that is at least 1.1 fold or greater than the polypeptide of SEQ ID NO:2 and/or SEQ ID NO:18. In some embodiments, the transaminase polypeptide capable of converting ethyl 3-oxobutanoate to (S)-ethyl 3-aminobutanoate at a rate that is at least 1.1 fold or greater than the polypeptide of SEQ ID NO:2 and/or SEQ ID NO:18 comprises an amino acid sequence corresponding to SEQ ID NO: 22, 26, 28, 38, 46, 56, 60, 64, 78, 84, 86, 90, 100, 102, 106, 112, 118, 136, 144, 146, 154, 156, 158, 160, 164, 166, 168, 170, 172, 174, 178, 182, 188, or 190.

In some embodiments, the transaminase polypeptide is capable of stereoselectively converting ethyl 3-oxobutanoate to (S)-ethyl 3-aminobutanoate at a rate that is at least 5-fold or greater than the polypeptide of SEQ ID NO:2 and/or SEQ ID NO:18. In some embodiments, the transaminase polypeptide capable of stereoselectively converting ethyl 3-oxobutanoate to (S)-ethyl 3-aminobutanoate at a rate that is at least 5-fold or greater than the polypeptide of SEQ ID NO:2 and/or SEQ ID NO:18 comprises an amino acid sequence corresponding to SEQ ID NO: 22, 26, 28, 38, 46, 56, 60, 64, 78, 84, 86, 90, 100, 102, 106, 112, 118, 136, 144, 154, 166, 170, 174, 178, or 188.

In some embodiments, the transaminase polypeptides described herein are capable of stereoselectively converting the substrate 1-(6-methoxynaphthalen-2-yl)ethanone, to the product (S)-1-(6-methoxynaphthalen-2-yl)ethanamine, as below:

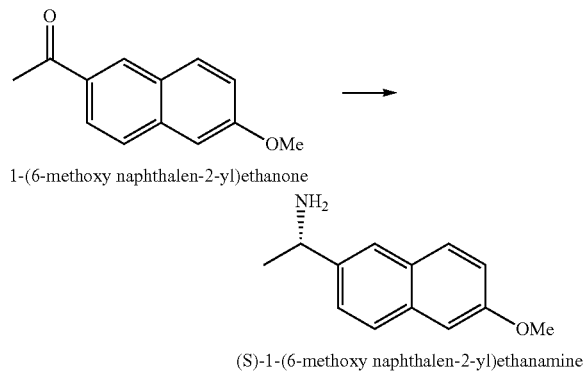

1-(6-methoxy naphthalen-2-yl)ethanone (S)-1-(6-methoxy naphthalen-2-yl)ethanamine

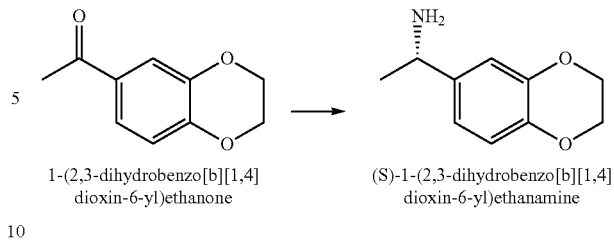

1-(2,3-dihydrobenzo[b][1,4]dioxin-6-yl)ethanone (S)-1-(2,3-dihydrobenzo[b][1,4]dioxin-6-yl)ethanamine at a rate that is greater than the polypeptide of SEQ ID NO:2 and/or SEQ ID NO:18. Residue positions associated with increase in activity on substrate 1-(6-methoxynaphthalen-2-yl)ethanone include one or more of the following: X57, X86, X153, X233, X317, X318, X320, X321, X417, and X438.

In some embodiments, the transaminase polypeptide capable of converting 1-(6-methoxynaphthalen-2-yl)ethanone to (S)-1-(6-methoxynaphthalen-2-yl)ethanamine comprises an amino acid sequence having at least one of the following features or set of features: X57 is L; X86 is F or N; X417 is C, I or A; X57 is L, X86 is F, X153 is S, X233 is T and X417 is T; X57 is C, X86 is S and X417 is T; X57 is S, X233 is L, and X417 is V; X57 is A, X153 is S and X318 is G; X57 is A, X153 is C, and X321 is L; X57 is L, X86 is S, and X153 is A; X57 is S, X86 is G and X417 is C; X57 is L, X86 is F, X318 is F; X57 is F, X86 is F, and X153 is Q; X57 is I; X86 is F and X320 is A; X57 is C, X86 is A and X317 is L; X57 is L, X417 is C and X438 is L; X86 is F, X318 is R and X417 is A; X57 is F. X86 is H and X153 is Q; X57 is F, X318 is F and X417 is S; X86 is H, X153 is S, X181 is R and X417 is T; X153 is S, X317 is L and X417 is C; X153 is T, X228 is G and X417 is A; X57 is F, X127 is L and X417 is C; X228 is G, X317 is L and X417 is C; X233 is L, X321 is L and X417 is I; X228 is G, X318 is G and X417 is C; X86 is H, X153 is S and X417 is C; X86 is H, X233 is L and X417 is A; X86 is S and X153 is S; X86 is F, X153 is C and X297 is A; X153 is S, X228 is G and X417 is V; X57 is F, X318 is G and X417 is I; X153 is T, X228 is G and X321 is L; X317 is L, X318 is R and X417 is T; X153 is C, X317 is Y, and X319 is Q; X57 is I and X153 is S; X86 is H, X153 is A and X417 is C; X153 is A, X233 is T and X417 is C; X95 is T, X153 is A and X417 is C; X86 is N, X228 is G and X317 is L; and X86 is S, X153 is T, X297 is A.

In some embodiments, the transaminase polypeptide capable of stereoselectively converting 1-(6-methoxynaphthalen-2-yl)ethanone to (S)-1-(6-methoxynaphthalen-2-yl)ethanamine comprises an amino acid sequence corresponding to SEQ ID NO: 24, 26, 28, 46, 48, 78, 84, 86, 88, 92, 102, 108, 110, 114, 116, 126, 134, 136, 138, 140, 142, 144, 146, 148, 150, 152, 154, 156, 158, 162, 166, 168, 170, 172, 174, 178, 180, 182, 184, 186, 188, 190, or 192.

In some embodiments, the transaminase polypeptides described herein are capable of stereoselectively converting the substrate 1-(2,3-dihydrobenzo[b][1,4]dioxin-6-yl)ethanone, to the product (S)-1-(2,3-dihydrobenzo[b][1,4]dioxin-6-yl)ethanamine, as below:

at a rate that is greater than the polypeptide of SEQ ID NO:2 and/or SEQ ID NO:18. Residue positions associated with increase in activity on substrate 1-(2,3-dihydrobenzo[b][1,4]dioxin-6-yl)ethanone include one or more of the following: X57, X86, X153, X228, X233, X297, X318, X320, X417, and X438.

In some embodiments, the transaminase polypeptide capable of converting 1-(2,3-dihydrobenzo[b][1,4]dioxin-6-yl)ethanone, to the product (S)-1-(2,3-dihydrobenzo[b][1,4]dioxin-6-yl)ethanamine comprises an amino acid sequence having at least one of the following features or set of features: X31 is A; X57 is C, I or L; X86 is S or F; X153 is G or S; X417 is T or I; X57 is F, X86 is F, and X153 is Q; X57 is I and X153 is S; X57 is L, X86 is F, X153 is S, X233 is T and X417 is T; X86 is F, X153 is C, and X297 is A; X57 is L, X417 is C, and X438 is L; X57 is S, X233 is L, and X417 is V; X57 is L, X86 is S, X153 is A; X57 is S, X86 is G, and X417 is C; X57 is A, X153 is S, X318 is G; X57 is I, X86 is F and X320 is A; X57 is L, X86 is F, X318 is F; X153 is S, X228 is G, and X417 is V; X57 is C, X86 is A, and X317 is L; X153 is S and X233 is S; X57 is A, X153 is C and X321 is L; X86 is S and X153 is S; X86 is H, X153 is S, X181 is R, and X417 is T; X21 is N, X45 is N, X177 is V, X208 is I, X211 is R, X324 is S, and X391 is T; X86 is H, X153 is A, X228 is G, and X417 is I; and X153 is C, X233 is L and X318 is R.

In some embodiments, the transaminase polypeptide capable of stereoselectively converting 1-(2,3-dihydrobenzo[b][1,4]dioxin-6-yl)ethanone, to the product (S)-1-(2,3-dihydrobenzo[b][1,4]dioxin-6-yl)ethanamine comprises an amino acid sequence corresponding to SEQ ID NO: 16, 26, 28, 42, 44, 46, 48, 72, 84, 98, 104, 106, 110, 114, 126, 134, 136, 140, 144, 146, 148, 152, 156, 164, 166, 178, 180, or 182.

In some embodiments, the transaminase polypeptides described herein are capable of stereoselectively converting the substrate 1-(4-phenoxyphenyl)ethanone, to the product (S)-1-(4-phenoxyphenyl)ethanamine, as below:

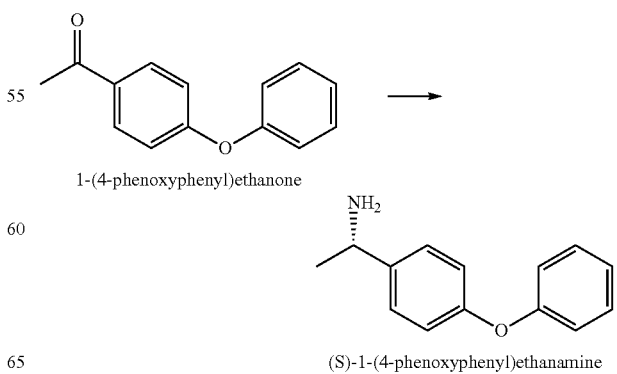

1-(4-phenoxyphenyl)ethanone (S)-1-(4-phenoxyphenyl)ethanamine at a rate that is greater than the polypeptide of SEQ ID NO:2 and/or SEQ ID NO:18. Residue positions associated with increase in activity on substrate 1-(4-phenoxyphenyl)ethanone include one or more of the following: X57, X86, X153, X181, X233, X297, X318, X417, and X438.

In some embodiments, the transaminase polypeptide capable of converting 1-(4-phenoxyphenyl)ethanone, to the product (S)-1-(4-phenoxyphenyl)ethanamine comprises an amino acid sequence having at least one of the following features or set of features: X31 is A; X86 is S or F; X57 is L or I; X153 is S or G; X417 is A or I; X57 is I and X153 is S; X86 is S and X153 is S; X153 is S and X233 is S; X86 is H and X153 is A; X86 is H; X153 is A and X417 is C; X95 is T, X153 is A and X417 is C; X86 is H, X153 is S and X417 is C; X57 is L, X417 is C and X438 is L; X57 is S, X233 is L and X417 is V; X57 is S, X86 is G and X417 is C; X57 is A, X153 is S, X318 is G; X57 is F, X86 is H and X153 is Q; X57 is I, X86 is F and X320 is A; X57 is F, X86 is F and X153 is Q; X57 is C, X86 is S and X417 is T; X86 is F, X153 is C and X297 is A; X86 is H, X233 is L and X417 is A; X153 is C, X233 is L and X318 is R; X57 is C, X86 is A and X317 is L; X57 is L, X86 is S and X153 is A; X57 is L, X86 is F and X318 is F; X153 is S, X228 is G and X417 is V; X153 is T, X228 is G and X417 is A; X86 is H, X153 is A, X228 is G and X417 is I; X86 is H, X153 is S, X181 is R, and X417 is T; and X57 is L, X86 is F, X153 is S, X233 is T and X417 is T.

In some embodiments, the transaminase polypeptide capable of stereoselectively converting 1-(4-phenoxyphenyl)ethanone to the product (S)-1-(4-phenoxyphenyl) ethanamine comprises an amino acid sequence corresponding to SEQ ID NO: 16, 20, 26, 28, 42, 44, 46, 48, 72, 78, 84, 88, 90, 92, 98, 104, 106, 108, 110, 114, 126, 134, 136, 140, 142, 144, 146, 154, 156, 162, 164, 166, 178, 180, 182, or 190.

In some embodiments, the transaminase polypeptides described herein are capable of stereoselectively converting the substrate (R)-4-oxotetrahydro-2H-pyran-3-yl-benzoate to the product (3S,4S)-3-aminotetrahydro-2H-pyran-3-yl benzoate, as below:

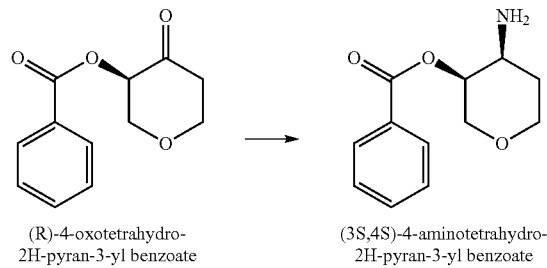 [SMILES: O=C(O[C@@H]1COCCC1=O)c1ccccc1 ; N[C@H]1CCOC[C@H]1OC(=O)c1ccccc1]

(R)-4-oxotetrahydro-2H-pyran-3-yl benzoate    (3S,4S)-4-aminotetrahydro-2H-pyran-3-yl benzoate at a rate that is greater than the polypeptide of SEQ ID NO:2 and/or SEQ ID NO:18. Residue positions associated with increase in activity on substrate (R)-4-oxotetrahydro-2H-pyran-3-yl-benzoate include one or more of the following: X57, X86, X153, X233, X317, X318, X320, X321, and X417.

In some embodiments, the transaminase polypeptide capable of converting (R)-4-oxotetrahydro-2H-pyran-3-yl-benzoate to the product (3S,4S)-3-aminotetrahydro-2H-pyran-3-yl benzoate comprises an amino acid sequence having at least one of the following features or set of features: X57 is I and X153 is S; X57 is A, X153 is S and X318 is G; X57 is A, X153 is C and X321 is L; X57 is L, X86 is S and X153 is A; X57 is I, X86 is F, X320 is A; X57 is S, X86 is G, and X417 is C; X57 is C, X86 is S and X417 is T; X57 is C, X86 is A and X317 is L; X57 is L, X86 is F, X153 is S. X233 is T and X417 is T.

In some embodiments, the transaminase polypeptide capable of stereoselectively converting (R)-4-oxotetrahydro-2H-pyran-3-yl-benzoate, to the product (3S,4S)-3-benzyloxytetrahydro-2H-pyran-4-amine comprises an amino acid sequence corresponding to SEQ ID NO: 46, 126, 136, 140, 144, 148, 154, 166, or 178.

In some embodiments, the transaminase polypeptides described herein are capable of stereoselectively converting the substrate (R)-3-(benzyloxy)dihydro-2H-pyran-4(3H)-one, to the product (3S,4S)-3-(benzyloxy)tetrahydro-2H-pyran-4-amine, as below:

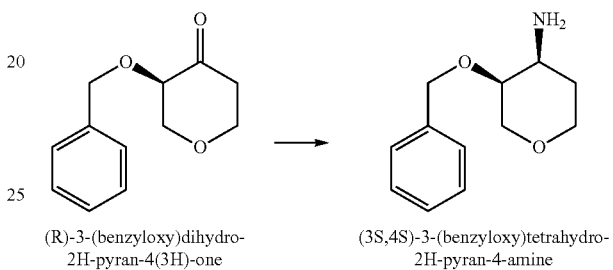

(R)-3-(benzyloxy)dihydro-2H-pyran-4(3H)-one    (3S,4S)-3-(benzyloxy)tetrahydro-2H-pyran-4-amine at a rate that is greater than the polypeptide of SEQ ID NO:2 and/or SEQ ID NO:18. Residue positions associated with increase in activity on substrate (R)-3-(benzyloxy)dihydro-2H-pyran-4(3H)-one include one or more of the following: X57, X86, X153, X233, X317, X318, X320, X321, and X417.

In some embodiments, the transaminase polypeptide capable of converting (R)-3-(benzyloxy)dihydro-2H-pyran-4(3H)-one, to (3S,4S)-3-(benzyloxy)tetrahydro-2H-pyran-4-amine comprises an amino acid sequence having at least one of the following features or set of features: X30 is A; X31 is A; X57 is I or L; X82 is H; X85 is S, T, A; X86 is S, F; X153 is N, G, S, T; X317 is M or Y; X319 is Q; X320 is A; X417 is A, I or C; X57 is I and X153 is S; X85 is S and X153 is S; X81 is D and X86 is H; X86 is H and X153 is A; X86 is S and X153 is S; X85 is S and X153 is A; X85 is A and X153 is A; X314 is V and X409 is G; X311 is V and X314 is T; X82 is H and X417 is F; X85 is A and X317 is L; X318 is G and X408 is A; X153 is S and X233 is S; X113 is H and X407 is S; X12 is G and X434 is V; X112 is I and X317 is L; X44 is A and X166 is S; X86 is H, X153 is S and X417 is C; X57 is F. X127 is L and X417 is C; X57 is S, X86 is G and X417 is C; X228 is G, X317 is L, X417 is C; X57 is F, X86 is H and X153 is Q; X86 is F, X318 is R and X417 is A; X86 is F, X153 is C and X297 is A; X86 is N, X228 is G and X317 is L; X57 is L, X86 is F and X318 is F; X153 is S, X228 is G and X417 is V; X57 is F, X86 is F and X153 is Q; X57 is L, X417 is C and X438 is L; X57 is A, X153 is C and X321 is L; X57 is S, X233 is L and X417 is V; X86 is S, X153 is T and X297 is A; X57 is F, X318 is F and X417 is S; X153 is T, X319 is V and X417 is I; X57 is S, X233 is L and X417 is V; X57 is I, X86 is F and X320 is A; X57 is F, X318 is G and X417 is I; X153 is C, X317 is Y and X319 is Q; X57 is L, X86 is S and X153 is A; X233 is L, X321 is L and X417 is T; X95 is T, X153 is A and X417 is C; X86 is H, X153 is A and X417 is C; X228 is G, X318 is G and X417 is C; X85 is S, X153 is A and X233 is T; X57 is A, X153 is S and X318 is G; X153 is S, X318 is R and X417 is E; X153 is C, X233 is L and X318 is R; X153 is A; X233 is T and X417 is C; X85 is A, X147 is G and X153 is A; X153 is S, X317 is L and X417 is C; X317 is L, X318 is R and X417 is T; X153 is T, X228 is G and X417 is A; X57 is C, X86 is A and X317 is L; X153 is A, X317 is L and X318 is G; X57 is C, X86 is S and X417 is T; X86 is H, X233 is L and X417 is A; X153 is T, X228 is G, X321 is L; X113 is C, X385 is R and X417 is C; X86 is H, X153 is S, X181 is R and X417 is T; X86 is H, X153 is A, X228 is G and X417 is I; X57 is I, X85 is A, X86 is H and X417 is C; and X57 is L, X86 is F, X153 is S, X233 is T and X417 is T.

In some embodiments, the transaminase polypeptide capable of stereoselectively converting (R)-3-(benzyloxy) dihydro-2H-pyran-4(3H)-one to (3S,4S)-3-(benzyloxy)tetrahydro-2H-pyran-4-amine comprises an amino acid sequence corresponding to SEQ ID NO: 20, 22, 26, 28, 30, 32, 34, 36, 40, 42, 44, 46, 48, 50, 52, 58, 60, 68, 70, 72, 78, 82, 84, 86, 88, 90, 92, 94, 96, 98, 100, 102, 104, 106, 108, 110, 114, 116, 118, 122, 126, 128, 130, 132, 134, 136, 138, 140, 142, 144, 146, 148, 150, 152, 154, 156, 158, 160, 162, 164, 166, 168, 170, 172; 174, 176, 178, 180, 182, 184, 186, 188, 190, or 192.

In some embodiments, the expression of the transaminase polypeptides of the invention are improved as compared to the expression of the polypeptide of SEQ ID NO:2 encoded by the polynucleotide of SEQ ID NO:1 in a host cell, particularly an E. coli host cell. In such embodiments, the transaminase polypeptide can have a amino acid sequence having at least one or more of the following features: X4 is R; X6 is R or I or N; X9 is T or G; X6 is R and X133 is T; X12 is K and X302 is K; and X9 is T, X86 is Y and X294 is V. In some embodiments, the transaminase polypeptide with increased expression can be encoded by a polynucleotide sequence having one or more of the following residue differences as compared to the polynucleotide sequence of SEQ ID NO:1 or SEQ ID NO:17: X852 is T and X861 is A; X18 is T and X286 is T; X891 is C; X12 is A and X15 is A and X18 is T; X309 is T; and X561 is C.

Exemplary transaminase polypeptides that are capable of increased expression include, but are not limited to, polypeptides comprising an amino acid sequence corresponding to SEQ ID NO: 4, 6, 8, 12, 14, 194, 196, or 198.

Because the reference polypeptide having the amino acid sequence of SEQ ID NO:18 is capable of converting the substrate to the product at a rate (for example, 100% conversion in 20 hours of 1 g/L substrate with about 10 g/L of the transaminase, in 50% isopropylamine at pH 8) and with a stereoselectivity that is improved over wild-type (SEQ ID NO:2), the polypeptides herein that are improved over SEQ ID NO:18 are also improved over wild-type.

Table 2 below provides a list of SEQ ID NOs having increased thermo- and/or solvent stability as compared to the wildtype transaminase of SEQ ID NO:2. All sequences are derived from the wild-type Vibrio fluvialis transaminase sequence (SEQ ID NO:2). In Table 2 below, each row lists two SEQ ID NOs, where the odd numbers in the column labeled "Nuc ID" refer to the nucleotide sequence that codes for the amino acid sequence provided by the even numbers in the column labeled "Pep ID". The amino acid substitutions as compared to the thermostable Vibrio fluvialis amino acid sequence of SEQ ID NO:2 are listed in the column "Active Amino Acid Mutations."

TABLE 2

List of Sequences and Corresponding Thermostability Improvements

| Nuc ID | Pep ID | Active Amino Acid Mutations (as compared to SEQ ID NO: 2) | % Residual Activity 50° C. 23 h[a] | % Activity at 50° C. rel. to 35° C., 23 h[b] |
|---|---|---|---|---|
| 1 | 2 | — | ND[1] | ND[1] |
| 9 | 10 | A9T; S398R; S420N | 6.0 | ND[1] |
| 11 | 12 | A9T; F86Y; M294V | 4.6 | 0 |
| 15 | 16 | A9T; D21N; F86Y; T208I; M294V | | 18% |
| 17 | 18 | A9T; N45H; F86Y; V177L; R211K; M294V; S324G; T391A | | 53% |

[1]ND = not detectable
[a]% activity measured as % conversion at 50° C. of 1.0M pyruvate with 1.0M isopropylamine at pH 9.
[b]% activity measured as % conversion of pyruvate after 23 h at 50° C. compared to same reaction at 35° C.

Table 3 below provides a list of SEQ ID NOs with their associated activities of transaminases for converting seven different amino acceptor substrates to the corresponding S-enantiomers of the amino products. Substrates 1 to 7 are (Sub 1) 3,4-dihydronaphthalen-1(2H)-one; (Sub 2) 1-phenylbutan-2-one; (Sub 3) 3,3-dimethylbutan-2-one; (Sub 4) octan-2-one; (Sub 5) ethyl 3-oxobutanoate; (Sub 6) 4-phenylbutan-2-one; and (Sub 7) 1-(4-bromophenyl)ethanone. The amino acid substitutions as compared to the thermostable Vibrio fluvialis amino acid sequence of SEQ ID NO:18 are listed in the column "Active Amino Acid Mutations." In the activity columns, one or more plus "+" signs indicate polypeptides having an improved ability to convert the amino acceptor substrate to the chiral amine product as compared to the wild-type amino acid sequence of SEQ ID NO:2. Two plus signs "++" indicates that the polypeptide is about 1.1 to 5-fold improved as compared to SEQ ID NO:18. Three plus signs "+++" indicates that the polypeptide is about 5 to 10-fold improved as compared to SEQ ID NO:18. Four plus signs "++++" indicates that the polypeptide is more than 10-fold improved as compared to SEQ ID NO:18. A blank indicates that data are unavailable. Substrates 3-7 show increased activity with most of the mutated polypeptides. Substrates 1 and 2 show increased activity with fewer polypeptides.

TABLE 3

List of Sequences and Corresponding Activity Improvement

| Nuc ID | Pep ID | Active Amino Acid Mutations | Sub 1 | Sub 2 | Sub 3 | Sub 4 | Sub 5 | Sub 6 | Sub 7 |
|---|---|---|---|---|---|---|---|---|---|
| 19 | 20 | Y86S | | | + | ++ | ++ | ++ | ++ |
| 21 | 22 | G81D; Y86H | | ++++ | + | +++ | + | ++ | ++ |
| 23 | 24 | Y86N | | | + | ++ | ++ | ++ | ++ |
| 25 | 26 | Y86F | | | + | ++ | + | ++ | ++ |
| 27 | 28 | W57L | | | + | ++ | + | ++ | ++ |
| 29 | 30 | Y82H; L417F | | | ++ | ++ | ++ | ++ | + |
| 31 | 32 | F85A; F317L; | | | + | + | + | + | |

TABLE 3-continued

List of Sequences and Corresponding Activity Improvement

| Nuc ID | Pep ID | Active Amino Acid Mutations | Sub 1 | Sub 2 | Sub 3 | Sub 4 | Sub 5 | Sub 6 | Sub 7 |
|---|---|---|---|---|---|---|---|---|---|
| 33 | 34 | V153A; F317L; P318G | | | ++ | ++ | ++ | ++ | ++ |
| 35 | 36 | F85S; V153A | | | + | + | + | + | + |
| 37 | 38 | Y113H; C407S | + | | ++ | ++ | + | + | ++ |
| 39 | 40 | F85A; V153A | | | + | + | + | + | + |
| 41 | 42 | W57I | + | | + | ++ | + | ++ | ++ |
| 43 | 44 | V153S | ++ | | ++ | ++ | ++ | ++ | ++ |
| 45 | 46 | W57I; V153S | | | + | ++ | + | ++ | ++ |
| 47 | 48 | Y86S; V153S | | | + | ++ | ++ | + | ++ |
| 49 | 50 | P318G; T408A | | | + | + | ++ | + | ++ |
| 51 | 52 | Y82H | + | | ++ | ++ | ++ | ++ | ++ |
| 53 | 54 | E12G; M434V | | | ++ | ++ | ++ | + | ++ |
| 55 | 56 | F85V | + | | + | + | + | + | + |
| 57 | 58 | F85S | | | + | + | + | + | |
| 59 | 60 | F85T | | | + | + | + | + | + |
| 61 | 62 | F85A | | | + | + | + | + | + |
| 63 | 64 | F85N | | | + | + | + | + | |
| 65 | 66 | F85C | | | + | + | + | + | |
| 67 | 68 | V153T | + | | ++ | ++ | ++ | ++ | ++ |
| 69 | 70 | V153N | | | ++ | ++ | ++ | + | ++ |
| 71 | 72 | V153G | | | ++ | ++ | ++ | ++ | ++ |
| 73 | 74 | F317M | + | | ++ | ++ | ++ | ++ | ++ |
| 75 | 76 | F317Y | + | | ++ | ++ | ++ | ++ | ++ |
| 77 | 78 | L417A | + | | + | + | + | ++ | ++ |
| 79 | 80 | H319Q | + | | ++ | ++ | ++ | ++ | ++ |
| 81 | 82 | G320A | + | | ++ | ++ | ++ | ++ | ++ |
| 83 | 84 | L417I | + | | + | ++ | + | ++ | +++ |
| 85 | 86 | L417C | | | + | ++ | + | ++ | ++ |
| 87 | 88 | Y86H; V153A; L417C | | +++ | + | + | ++ | ++ | ++ |
| 89 | 90 | Y86H; V153A | | +++ | + | + | + | ++ | + |
| 91 | 92 | Y86H; V153S; L417C | | +++ | + | ++ | ++ | ++ | ++ |
| 93 | 94 | T30A | + | | + | + | ++ | ++ | ++ |
| 95 | 96 | V44A; N166S | + | | ++ | ++ | ++ | ++ | ++ |
| 97 | 98 | V31A | + | | ++ | ++ | ++ | ++ | ++ |
| 99 | 100 | I314V; D409G | + | | ++ | + | + | + | ++ |
| 101 | 102 | V153A; P233T; L417C | | | + | ++ | + | ++ | +++ |
| 103 | 104 | V153S; P233S | ++ | | ++ | ++ | ++ | ++ | ++ |
| 105 | 106 | Y86H; V153A; A228G; L417I | | +++ | + | + | + | + | + |
| 107 | 108 | M95T; V153A; L417C | | | + | ++ | ++ | + | +++ |
| 109 | 110 | Y86H; V153S; C181R; L417T | | +++ | + | ++ | ++ | ++ | ++ |
| 111 | 112 | Y113C; K385R; L417C | | | + | ++ | + | ++ | ++ |
| 113 | 114 | W57L; L417C; F438L | | | + | ++ | + | ++ | ++ |
| 115 | 116 | W57F; M127L; L417C | | | + | ++ | + | ++ | ++ |
| 117 | 118 | I311V; I314T | + | | ++ | + | + | + | ++ |
| 119 | 120 | F112I; F317L | | | ++ | + | ++ | | + |
| 133 | 134 | W57S; P233L; L417V | | | + | ++ | + | ++ | |
| 135 | 136 | W57S; Y86G; L417C | | | | ++ | + | ++ | ++ |
| 137 | 138 | A228G; F317L; L417C | | + | | ++ | ++ | ++ | + |
| 139 | 140 | W57A; V153S; P318G | | + | + | ++ | ++ | ++ | |
| 141 | 142 | W57F; Y86H; V153Q | | ++ | + | ++ | ++ | ++ | |
| 143 | 144 | W57I; Y86F; G320A | | | + | ++ | + | ++ | + |
| 145 | 146 | W57F; Y86F; V153Q | | | + | ++ | +++ | ++ | |
| 147 | 148 | W57A; V153C; F321L | | + | | ++ | ++ | ++ | |
| 149 | 150 | Y86F; P318R; L417A | | + | | + | ++ | ++ | ++ |
| 151 | 152 | A228G; P318G; L417C | | + | + | ++ | ++ | + | ++ |
| 153 | 154 | W57C; Y86S; L417T | | | + | ++ | + | +++ | ++ |
| 155 | 156 | Y86F; V153C; V297A | | | + | ++ | +++ | ++ | ++ |
| 157 | 158 | Y86S; V153T; V297A | | | + | + | +++ | ++ | + |
| 159 | 160 | V153S; P318R; L417E | + | + | | + | +++ | + | ++ |
| 161 | 162 | Y86H; P233L; L417A | | | + | + | ++ | ++ | + |
| 163 | 164 | V153C; P233L; P318R | ++++ | + | ++ | ++ | +++ | ++ | ++ |
| 165 | 166 | W57C; Y86A; F317L | | | | ++ | + | ++ | ++ |
| 167 | 168 | Y86N; A228G; F317L | | + | + | ++ | ++ | + | ++ |
| 169 | 170 | V153T; A228G; F321L | | ++ | + | ++ | ++++ | + | ++ |
| 171 | 172 | V153S; F317L; L417C | ++ | ++ | + | ++ | +++ | +++ | +++ |
| 173 | 174 | W57F; P318F; L417S | | | + | ++ | + | ++ | ++ |
| 175 | 176 | V153T; H319V; L417I | | | + | | ++ | + | ++ |
| 177 | 178 | W57L; Y86S; V153A | | + | ++ | ++ | + | +++ | + |
| 179 | 180 | W57L; Y86F; P318F | | | + | ++ | ++ | ++ | |
| 181 | 182 | V153S; A228G; L417V; | | ++ | + | ++ | +++ | ++ | ++ |
| 183 | 184 | P233L; F321L; L417I | ++ | | + | ++ | ++ | ++ | +++ |
| 185 | 186 | F317L; P318G; L417T | | | + | + | ++ | ++ | +++ |
| 187 | 188 | V153C; F317Y; H319Q | +++ | + | ++ | ++ | ++++ | ++ | ++ |
| 189 | 190 | V153T; A228G; L417A | | ++ | + | ++ | +++ | ++ | + |
| 191 | 192 | W57F; P318G; L417I | | | + | +++ | ++ | ++ | ++ |

Table 4 below provides a list of SEQ ID NOs with their associated activities for converting two different amino acceptor substrates to the corresponding R-enantiomers of the amino products. Substrates 5 and 6 are (Sub 5) ethyl 3-oxobutanoate and (Sub 6) 4-phenylbutan-2-one. All sequences below are derived from the wild-type *Vibrio fluvialis* transaminase sequence (SEQ ID NO:2). In Table 4 below, the odd numbered SED ID NOs in the column labeled "Nuc ID" refer to the nucleotide sequence that codes for the amino acid sequence provided by the even numbered SEQ ID NOs in the column labeled "Pep ID". The amino acid substitutions as compared to the amino acid sequence of SEQ ID NO:18 are listed in the column "Active Amino Acid Mutations." In the activity columns, one or more plus "+" signs indicate polypeptides having an improved ability to convert the amino acceptor substrate to the chiral amine product as compared to the wild-type amino acid sequence of SEQ ID NO:2. Two plus signs "++" indicates that the polypeptide is about 1.1 to 5-fold improved as compared to SEQ ID NO:18. Three plus signs "+++" indicates that the polypeptide is about 5 to 10-fold improved as compared to SEQ ID NO:18. Four plus signs "++++" indicates that the polypeptide is more than 10-fold improved as compared to SEQ ID NO:18. A blank indicates that data are unavailable. Substrate 5 shows increased activity with most of the mutated polypeptides. Substrate 6 shows increased activity with fewer polypeptides.

TABLE 4

List of Sequences and Corresponding Activity Improvement

| Nuc ID | Pep ID | Active Amino Acid Mutations (as compared to SEQ ID NO: 18) | Sub 5 | Sub 6 |
| --- | --- | --- | --- | --- |
| 21 | 22 | G81D; Y86H | + | |
| 29 | 30 | Y82H; L417F | + | |
| 31 | 32 | F85A; F317L | ++++ | |
| 33 | 34 | V153A; F317L; P318G | ++ | |
| 35 | 36 | F85S; V153A | ++++ | |
| 39 | 40 | F85A; V153A | ++++ | |
| 43 | 44 | V153S | ++ | |
| 47 | 48 | Y86S; V153S | ++ | |
| 55 | 56 | F85V | ++++ | |
| 57 | 58 | F85S | ++++ | |
| 59 | 60 | F85T | ++++ | |
| 61 | 62 | F85A | ++++ | |
| 63 | 64 | F85N | ++++ | |
| 65 | 66 | F85C | ++++ | |
| 67 | 68 | V153T | ++ | |
| 69 | 70 | V153N | ++ | |
| 71 | 72 | V153G | ++ | |
| 75 | 76 | F317Y | ++ | |
| 83 | 84 | L417I | + | |
| 85 | 86 | L417C | + | |
| 87 | 88 | Y86H; V153A; L417C | ++ | |
| 89 | 90 | Y86H; V153A | + | |
| 91 | 92 | Y86H; V153S; L417C | ++ | |
| 103 | 104 | V153S; P233S | ++ | |
| 107 | 108 | M95T; V153A; L417C | + | |
| 109 | 110 | Y86H; V153S; C181R; L417T | ++ | |
| 119 | 120 | F112I; F317L | | + |
| 121 | 122 | F85A; W147G; V153A | ++ | ++++ |
| 123 | 124 | F85S; V153S | | ++++ |
| 125 | 126 | W57L; Y86F; V153S; P233T; L417T | +++ | |
| 127 | 128 | F85S; V153A; P233T | +++ | ++++ |
| 129 | 130 | W57I; F85A; Y86H; L417C | +++ | |
| 131 | 132 | F85A; V153S; L417S | ++ | ++++ |
| 159 | 160 | V153S; P318R; L417E | ++ | |
| 175 | 176 | V153T; H319V; L417I | ++ | |

In some embodiments, an improved transaminase comprises an amino acid sequence that is at least about 80%, 85%, 86%, 87%, 88%, 89%, 90%, 91%, 92%, 93%, 94%, 95%, 96%, 97%, 98%, or 99% identical to SEQ ID NO:2 or SEQ ID NO:18, wherein the amino acid sequence comprises any one of the set of mutations contained in any one of the polypeptide sequences listed in Table 3 or Table 4 as compared to a reference sequence corresponding to SEQ ID NO:2 or SEQ ID NO:18. In some embodiments, this transaminase polypeptide comprises any one of the set of mutations listed in Table 3 or Table 4. In some embodiments, the engineered transaminases can have additionally about 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue differences at other residue positions. In some embodiments, the number of differences as compared to the reference sequence can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue positions. In some embodiments, the residue differences comprise conservative mutations.

In some embodiments, an improved transaminase polypeptide comprises an amino acid sequence that is at least about 80%, 85%, 86%, 87%, 88%, 89%, 90%, 91%, 92%, 93%, 94%, 95%, 96%, 97%, 98%, or 99% identical to a reference sequence corresponding to SEQ ID NO: 4, 6, 8, 10, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198, wherein the engineered transaminase amino acid sequence comprises any one of the set of mutations contained in any one of the polypeptide sequences listed in Table 3 or Table 4 as compared to a reference sequence corresponding to SEQ ID NO:2 or SEQ ID NO:18. In some embodiments, this transaminase polypeptide comprises any one of the set of mutations listed in Table 3 or Table 4. In some embodiments, these engineered transaminases can have additionally about 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 residue differences at other residue positions. In some embodiments, the number of differences as compared to the reference sequence can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 residue positions. In some embodiments, the residue differences comprise conservative mutations.

In some embodiments, the amino acid sequences of the polypeptides of the current invention specifically exclude those that differ from the wild-type sequence of *Vibrio fluvialis* by only one of any of the following single mutations: residue X57 is G; residue X147 is G; residue X231 is G; residue X233 is L; residue X265 is L; residue X285 is A; residue X297 is A; and residue X415 is L.

The engineered transaminase enzymes described herein can be obtained by mutagenizing a gene encoding a naturally-occurring wild-type transaminase enzyme that is at least 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of *Vibrio fluvialis* transaminase (SEQ ID NO:2) utilizing standard laboratory techniques, including various mutagenesis and recombination techniques.

As will be appreciated by those of skill in the art, some of the above-defined categories of amino acid residues used to describe the engineered transaminases herein, unless otherwise specified, are not mutually exclusive. Thus, amino acids having side chains exhibiting two or more physicochemical properties can be included in multiple categories.

The appropriate classification of any amino acid or residue will be apparent to those of skill in the art, especially in light of the detailed disclosure provided herein.

In some embodiments, the improved engineered transaminase polypeptides comprise deletions of the engineered transaminase polypeptides described herein. Thus, for each and every embodiment of the transaminase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the transaminase polypeptides, as long as the functional activity and/or improved properties of the transaminase is maintained. In some embodiments, the deletions can comprise, 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 amino acid residues. In some embodiments, the number of deletions can be 1, 2, 3, 4, 5, 6, 7, 8, 9, 10, 15, 16, 17, 18, 19, 20, 21, 22, 23, 24, 25, 30, 30, 35, 40, 45, 50, 55, or 60 amino acids. In some embodiments, the deletions can comprise deletions of 1, 2, 3, 4, 5, 6, 7, 8, 9, 10, 11, 12, 13, 14, 15, 16, 18, 20, 21, 22, 23, 24, 25 or 30 amino acid residues.

In some embodiments, the improved engineered transaminase polypeptides can comprise fragments of the engineered transaminase enzymes described herein. In some embodiments, the polypeptide fragments can be 70%, 80%, 90%, 95%, 98%, or 99% of the full-length transaminase polypeptide, such as the transaminase of SEQ ID NO:18.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Oct); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Oct); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg (tos), Cys (methylbenzyl), Cys (nitropyridinesulfenyl), Glu (δ-benzylester), Gln (xanthyl), Asn (N-δ-xanthyl), His (bom), His (benzyl), His (tos), Lys (fmoc), Lys (tos), Ser (O-benzyl), Thr (O-benzyl) and Tyr (O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered transaminase enzyme can be targeted to a specific property of the enzyme.

In some embodiments, the polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

In some embodiments, the polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the polypeptides can be provided on a physical substrate. In some embodiments, the polypeptides can be provided in the form of an array in which the polypeptides are arranged in positionally distinct locations. The array can be used to test a variety of substrate compounds for conversion by the polypeptides. "Substrate," "support," "solid support," "solid carrier," or "resin" in the context of arrays refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

In certain embodiments, the kits of the present disclosure include arrays comprising a plurality of different transaminase polypeptides at different addressable position, wherein the different polypeptides are different variants of a reference sequence each having at least one different improved enzyme property. Such arrays comprising a plurality of engineered polypeptides and methods of their use are described in, e.g., WO2009/008908A2.

In some embodiments, the transaminase polypeptides can be bound on a physical substrate. The transaminase polypeptide can be bound non-covalently or covalently. Various methods for conjugation to substrates, e.g., membranes, beads, glass, etc. are described in, among others, Hermanson, G. T., Bioconjugate Techniques, Second Edition, Academic Press; (2008), and Bioconjugation Protocols: Strategies and Methods, In Methods in Molecular Biology, C. M. Niemeyer ed., Humana Press (2004); the disclosures of which are incorporated herein by reference.

6.4 Polynucleotides Encoding Engineered Transaminases

In another aspect, the present disclosure provides polynucleotides encoding the engineered transaminase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered transaminase can be introduced into appropriate host cells to express the corresponding transaminase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved transaminase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 3 or Table 4.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In certain embodiments, all codons need not be replaced to optimize the codon usage of the transaminases since the natural sequence will comprise preferred codons and because use of preferred codons may not be required for all amino acid residues. Consequently, codon optimized polynucleotides encoding the transaminase enzymes may contain preferred codons at about 40%, 50%, 60%, 70%, 80%, or greater than 90% of codon positions of the full length coding region.

In some embodiments, the polynucleotide comprises a nucleotide sequence encoding a transaminase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to any of the reference engineered transaminase polypeptides described herein. Accordingly, in some embodiments, the polynucleotide encodes an amino acid sequence that is at least about 80%, 85%, 86%, 87%, 88%, 89%, 90%, 91%, 92%, 93%, 94%, 95%, 96%, 97%, 98%, 99% or more identical to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198, where the polypeptide has transaminase activity and one or more of the improved properties described herein.

In some embodiments, the polynucleotide comprises a nucleotide sequence encoding an engineered transaminase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 10, where the polypeptide has transaminase activity and one or more of the improved properties described herein.

In some embodiments, the polynucleotide comprises a nucleotide sequence encoding an engineered transaminase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 16, where the polypeptide has transaminase activity and one or more of the improved properties described herein.

In some embodiments, the polynucleotide comprises a nucleotide sequence encoding an engineered transaminase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO:18, where the polypeptide has transaminase activity and one or more of the improved properties described herein.

In some embodiments, the polynucleotides encoding the engineered transaminases are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, and 197.

In some embodiments, the polynucleotides are capable of hybridizing under highly stringent conditions to a polynucleotide corresponding to SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, or 197, or a complement thereof, and encodes a polypeptide having transaminase activity with one or more of the improved properties described herein.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered transaminase. In some embodiments, the reference polynucleotide sequence is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, and 197.

An isolated polynucleotide encoding an improved transaminase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide of the present invention would be operably linked with the regulatory sequence.

Thus, in another aspect, the present disclosure is also directed to a recombinant expression vector comprising a polynucleotide encoding an engineered transaminase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAM□1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proc Natl Acad Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3xFLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

6.5 Host Cells for Expression of Transaminase Polypeptides

In another aspect, the present disclosure provides a host cell comprising a polynucleotide encoding an improved transaminase polypeptide of the present disclosure, the polynucleotide being operatively linked to one or more control sequences for expression of the transaminase enzyme in the host cell. Host cells for use in expressing the polypeptides encoded by the expression vectors of the present invention are well known in the art and include but are not limited to, bacterial cells, such as *E. coli*, *Vibrio fluvialis*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the transaminase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved transaminase into the plasmid pCK110900 operatively linked to the lac promoter under control of the lad repressor. The expression vector also contained the P15a origin of replication and the chloramphenicol resistance gene.

6.6 Methods of Generating Engineered Transaminase Polypeptides

In some embodiments, to make the improved polynucleotides and polypeptides of the present disclosure, the naturally-occurring transaminase enzyme that catalyzes the transamination reaction is obtained (or derived) from *Vibrio fluvialis*. In some embodiments, the parent polynucleotide sequence is codon optimized to enhance expression of the transaminase in a specified host cell. As an illustration, the parental polynucleotide sequence encoding the wild-type polypeptide of *Vibrio fluvialis* was constructed from oligonucleotides prepared based upon the known polypeptide sequence of *Vibrio fluvialis* sequence (Shin et al., 2003, "Purification, characterization, and molecular cloning of a novel amine:pyruvate transaminase from *Vibrio fluvialis* JS17" Appl Microbiol Biotechnol. 61(5-6):463-471). The parental polynucleotide sequence, designated as SEQ ID NO: 1, was codon optimized for expression in *E. coli* and the codon-optimized polynucleotide cloned into an expression vector, placing the expression of the transaminase gene under the control of the lac promoter and lad repressor gene.

Clones expressing the active transaminase in *E. coli* were identified and the genes sequenced to confirm their identity. The sequence designated SEQ ID NO: 17 was the parent sequence utilized as the starting point for most experiments and library construction of engineered transaminases evolved from the *Vibrio fluvialis* transaminase.

The engineered transaminases can be obtained by subjecting the polynucleotide encoding the naturally occurring transaminase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, "Oligonucleotide-directed random mutagenesis using the phosphorothioate method," In Methods Mol. Biol. 57:369-74; Smith, 1985, Ann. Rev. Genet. 19:423-462; Botstein et al., 1985, Science 229:1193-1201; Carter, 1986, Biochem. J. 237:1-7; Kramer et al., 1984, Cell, 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

The clones obtained following mutagenesis treatment can be screened for engineered transaminases having a desired improved enzyme property. Measuring enzyme activity from the expression libraries can be performed using the standard biochemistry techniques, such as HPLC analysis following OPA derivitization of the product amine.

Where the improved enzyme property desired is thermostability, enzyme activity may be measured after subjecting the enzyme preparations to a defined temperature and measuring the amount of enzyme activity remaining after heat treatments. Clones containing a polynucleotide encoding a transaminase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources.

Engineered transaminase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the transaminase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved transaminase enzymes. For affinity chromatography purification, any antibody which specifically binds the transaminase polypeptide may be used. For the production of antibodies, various host animals, including but not limited to rabbits, mice, rats, etc., may be immunized by injection with a transaminase polypeptide, or a fragment thereof. The transaminase polypeptide or fragment may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacilli Calmette Guerin*) and *Corynebacterium parvum*.

6.7 Methods of Using the Engineered Transaminase Enzymes and Compounds Prepared Therewith In some embodiments, the transaminases described herein can be used in a method for performing processes shown in Schemes 1 to 3, supra, in which an amino group from an amino donor of general Formula II is transferred to an amino acceptor (ketone substrate) of general Formula I to produce a chiral amine. The reaction can produce the R chiral amine or S chiral amine in stereomeric excess. Generally, the method for performing the transamination reaction can comprise contacting or incubating the amino donor of Formula II and an amino acceptor of Formula I,

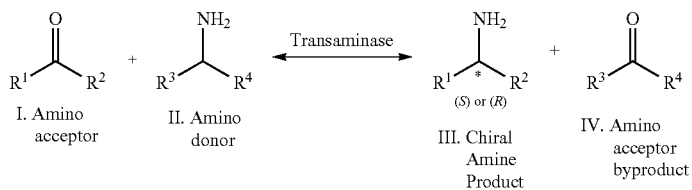

I. Amino acceptor
II. Amino donor
III. Chiral Amine Product (S) or (R)
IV. Amino acceptor byproduct with an engineered transaminase polypeptide of the disclosure under reaction conditions suitable for converting the amine acceptor to the (S) or (R) chiral amine in stereomeric excess. Suitable groups for $R^1$, $R^2$, $R^3$ and $R^4$ are described above.

In some embodiments of the method, the amino acceptors can be selected from pyruvate, dihydronaphthalen-1(2H)-one, 1-phenylbutan-2-one, 3,3-dimethylbutan-2-one, octan-2-one, ethyl 3-oxobutanoate, 4-phenylbutan-2-one, 1-(4-bromophenyl)ethanone, and 2-methyl-cyclohexanone and 7-methoxy-2-tetralone, 1-(6-methoxynaphthalen-2-yl)ethanone, 1-(2,3-dihydrobenzo[b][1,4]dioxin-6-yl)ethanone, 1-(4-phenoxyphenyl)ethanone, (R)-4-oxotetrahydro-2H-pyran-3-yl-benzoate, and (R)-3-(benzyloxy)dihydro-2H-pyran-4(3H)-one.

Accordingly, in some embodiments, the method comprises contacting dihydronaphthalen-1(2H)-one with a transaminase polypeptide of the disclosure in presence of an amino donor under suitable reaction conditions for the conversion of dihydronaphthalen-1(2H)-one to (S)-1,2,3,4-tetrahydronaphthalen-1-amine in enantiomeric excess. In some embodiments of the process, the product (S)-1,2,3,4-tetrahydronaphthalen-1-amine can be formed in at least 10% 20% 30% 40% 50% 60%, 70%, 80%, 90%, or 95% or more stereomeric excess.

In some embodiments, the method comprises contacting 1-phenylbutan-2-one with a transaminase polypeptide of the disclosure in presence of an amino donor under suitable reaction conditions for the conversion of 1-phenylbutan-2-one to (S)-1-phenylbutan-2-amine in enantiomeric excess. In some embodiments of the process, the product (S)-1-phenylbutan-2-amine can be formed in at least 10% 20% 30% 40% 50% 60%, 70%, 80%, 90%, or 95% or more stereomeric excess.

In some embodiments, in some embodiments, the method comprises contacting 3,3-dimethylbutan-2-one with a transaminase polypeptide of the disclosure in presence of an amino donor under suitable reaction conditions for the conversion of 3,3-dimethylbutan-2-one to (S)-3,3-dimethylbutan-2-amine in enantiomeric excess. In some embodiments of the process, the product (S)-3,3-dimethylbutan-2-amine can be formed in at least 10% 20% 30% 40% 50% 60%, 70%, 80%, 90%, or 95% or more stereomeric excess.

In some embodiments, the method comprises contacting octan-2-one with a transaminase polypeptide of the disclosure in presence of an amino donor under suitable reaction conditions for the conversion of octan-2-one to (S)-octan-2-amine in enantiomeric excess. In some embodiments of the process, the product (S)-octan-2-amine can be formed in at least 10% 20% 30% 40% 50% 60%, 70%, 80%, 90%, or 95% or more stereomeric excess.

In some embodiments, the method comprises contacting 1-(4-bromophenyl)ethanone with a transaminase polypeptide of the disclosure in presence of an amino donor under suitable reaction conditions for the conversion of 1-(4-bromophenyl)ethanone to (S)-1-(4-bromophenyl)ethanamine in enantiomeric excess. In some embodiments of the process, the product (S)-1-(4-bromophenyl)ethanamine can be formed in at least 10% 20% 30% 40% 50% 60%, 70%, 80%, 90%, or 95% or more stereomeric excess.

In some embodiments, the method comprises contacting 4-phenylbutan-2-one with a transaminase polypeptide of the disclosure in presence of an amino donor under suitable reaction conditions for the conversion of 4-phenylbutan-2-one to (R)-4-phenylbutan-2-amine in enantiomeric excess. In some embodiments of the process, the product (R)-4-phenylbutan-2-amine can be formed in at least 10% 20% 30% 40% 50% 60%, 70%, 80%, 90%, or 95% or more stereomeric excess.

In some embodiments, the method comprises contacting ethyl 3-oxobutanoate with a transaminase polypeptide of the disclosure in presence of an amino donor under suitable reaction conditions for the conversion of ethyl 3-oxobutanoate to (R)-ethyl 3-aminobutanoate in enantiomeric excess. In some embodiments of the process, the product (R)-ethyl 3-aminobutanoate can be formed in at least 10% 20% 30% 40% 50% 60%, 70%, 80%, 90%, or 95% or more stereomeric excess.

In some embodiments, the method comprises contacting ethyl 3-oxobutanoate with a transaminase polypeptide of the disclosure in presence of an amino donor under suitable reaction conditions for the conversion of ethyl 3-oxobutanoate to (S)-ethyl 3-aminobutanoate in enantiomeric excess. In some embodiments of the process, the product (S)-ethyl 3-aminobutanoate can be formed in at least 10% 20% 30% 40% 50% 60%, 70%, 80%, 90%, or 95% or more stereomeric excess.

In some embodiments, the method comprises contacting 1-(6-methoxynaphthalen-2-yl)ethanone with a transaminase polypeptide of the disclosure in presence of an amino donor under suitable reaction conditions for the conversion of 1-(6-methoxynaphthalen-2-yl)ethanone to (S)-1-(6-methoxynaphthalen-2-yl)ethanamine in stereomeric excess.

In some embodiments, the method comprises contacting 1-(2,3-dihydrobenzo[b][1,4]dioxin-6-yl)ethanone with a transaminase polypeptide of the disclosure in presence of an amino donor under suitable reaction conditions for the conversion of 1-(2,3-dihydrobenzo[b][1,4]dioxin-6-yl)ethanone to (S)-1-(2,3-dihydrobenzo[b][1,4]dioxin-6-yl)ethanamine in stereomeric excess.

In some embodiments, the method comprises contacting 1-(4-phenoxyphenyl)ethanone with a transaminase polypeptide of the disclosure in presence of an amino donor under suitable reaction conditions for the conversion of 1-(4-phenoxyphenyl)ethanone to (S)-1-(4-phenoxyphenyl)ethanamine in stereomeric excess.

In some embodiments, the method comprises contacting (R)-3-(benzyloxy)dihydro-2H-pyran-4(3H)-one with a transaminase polypeptide of the disclosure in presence of an amino donor under suitable reaction conditions for the conversion of (R)-3-(benzyloxy)dihydro-2H-pyran-4(3H)-one, to (3S,4S)-3-(benzyloxy)tetrahydro-2H-pyran-4-amine in stereomeric excess.

In some embodiments of the method, the amino donor comprises a compound of Formula II, as described herein. In some embodiments of the method, the amino donor is selected from isopropylamine (2-amino propane), α-phenethylamine, D-alanine, L-alanine, or D,L-alanine, particularly isopropylamine.

In the methods, any of the engineered transaminase described herein can be used to convert the amine acceptor in presence of an amino donor to produce the chiral amine. In some embodiments, the engineered transaminases used in the method comprises an amino acid sequence that is at least 80%, 85%, 90%, 91%, 92%, 93%, 94%, 95%, 96%, 97%, 98%, 99% or more identical to the sequence of SEQ ID NO: 10, 16, or 18. These engineered transaminases can have one or more of improved properties, including among others, thermostability, solvent stability, isopropylamine resistance, increased enzymatic activity, stereoselectivity, and/or substrate recognition/binding.

In some embodiments of the method, the engineered transaminases can have one or more residue differences as compared to the naturally occurring transaminase of SEQ ID NO:2 or an a reference engineered transaminase, such as SEQ ID NO:18, at the following residue positions: X4, X9, X12, X21, X30, X31, X44, X45, X, 56, X57, X81, X82, X85, X86, X95, X112, X113, X127, X147, X153, X157, X166, X177, X181, X208, X211, X228, X233, X253, X272, X294, X297, X302, X311, X314, X316, X317, X318, X319, X320, X321, X324, X385, X391, X398, X407, X408, X409, X415, X417, X418, X420, X431, X434, X438, X444, and X446.

Guidance in choosing an engineered transaminase for a specific amine acceptor substrate is provided in the descriptions herein, such as in Table 3 and Table 4, which shows the activities of various engineered transaminases for structurally different amino acceptor substrates. In some embodiments of the method, the engineered transaminase can comprise an amino acid sequence corresponding to SEQ ID NO: 4, 6, 8, 10, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, or 198.

In some embodiments of the method for enantiomeric enrichment of a chiral amine, additional quantities of the amino acceptor can be added (up to saturation) and/or the amino acceptor (ketone) formed can be continuously removed from the reaction mixture. Conversely, when the undesired chiral form of the amine is converted to the amino acceptor (ketone) byproduct and the desired chiral form is not, the latter can be readily isolated by conventional techniques. A partial separation can be effected by acidification, extraction with a hydrocarbon such as heptane to remove the ketone, rendering the aqueous phase basic, and re-extraction with a hydrocarbon such as heptane. When, on the other hand, both chiral forms of the amine are desired, the form which is converted to the ketone can be removed from the reaction mixture (or from the aqueous phase in a two phase mixture) and independently subjected to the action of an omega-transaminase in the presence of an amino donor to generate the same chiral form which was initially converted to the ketone.

As noted herein, the transaminases of the disclosure can be used to mediate the reverse reaction in Scheme 1, i.e., the conversion of the chiral amine of Formula III to the ketone of Formula I along with conversion of the ketone of Formula IV to the amine of Formula II. Stereospecific conversion of either the (R) or (S) chiral amine can be used for the chiral resolution of mixtures of (R) and (S) amines. Accordingly, in some embodiments, the process for chiral resolution can comprise contacting a mixture of (R) and (S) chiral amine of formula IIIa (e.g., a racemic mixture) with a stereospecific transaminase of the disclosure in presence of ketone of Formula IV,

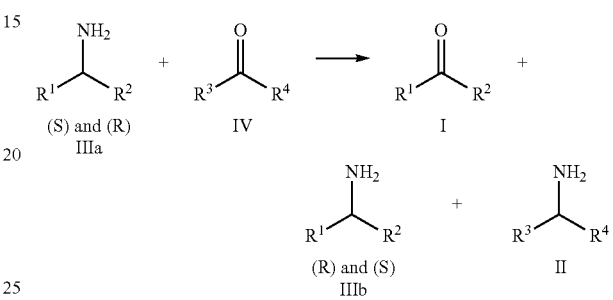

under suitable reaction conditions for formation of the ketone of Formula I and the amine of Formula II, thereby generating a mixture having a stereomeric excess of the chiral amine of Formula IIIb.

As is known by those of skill in the art, transamination reactions typically require a cofactor. Reactions catalyzed by the engineered transaminase enzymes described herein also typically require a cofactor, although many embodiments of the engineered transaminases require far less cofactor than reactions catalyzed with wild-type transaminase enzymes. As used herein, the term "cofactor" refers to a non-protein compound that operates in combination with a transaminase enzyme. Cofactors suitable for use with the engineered transaminase enzymes described herein include, but are not limited to, pyridoxal-5'-phosphate (also known as pyridoxal-phosphate, PLP, P5P). In some embodiments, the PLP cofactor is provided in the cell extract and does not need to be added. In some embodiments utilizing highly purified transaminase enzyme, the cofactor is added to the reaction mixture either at the beginning of the reaction or additional cofactor may be added during the reaction. In some embodiments, a different member of the vitamin $B_6$ family, such as pyridoxine, is used in place of PLP.

In some embodiments, the transaminase reactions can be carried in presence of reduced cofactor, nicotinamide adenine dinucleotide (NADH), which can limit the inactivation of the transaminase enzyme (see van Ophem et al., 1998, Biochemistry 37(9):2879-88). In some embodiments, a cofactor regeneration system, such as glucose dehydrogenase (GDH) and glucose or formate dehydrogease and formate can be used to regenerate NADH in the reaction medium.

The transamination reactions described herein are generally carried out in a solvent. Suitable solvents include water, organic solvents (e.g., ethanol, dimethyl sulfoxide (DMSO), ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems comprises water and one or more organic solvent. In general, an organic solvent component of an aqueous co-solvent system is selected such that it does not completely inactivate the transaminase enzyme. Appropriate co-solvent systems can be readily identified by measuring the enzymatic activity of the specified engineered transaminase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 1% to about 99% (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the transaminase reaction can be carried out at a pH of about 10 or below, usually in the range of from about 5 to about 10. In some embodiments, the transaminase reaction is carried out at a pH of about 9 or below, usually in the range of from about 5 to about 9. In some embodiments, the transaminase reaction is carried out at a pH of about 8 or below, often in the range of from about 5 to about 8, and usually in the range of from about 6 to about 8. The transaminase reaction may also be carried out at a pH of about 7.8 or below, or 7.5 or below. Alternatively, the transaminase reaction may be carried out a neutral pH, i.e., about 7.

During the course of the transamination reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

In carrying out the transamination reactions described herein, the engineered transaminase enzyme may be added to the reaction mixture in the form of the purified enzymes, whole cells transformed with gene(s) encoding the enzymes, and/or cell extracts and/or lysates of such cells. The gene(s) encoding the engineered transaminase enzymes can be transformed into host cells separately or together into the same host cell. For example, in some embodiments one set of host cells can be transformed with gene(s) encoding one engineered transaminase enzyme and another set can be transformed with gene(s) encoding another engineered transaminase. Both sets of transformed cells can be utilized together in the reaction mixture in the form of whole cells, or in the form of lysates or extracts derived therefrom. In other embodiments, a host cell can be transformed with gene(s) encoding multiple engineered transaminase enzymes. In some embodiments the engineered polypeptides can be expressed in the form of secreted polypeptides and the culture medium containing the secreted polypeptides can be used for the transaminase reaction.

Whole cells transformed with gene(s) encoding the engineered transaminase enzyme or cell extracts, lysates thereof, and isolated enzymes may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum.

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production. In general, the transaminase substrates are kept at levels that achieve essentially complete or near complete conversion of the substrates into products.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

For improved mixing efficiency when an aqueous co-solvent system is used, the transaminase, and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase Suitable conditions for carrying out the transaminase-catalyzed transamination reactions described herein include a wide variety of conditions which can be readily optimized by routine experimentation that includes, but is not limited to, contacting the engineered transaminase enzyme and substrate at an experimental pH and temperature and detecting product, for example, using the methods described in the Examples provided herein.

The transaminase catalyzed reaction is typically carried out at a temperature in the range of from about 15° C. to about 60° C. For some embodiments, the reaction is carried out at a temperature in the range of from about 20° C. to about 55° C. For some embodiments, the reaction is carried out at a temperature in the range of from about 35° C. to about 50° C. In still other embodiments, it is carried out at a temperature in the range of from about 40° C. to about 50° C. The reaction may also be carried out under ambient conditions.

The transamination reaction is generally allowed to proceed until essentially complete, or near complete, transformation of substrate is obtained. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and are often greater than about 97%.

7. EXAMPLES

Various features and embodiments of the disclosure are illustrated in the following representative examples, which are intended to be illustrative, and not limiting.

Example 1

Screen for Thermostable Transaminase Variants Using Isopropylamine as Amine-Donor The following method was used to screen transaminase libraries for a thermostable backbone from which most polypeptide variants were evolved. Biotransformations were performed in 96-well plates and contained the following: 1.0 M isopropylamine (pH 7.5) and 1.0 M pyruvate in 100 mM triethanolamine hydrochloride buffer (pH 7.5). The amine product (alanine) was then converted to its corresponding isoindole product using o-phthaldialdehyde/N-acetylcysteine reagent (OPA), separated by HPLC, and quantified using external standards.

Reagents, per well:

| Component | Volume/Well | Final conc. |
|---|---|---|
| Pyruvate, pH 7.5 (2.5M) | 80 μL | 1.0M |
| IPM (5.0M, pH 7.5) | 40 μL | 1.0M |
| 1.0M TEA, pH 7.5 | 20 μL | 100 mM |
| Water | 20 μL | |
| Lysate | 40 μL | |

200 μL/well final volume.

Biotransformations. Lysate containing transaminase variants was added to 96-well round bottom plates (40 μL/well). The plates were heat-sealed and incubated at 50° C. for 24 h. After 24 h at 50° C., reactions were initiated by addition of a 160 mL/well of a 50° C. pre-heated solution of 1.25 M pyruvate, 1.25 M isopropylamine, and 125 mM triethanolamine (pH 7.5). The reactions were briefly agitated, heat sealed, and returned to the 50° C. incubator. After 2 h, 10 mL/well biotransformation was transferred to a 96-well plate containing 190 mL/well aqueous 0.5 mM hydroxylamine. This hydroxylamine-quenched plate was heat-sealed and stored in a 4° C. refrigerator for later analysis. The reaction plate was heat-sealed and returned to the 50° C. incubator. After 24 h total reaction time, another 10 mL/well aliquot of biotransformation was added to a new 96-well plate containing 190 mL/well 0.5 mM hydroxylamine. The quenched biotransformations (both the 2 h and the 24 h timepoints) were then OPA derivatized and analyzed by HPLC. Quantification of alanine was performed as follows:

1. 20 μL/well quenched biotransformation was transferred to an empty 96-well plate.
2. Six standards containing mixtures of known amounts of isopropylamine and alanine (50 mM total amine concentration) were prepared and 20 μL of each standard was added to a second 96-well plate.
3. Both the quenched biotransformation plate and the standards plate were transferred to an HPLC equipped with an autosampler.
4. On-line OPA derivatization of each sample to the corresponding isoindole product was performed immediately prior to HPLC analysis by automated addition of 80 μL OPA derivatization reagent to each 20 μL aliquot.
5. The isoindole products were separated by HPLC and detected by absorbance at 320 nm.
6. Peak areas of the standards were used to generate a calibration curve.
7. Alanine product concentrations were calculated from the calibration curve and accounted for dilution steps.

Example 2

Generation of Highly Expressed *Vibrio Fluvialis* Transaminase Variants

A gene encoding the wild-type omega transaminase from *Vibrio fluvialis* SEQ ID NO:1 based on the reported amino acid sequence (Kim and/or Shin) was synthesized and cloned into an in-house pCK110900 vector system (United States Patent Application Publication 20060195947) and subsequently expressed in *E. coli* W3110fhuA. Two random mutagenesis libraries were generated, with individual colonies grown in 96-well plates. Crude lysate from the cells was then used to screen for increased activity. Screening conditions were as follows: 1.0 M isopropylamine and 110 mM pyruvate in 100 mM triethanolamine buffer (pH 9) at 50° C. for 4-4.5 h. Reactions were quenched by addition of 0.5 mM aqueous hydroxylamine hydrochloride and then analyzed by HPLC. Variants that produced significantly higher yields of the product (L-alanine) were sequenced and analyzed by SDS-PAGE, revealing that N-terminal mutations, both coding and non-coding (up to and including the $12^{th}$ residue), are capable of greatly increasing expression levels.

TABLE 5

| Nuc ID | Amino Acid Sequence Changes | Silent mutations | Expression Level |
|---|---|---|---|
| 193 | E12K; E302K | g309t | +++++ |
| 3 | | c18t; c286t | +++++ |
| 5 | A9T | c852t; g861a | +++ |
| 7 | P4R | g891c | +++++ |
| 11 | A9T; F86Y; M294V; | c852t; g861a | +++++ |
| 13 | | g12a; g15a; c18t | +++++ |
| 195 | S6R; A133T; Y184F; P252Q; I314F | t561c | +++ |
| 197 | S6I | | +++++ |

+++: 1-5x increase over wt
++++: 5-10x increase over wt
+++++: 10-20x increase over wt

Example 3

Amination of Ethyl 3-Oxobutanoate Using Isopropylamine as Amine-Donor

The following example describes the conditions for performing the following reaction:

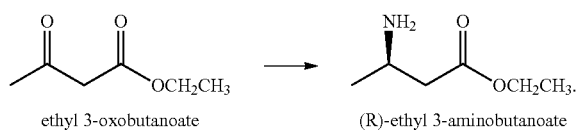

ethyl 3-oxobutanoate → (R)-ethyl 3-aminobutanoate

A high-throughput method was used to screen transaminase libraries for polypeptide variants using isopropylamine as the amine-donor. Biotransformations were performed in 96-well plates and contained the following: 50 mM isopropylamine (pH 7.0) and 50 mM ethyl 3-oxobutanoate in 100 mM triethanolamine hydrochloride buffer (pH 7.0) containing 5% ethanol Amine products were converted to their corresponding isoindole products using o-phthaldialdehyde/N-acetylcysteine reagent (OPA), separated by HPLC, and quantified using external standards.

Biotransformations were initiated by addition of 70 μL lysate containing 100 μM PLP to 30 μL "reaction mixture." Reaction mixture consisted of 167 mM isopropylamine (pH 7.0) and 167 mM ethyl 3-oxobutanoate in 333 mM triethanolamine buffer (pH 7.0) containing 16.7% ethanol. Biotransformations were agitated at room temperature for 17 h and then quenched by addition of 0.1 volume of 1.5 mM aqueous hydroxylamine hydrochloride.

Quantification of ethyl 3-aminobutanoate was performed as follows:

1. 20 μL/well quenched biotransformation was transferred to an empty 96-well plate.
2. Six standards containing mixtures of known amounts of isopropylamine and ethyl 3-aminobutanoate (50 mM total amine concentration) were prepared and 20 μL of each standard was added to a second 96-well plate.
3. Both the quenched biotransformation plate and the standards plate were transferred to an HPLC equipped with an autosampler.
4. On-line OPA derivatization of each sample to the corresponding isoindole product was performed immediately prior to HPLC analysis by automated addition of 80 μL OPA derivatization reagent to each 20 μL aliquot.
5. The isoindole products were separated by HPLC and detected by absorbance at 320 nm.
6. Peak areas of the standards were used to generate a calibration curve.
7. ethyl 3-aminobutanoate product concentrations were calculated from the calibration curve and accounted for dilution steps.

The procedure in this example was also used to screen transaminase libraries with 3,4-dihydronaphthalen-1(2H)-one, 1-phenylbutan-2-one, 2-methylcyclohexanone, and 1-(4-bromophenyl)ethanone as the amino acceptor.

Example 4

Amination of Octan-2-One Using Isopropylamine as Amine-Donor

The following example describes the conditions for performing the following reaction:

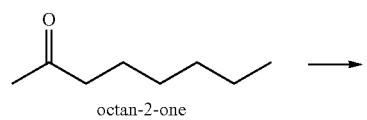

octan-2-one →

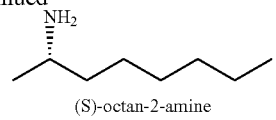

(S)-octan-2-amine

The following high-throughput method was used to screen transaminase libraries for variants using isopropylamine as the amine-donor. Biotransformations were performed in 96-well plates and contained the following: 200 mM isopropylamine (pH 7.0) and 100 mM octan-2-one in 100 mM triethanolamine hydrochloride buffer (pH 7.0) containing 5% ethanol. Amine products were converted to their corresponding isoindole products using o-phthaldialdehyde/N-acetylcysteine reagent (OPA), separated by HPLC, and quantified using external standards.

Biotransformations were initiated by addition of 80 μL lysate containing 100 μM PLP to 20 μL "reaction mixture." Reaction mixture consisted of 1.0 M isopropylamine (pH 7.0) and 500 mM octan-2-one in 500 mM triethanolamine buffer (pH 7.0) containing 25% ethanol. Biotransformations were agitated at room temperature for 17 h and then quenched by addition of 3 volumes of 0.5 mM aqueous hydroxylamine hydrochloride.

Quantification of octan-2-amine was performed as follows:

1. 20 μL/well quenched biotransformation was transferred to an empty 96-well plate.
2. Six standards containing mixtures of known amounts of isopropylamine and octan-2-amine (50 mM total amine concentration) were prepared and 20 μL of each standard was added to a second 96-well plate.
3. Both the quenched biotransformation plate and the standards plate were transferred to an HPLC equipped with an autosampler.
4. On-line OPA derivatization of each sample to the corresponding isoindole product was performed immediately prior to HPLC analysis by automated addition of 80 μL OPA derivatization reagent to each 20 μL aliquot.
5. The isoindole products were separated by HPLC and detected by absorbance at 320 nm.
6. Peak areas of the standards were used to generate a calibration curve.
7. Octan-2-amine product concentrations were calculated from the calibration curve and accounted for dilution steps.

Example 5

Amination of 3,3-dimethylbutan-2-one Using Isopropylamine as Amine-Donor

The following example describes the conditions for performing the following reaction,

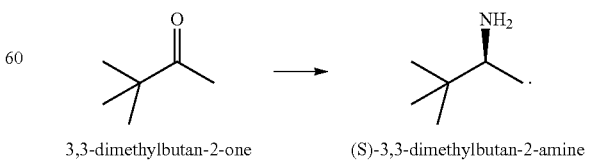

3,3-dimethylbutan-2-one → (S)-3,3-dimethylbutan-2-amine

The following high-throughput method was used to screen transaminase libraries for polypeptide variants using isopropylamine as the amine-donor. Biotransformations were performed in 96-well plates and contained the following: 200 mM isopropylamine (pH 7.0) and 100 mM 3,3-dimethylbutan-2-one in 100 mM triethanolamine hydrochloride buffer (pH 7.0) containing 5% ethanol Amine products were converted to their corresponding isoindole products using o-phthaldialdehyde/N-acetylcysteine reagent (OPA), separated by HPLC, and quantified using external standards.

Biotransformations were initiated by addition of 40 µL lysate containing 100 µM PLP to 60 µL "reaction mixture." Reaction mixture consisted of 333 mM isopropylamine (pH 7.0) and 167 mM 3,3-dimethylbutan-2-one in 167 mM triethanolamine buffer (pH 7.0) containing 8.3% ethanol. Biotransformations were agitated at room temperature for 17 h and then quenched by addition of 3 volumes of 0.5 mM aqueous hydroxylamine hydrochloride.

Quantification of 3,3-dimethylbutan-2-amine was performed as follows:
1. 20 µL/well quenched biotransformation was transferred to an empty 96-well plate.
2. Six standards containing mixtures of known amounts of isopropylamine and 3,3-dimethylbutan-2-amine (50 mM total amine concentration) were prepared and 20 µL of each standard was added to a second 96-well plate.
3. Both the quenched biotransformation plate and the standards plate were transferred to an HPLC equipped with an autosampler.
4. On-line OPA derivatization of each sample to the corresponding isoindole product was performed immediately prior to HPLC analysis by automated addition of 80 µL OPA derivatization reagent to each 20 µL aliquot.
5. The isoindole products were separated by HPLC and detected by absorbance at 320 nm.
6. Peak areas of the standards were used to generate a calibration curve.
7. 3,3-dimethylbutan-2-amine product concentrations were calculated from the calibration curve and accounted for dilution steps.

The procedure in this example was also used to screen transaminase libraries with 4-phenylbutan-2-one as the amino acceptor.

Example 6

Amination of 1-(6-methoxynapthalene-2-yl)ethanone to its Corresponding S-Amine

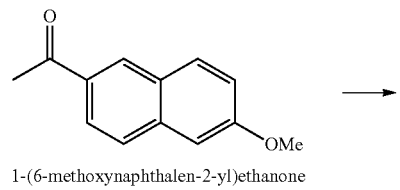

1-(6-methoxynaphthalen-2-yl)ethanone

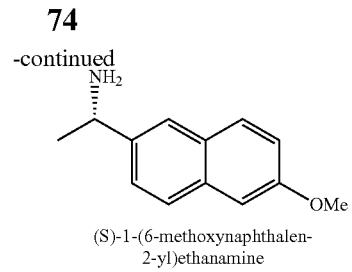

(S)-1-(6-methoxynaphthalen-2-yl)ethanamine

Reaction Conditions and Analysis: Transaminase variants were assayed for conversion of the ketone substrate 1-(6-methoxynapthalene-2-yl)ethanone to its corresponding amine product (S)-1-(6-methoxynapthalene-2-yl) ethanamine according to the following reaction conditions: 1 mg/mL (or 6.25 mg/mL) ketone substrate, 0.5 mg/mL PLP, 0.5 mg/mL NAD, 0.1 mg/mL lactate dehydrogenase (LDH), 1 mg/mL formate dehydrogenase (FDH), 90 mg/mL L-alanine, 40 mg/mL formate, 5 vol % DMSO, buffer pH 7.5. The reaction mixture was allowed to react for 24 h with shaking at 30° C. Alternatively, GDH and glucose can replace FDH and formate for recycling NAD co-factor. Typical concentrations are as follows: 1 mg/mL GDH, 90 mg/mL glucose.

Additionally, a subset of variants were screened under the same conditions except using isopropylamine (iPr-NH$_2$) rather than L-alanine as the amine donor for the reaction according to the following conditions: 1 mg/mL (or 5 mg/mL) ketone substrate, 0.5 mg/mL PLP, 1 M iPr-NH2, 5-40 vol % DMSO in 100 mM triethanolamine buffer, pH 7.5 or 8.5. The reaction mixture was allowed to react for 24 h at 30° C.

Following the reaction, the mixture is extracted into an organic solvent phase (e.g., ethyl acetate, propyl acetate or methyl t-butyl ether) and analyzed by HPLC. Percent conversion is calculated based on peak areas as the ratio of amine product peak area to (ketone substrate peak area+ amine product peak area).

As shown by the results listed in Table 6, reactions using alanine as amine donor resulted in substantially higher conversion than reactions using isopropylamine as donor. Reactions with alanine as donor and 1.0 mg/mL substrate loading were able to convert up to 21.3% of the substrate-(6-methoxynapthalene-2-yl)ethanone to its corresponding amine product.

At least the following residue differences are associated with the ability to convert at least 2.0% substrate to its corresponding amine product: W57A/C/F/I/L/S, Y86A/F/G/H/S, V153A/C/Q/S, P233L/T, F317L, P318F/G/R, G320A, F321L, L417A/S/T/V, and F438L.

TABLE 6

| SEQ ID NO: | Residue differences (as compared to SEQ ID NO: 18) | iPr—NH$_2$ donor | 1.0 mg/mL substrate (alanine donor) | 6.25 mg/mL substrate (alanine donor) |
|---|---|---|---|---|
| 126 | W57L; Y86F; V153S; P233T; L417T | +++ | +++++ | ++++ |
| 154 | W57C; Y86S; L417T | +++ | +++++ | ++++ |
| 134 | W57S; P233L; L417V | | +++++ | ++++ |
| 140 | W57A; V153S; P318G | ++ | +++++ | +++++ |

TABLE 6-continued

| SEQ ID NO: | Residue differences (as compared to SEQ ID NO: 18) | iPr—NH$_2$ donor | 1.0 mg/mL substrate (alanine donor) | 6.25 mg/mL substrate (alanine donor) |
|---|---|---|---|---|
| 148 | W57A; V153C; F321L | | +++++ | ++++ |
| 178 | W57L; Y86S; V153A | ++ | +++++ | +++ |
| 136 | W57S; Y86G; L417C | | +++++ | ++++ |
| 180 | W57L; Y86F; P318F | ++ | +++++ | ++++ |
| 146 | W57F; Y86F; V153Q | ++ | ++++ | ++++ |
| 144 | W57I; Y86F; G320A | + | ++++ | +++ |
| 166 | W57C; Y86A; F317L | | ++++ | +++ |
| 114 | W57L; L417C; F438L | ++ | +++ | +++ |
| 150 | Y86F; P318R; L417A | | +++ | +++ |
| 142 | W57F; Y86H; V153Q | | +++ | +++ |
| 174 | W57F; P318F; L417S | | +++ | ++ |
| 110 | Y86H; V153S; C181R; L417T | ++ | +++ | ++ |
| 172 | V153S; F317L; L417C | + | +++ | ++ |
| 190 | V153T; A228G; L417A | | +++ | ++ |
| 116 | W57F; M127L; L417C | | +++ | ++ |
| 138 | A228G; F317L; L417C | | +++ | ++ |
| 184 | P233L; F321L; L417I | | +++ | |
| 152 | A228G; P318G; L417C | | +++ | ++ |
| 28 | W57L | ++ | +++ | +++ |
| 86 | L417C | + | +++ | + |
| 92 | Y86H; V153S; L417C | ++ | +++ | + |
| 162 | Y86H; P233L; L417A | | +++ | ++ |
| 48 | Y86S; V153S | | ++ | + |
| 156 | Y86F; V153C; V297A | ++ | ++ | ++ |
| 182 | V153S; A228G; L417V | | ++ | |
| 192 | W57F; P318G; L417I | | ++ | |
| 78 | L417A | | ++ | + |
| 26 | Y86F | | ++ | |
| 84 | L417I | | ++ | |
| 170 | V153T; A228G; F321L | | ++ | |
| 186 | F317L; P318R; L417T | | ++ | |
| 188 | V153C; F317Y; H319Q | | ++ | |
| 24 | Y86N | | + | |
| 46 | W57I; V153S | + | + | + |
| 88 | Y86H; V153A; L417C | | + | |
| 102 | V153A; P233T; L417C | | + | |
| 108 | M95T; V153A; L417C | | + | |
| 168 | Y86N; A228G; F317L | | + | |
| 158 | Y86S; V153T; V297A | | + | |

+ ≥0.2%
++ ≥0.5%
+++ ≥1.0%
++++ ≥5.0%
+++++ ≥10.0%

Example 7

Transaminase Variants Capable of Converting Ketone Substrate 1-(2,3-dihydrobenzo[b][1.4]dioxin-6-yl)ethanone to its Corresponding S-Amine Product

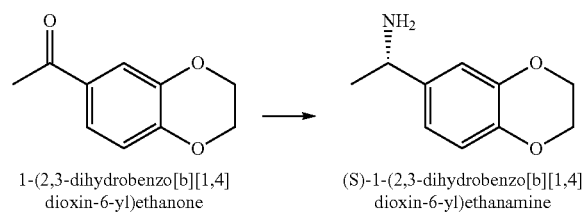

1-(2,3-dihydrobenzo[b][1,4] dioxin-6-yl)ethanone → (S)-1-(2,3-dihydrobenzo[b][1,4] dioxin-6-yl)ethanamine Reaction conditions and analysis: Transaminase variants were assayed for conversion of the ketone substrate 1-(2,3-dihydrobenzo[b][1.4]dioxin-6-yl)ethanone to its corresponding amine product (S)-1-(2,3-dihydrobenzo[b][1.4]dioxin-6-yl)ethanamine according to the following reaction conditions: 1 mg/mL ketone substrate, 0.5 mg/mL PLP, 0.5 mg/mL NAD, 0.1 mg/mL LDH, 1 mg/mL FDH, 90 mg/mL L-alanine, 40 mg/mL formate, 5 vol % DMSO, buffer pH 7.5. The reaction mixture was allowed to react for 24 h at 30° C.

Following the reaction, the mixture is extracted into an organic solvent phase (e.g., ethyl acetate, propyl acetate or methyl t-butyl ether) and analyzed by HPLC. Percent conversion is calculated based on peak areas as the ratio of amine product peak area to (ketone substrate peak area+ amine product peak area).

As shown by the results listed in Table 7, variants were able to convert up to 9.3% of ketone substrate 1-(2,3-dihydrobenzo[b][1.4]dioxin-6-yl)ethanone to its corresponding S-amine product. The positive control fluvialis TA of SEQ ID NO:18 exhibited only 0.7% conversion.

At least the following residue differences are associated with the ability to convert at least 2.0% substrate of formula (2) to its corresponding amine product: W57A/C/F/I/L/S, Y86F/G/S, V153A/C/Q/S, A228G, P233L/T, V297A, P318F/G, G320A, L417C/T/V, and F438L.

TABLE 7

| SEQ ID NO: | Residue Differences (as compared to SEQ ID NO: 18) | Conv. (%) |
|---|---|---|
| 152 | W57C; Y86S; L417T | +++ |
| 146 | W57F; Y86F; V153Q | +++ |
| 126 | W57L; Y86F; V153S; P233T; L417T | +++ |
| 156 | Y86F; V153C; V297A | ++ |
| 28 | W57L | ++ |
| 114 | W57L; L417C; F438L | ++ |
| 134 | W57S; P233L; L417V | ++ |
| 178 | W57L; Y86S; V153A | ++ |
| 136 | W57S; Y86G; L417C | ++ |
| 140 | W57A; V153S; P318G | ++ |
| 42 | W57I | ++ |
| 46 | W57I; V153S | ++ |
| 144 | W57I; Y86F; G320A | ++ |
| 180 | W57L; Y86F; P318F | ++ |
| 182 | V153S; A228G; L417V | ++ |
| 26 | Y86F | ++ |
| 166 | W57C; Y86A; F317L | + |
| 104 | V153S; P233S | + |
| 148 | W57A; V153C; F321L | + |
| 72 | V153G | + |
| 48 | Y86S; V153S | + |
| 84 | L417I | + |
| 110 | Y86H; V153S; C181R; L417T | + |
| 16 | D21N; H45N; L177V; T208I; K211R; G324S; A391T | + |
| 44 | V153S | + |
| 98 | V31A | + |
| 106 | Y86H; V153A; A228G; L417I | + |
| 164 | V153C; P233L; P318R | + |

+ ≥0.8%
++ ≥2.0%
+++ ≥5.0%

Example 8

Transaminase Variants Capable of Converting Ketone Substrate 1-(4-phenoxyphenyl)ethanone to its Corresponding S-Amine Product

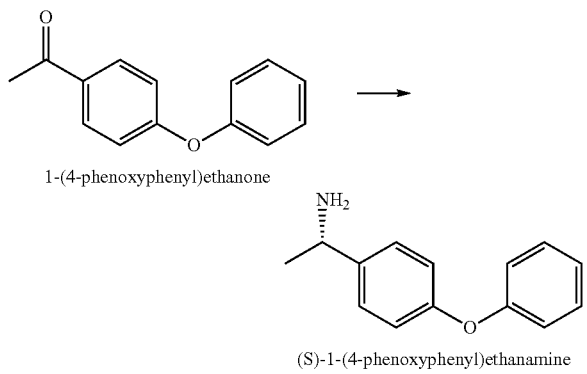

1-(4-phenoxyphenyl)ethanone (S)-1-(4-phenoxyphenyl)ethanamine

Reaction conditions and analysis for conversion of ketone substrate: Transaminase variants were assayed for conversion of the ketone substrate 1-(4-phenoxyphenyl)ethanone to its corresponding amine product (S)-1-(4-phenoxyphenyl)ethanamine according to the following reaction conditions: 1 mg/mL ketone substrate, 0.5 mg/mL PLP, 0.5 mg/mL NAD, 0.1 mg/mL LDH, 1 mg/mL FDH, 90 mg/mL L-alanine, 40 mg/mL formate, 5 vol % DMSO, buffer pH 7.5. The reaction mixture was allowed to react for 24 h at 30° C. Following the reaction, the mixture is extracted into an organic solvent phase (e.g., ethyl acetate, propyl acetate or methyl t-butyl ether) and analyzed by HPLC. Percent conversion is calculated based on peak areas as the ratio of amine product peak area to (ketone substrate peak area+amine product peak area).

As shown by the results listed in Table 8, variants were able to convert up to 2.0% of ketone substrate 1-(4-phenoxyphenyl)ethanone to its corresponding S-amine product. The positive control *fluvialis* TA of SEQ ID NO:18 exhibited no detectable conversion under the assay conditions.

At least the following residue differences are associated with the ability to convert at least 0.5% substrate of formula (3) to its corresponding amine product: W57C/F/I/L, Y86H/F/S, V153A/C/Q/S, C181R, P233T, V297A, P318F, L417C/T, and F438L.

TABLE 8

| SEQ ID NO: | Residue Differences (as compared to SEQ ID NO: 18) | Conv. (%) |
|---|---|---|
| 16 | D21N; H45N; L177V; T208I; K211R; G324S; A391T | + |
| 20 | Y86S | + |
| 26 | Y86F | + |
| 28 | W57L | ++ |
| 42 | W57I | + |
| 44 | V153S | + |
| 46 | W57I; V153S | + |
| 48 | Y86S; V153S | + |
| 72 | V153G | + |
| 78 | L417A | + |
| 84 | L417I | + |
| 88 | Y86H; V153A; L417C | + |
| 90 | Y86H; V153A | + |
| 92 | Y86H; V153S; L417C | + |
| 98 | V31A | + |
| 104 | V153S; P233S | + |
| 106 | Y86H; V153A; A228G; L417I | + |
| 108 | M95T; V153A; L417C | + |
| 110 | Y86H; V153S; C181R; L417T | + |
| 114 | W57L; L417C; F438L | + |
| 126 | W57L; Y86F; V153S; P233T; L417T | ++ |
| 134 | W57S; P233L; L417V | + |
| 136 | W57S; Y86G; L417C | + |
| 140 | W57A; V153S; P318G | + |
| 142 | W57F; Y86H; V153Q | + |
| 144 | W57I; Y86F; G320A | + |
| 146 | W57F; Y86F; V153Q | ++ |
| 154 | W57C; Y86S; L417T | ++ |
| 156 | Y86F; V153C; V297A | ++ |
| 162 | Y86H; P233L; L417A | + |
| 164 | V153C; P233L; P318R | + |
| 166 | W57C; Y86A; F317L | + |
| 178 | W57L; Y86S; V153A | ++ |
| 180 | W57L; Y86F; P318F | + |
| 182 | V153S; A228G; L417V | + |
| 190 | V153T; A228G; L417A | + |

+ ≥0.2%
++ ≥1.0%

Example 9

Transaminase Variants Capable of Converting Ketone Substrate (R)-4-oxotetrahydro-2H-pyran-3-yl Benzoate to its Corresponding S-Amine Product

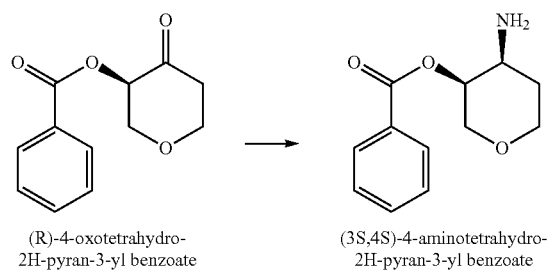 [SMILES: O=C(O[C@@H]1COCCC1=O)c1ccccc1 ; N[C@H]1CCOC[C@H]1OC(=O)c1ccccc1]

(R)-4-oxotetrahydro-2H-pyran-3-yl benzoate → (3S,4S)-4-aminotetrahydro-2H-pyran-3-yl benzoate Reaction conditions and analysis: Transaminase variants were assayed for conversion of the ketone substrate (R)-4-oxotetrahydro-2H-pyran-3-yl benzoate to its corresponding amine product (3S,4S)-4-aminotetrahydro-2H-pyran-3-yl benzoate according to the following reaction conditions: 1 mg/mL ketone substrate, 0.5 mg/mL PLP, 0.5 mg/mL NAD, 0.1 mg/mL LDH, 1 mg/mL FDH, 90 mg/mL L-alanine, 40 mg/mL formate, 5 vol % DMSO, buffer pH 7.5. The reaction mixture was allowed to react for 24 h at 30° C.

Following the reaction, the mixture is extracted into an organic solvent phase (e.g., ethyl acetate, propyl acetate or methyl t-butyl ether) and analyzed by HPLC. Percent conversion is calculated based on peak areas as the ratio of amine product peak area to (ketone substrate peak area+ amine product peak area).

As shown by the results listed in Table 9, variants were able to convert up to 57% of ketone substrate (R)-4-oxotetrahydro-2H-pyran-3-yl benzoate to its corresponding S-amine product. The positive control *fluvialis* TA of SEQ ID NO:18 exhibited no detectable conversion.

At least the following residue differences are associated with the ability to convert at least 1% substrate (R)-4-oxotetrahydro-2H-pyran-3-yl benzoate to its corresponding S-amine product: W57A/C/I/L/S, Y86A/F/G/S, V153C/S, P233T, F317L, P318G, G320A, F321L, and L417T.

TABLE 9

| SEQ ID NO: | Residue Differences (as compared to SEQ ID NO: 18) | % Conversion |
|---|---|---|
| 140 | W57A; V153S; P318G | +++ |
| 148 | W57A; V153C; F321L | +++ |
| 178 | W57L; Y86S; V153A | ++ |
| 144 | W57I; Y86F; G320A | ++ |
| 136 | W57S; Y86G; L417C | ++ |
| 126 | W57L; Y86F; V153S; P233T; L417T | ++ |
| 154 | W57C; Y86S; L417T | ++ |
| 166 | W57C; Y86A; F317L | ++ |
| 46 | W57I; V153S | + |

+ ≥1%
++ ≥5%
+++ ≥50%

Example 10

Transaminase Variants Capable of Converting Ketone Substrate (R)-3-(benzyloxy)dihydro-2H-pyran-4(3H)-one to its Corresponding S-Amine Product

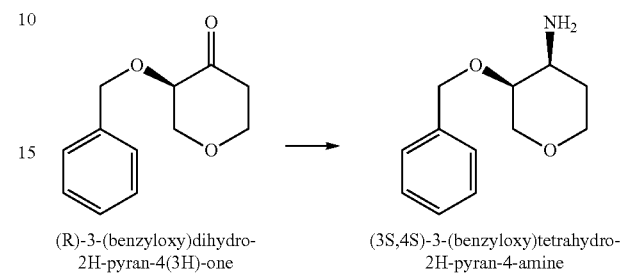

(R)-3-(benzyloxy)dihydro-2H-pyran-4(3H)-one → (3S,4S)-3-(benzyloxy)tetrahydro-2H-pyran-4-amine Reaction conditions and analysis: Transaminase variants were assayed for conversion of the ketone substrate (R)-3-(benzyloxy)dihydro-2H-pyran-4(3H)-one to its corresponding amine product (3S4S)-3-(benzyloxy)tetrahydro-2H-pyran-4-amine according to the following reaction conditions: 1 mg/mL ketone substrate, 0.5 mg/mL PLP, 0.5 mg/mL NAD, 0.1 mg/mL LDH, 1 mg/mL FDH, 90 mg/mL L-alanine, 40 mg/mL formate, 5 vol % DMSO, buffer pH 7.5. The reaction mixture was allowed to react for 24 h at 30° C.

Following the reaction, the mixture is extracted into an organic solvent phase (e.g., ethyl acetate, propyl acetate or methyl t-butyl ether) and analyzed by HPLC. Percent conversion is calculated based on peak areas as the ratio of amine product peak area to (ketone substrate peak area+ amine product peak area).

As shown by the results listed in Table 10, variants were able to convert up to 100% of ketone substrate (R)-3-(benzyloxy)dihydro-2H-pyran-4(3H)-one to its corresponding amine product. The positive control *fluvialis* TA of SEQ ID NO:18 exhibited only 9% conversion.

At least the following residue differences are associated with the ability to convert at least 90% substrate (R)-3-(benzyloxy)dihydro-2H-pyran-4(3H)-one to its corresponding S-amine product: W57F/I/S; G81D; F85S; Y86F/G/H/N; M127L; V153C/Q/S; A228G; V297A; F317L; P318F/R; L417A/CN; and F438L.

TABLE 10

| SEQ ID NO: | Residue Differences (as compared to SEQ ID NO: 18) | % Conversion |
|---|---|---|
| 42 | W57I | ++++ |
| 46 | W57I; V153S | ++++ |
| 92 | Y86H; V153S; L417C | ++++ |
| 116 | W57F; M127L; L417C | ++++ |
| 126 | W57L; Y86F; V153S; P233T; L417T | ++++ |
| 134 | W57S; P233L; L417V | ++++ |
| 136 | W57S; Y86G; L417C | ++++ |
| 140 | W57A; V153S; P318G | ++++ |
| 148 | W57A; V153C; F321L | ++++ |
| 154 | W57C; Y86S; L417T | ++++ |
| 166 | W57C; Y86A; F317L | ++++ |
| 178 | W57L; Y86S; V153A | ++++ |
| 180 | W57L; Y86F; P318F | ++++ |
| 28 | W57L | ++++ |
| 144 | W57I; Y86F; G320A | ++++ |
| 114 | W57L; L417C; F438L | ++++ |

TABLE 10-continued

| SEQ ID NO: | Residue Differences (as compared to SEQ ID NO: 18) | % Conversion |
|---|---|---|
| 22 | G81D; Y86H | ++++ |
| 146 | W57F; Y86F; V153Q | +++ |
| 192 | W57F; P318G; L417I | +++ |
| 110 | Y86H; V153S; C181R; L417T | +++ |
| 106 | Y86H; V153A; A228G; L417I | +++ |
| 156 | Y86F; V153C; V297A | +++ |
| 172 | V153S; F317L; L417C | +++ |
| 174 | W57F; P318F; L417S | +++ |
| 142 | W57F; Y86H; V153Q | +++ |
| 190 | V153T; A228G; L417A | +++ |
| 186 | F317L; P318R; L417T | +++ |
| 90 | Y86H; V153A | +++ |
| 176 | V153T; H319V; L417I | +++ |
| 182 | V153S; A228G; L417V | +++ |
| 48 | Y86S; V153S | +++ |
| 108 | M95T; V153A; L417C | +++ |
| 88 | Y86H; V153A; L417C | +++ |
| 128 | F85S; V153A; P233T | +++ |
| 150 | Y86F; P318R; L417A | +++ |
| 98 | V31A | +++ |
| 130 | W57I; F85A; Y86H; L417C | +++ |
| 138 | A228G; F317L; L417C | +++ |
| 36 | F85S; V153A | +++ |
| 26 | Y86F | +++ |
| 158 | Y86S; V153T; V297A | +++ |
| 162 | Y86H; P233L; L417A | ++ |
| 102 | V153A; P233T; L417C | ++ |
| 122 | F85A; W147G; V153A | ++ |
| 40 | F85A; V153A | ++ |
| 86 | L417C | ++ |
| 100 | I314V; D409G | ++ |
| 132 | F85A; V153S; L417S | ++ |
| 170 | V153T; A228G; F321L | ++ |
| 50 | P318G; T408A | ++ |
| 184 | P233L; F321L; L417I | ++ |
| 52 | Y82H | ++ |
| 78 | L417A | ++ |
| 188 | V153C; F317Y; H319Q | ++ |
| 94 | T30A | ++ |
| 164 | V153C; P233L; P318R | ++ |
| 34 | V153A; F317L; P318G | ++ |
| 96 | V44A; N166S | ++ |
| 152 | A228G; P318G; L417C | ++ |
| 44 | V153S | ++ |
| 72 | V153G | ++ |
| 104 | V153S; P233S | ++ |
| 84 | L417I | ++ |
| 70 | V153N | ++ |
| 68 | V153T | + |
| 160 | V153S; P318R; L417E | + |
| 168 | Y86N; A228G; F317L | + |
| 60 | F85T | + |
| 20 | Y86S | + |
| 118 | I311V; I314T | + |
| 30 | Y82H; L417F | + |
| 32 | F85A; F317L | + |
| 58 | F85S | + |
| 82 | G320A | + |
| 62 | F85A | + |
| 80 | H319Q | + |
| 74 | F317M | + |
| 76 | F317Y | + |
| 112 | Y113C; K385R; L417C | + |
| 38 | Y113H; C407S | + |
| 54 | E12G; M434V | + |
| 120 | F112I; F317L | + |

+ ≥10%
++ ≥20%
+++ ≥50%
++++ ≥90%

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered transaminase polypeptide, wherein said transaminase polypeptide comprises a polypeptide sequence at least 90% identical to SEQ ID NO: 2, and wherein the transaminase polypeptide comprises a substitution of X86Y.

2. The engineered transaminase polypeptide of claim 1, wherein said polypeptide has at least about 10% residual activity in the conversion of pyruvate to L-alanine in presence of amino donor isopropylamine after treatment of the polypeptide at 50° C. for 23 h.

3. The engineered transaminase polypeptide of claim 1, wherein the transaminase polypeptide further comprises at least one additional substitution at a residue position selected from: X4, X12, X21, X157, X208, X253, X272, X302, X316, X398, X418, X420, X431, X444, and X446.

4. The engineered transaminase polypeptide of claim 3, wherein the transaminase polypeptide sequence further comprises at least one substitution selected from: X4 is R, Q, or L; X12 is K; X21 is N; X45 is H; X157 is T; X177 is L; X208 is I; X211 is K; X253 is M; X272 is A; X294 is V; X302 is K; X316 is K; X324 is G; X391 is A; X398 is R; X418 is V; X420 is N; X431 is D; X444 is V; and X446 is V.

5. The engineered transaminase polypeptide of claim 1, wherein the transaminase polypeptide has increased transaminase activity as compared to SEQ ID NO: 2 for conversion of an amine acceptor substrate to the corresponding chiral amine product.

6. The engineered transaminase polypeptide of claim 5, wherein the transaminase polypeptide sequence further comprises at least one substitution selected from: X30 is A; X31 is A; X44 is A; X56 is V; X57 is, A, C, F, I, L, or S; X81 is D; X82 is H; X85 is A, C, S, N, T, G, or V; X95 is T; X112 is I; X113 is C or H; X127 is L; X147 is G; X153 is A, C, G, N, M, Q, S, or T; X166 is S; X181 is R; X208 is I; X228 is G or T; X233 is L, S, I, V, N, G, or T; V297 is A, S, T, I, M, Q, C, or G; X311 is V; X314 is T or V; X317 is L, M, or Y; X318 is G, F, C, K, W, or R; X319 is Q, G, M, N, or V, X320 is A or K; X321 is L, M, or I; X385 is R; X398 is R; X407 is S; X408 is A; X409 is G; X415 is M; X417 is A, C, E, F, I, N, Q, Y, S, T, or V; X420 is N; X434 is V; and X438 is L.

7. The engineered transaminase polypeptide of claim 5, wherein the transaminase polypeptide sequence further comprises at least one substitution set selected from: X12 is G and X434 is V; X44 is A and X166 is S; X57 is I and X153 is S; X82 is H and X417 is F; X85 is A and X317 is L; X85 is S and X153 is A; X85 is A and X153 is A; X85 is S and X153 is S; X112 is I and X317 is L; X113 is H and X407 is S; X153 is S and X233 is S; X311 is V and X314 is T; X314 is V and X409 is G; and X318 is G and X408 is A.

8. The engineered transaminase polypeptide of claim 5, wherein the transaminase polypeptide sequence further comprises at least one substitution set selected from: X57 is A, X153 is S and X318 is G; X57 is A, X153 is C and X321 is L; X57 is F, X318 is F and X417 is S; X57 is F, X318 is G and X417 is I; X57 is L, X417 is C and X438 is L; X57 is F, X127 is L and X417 is C; X57 is S, X233 is L and X417 is V; X85 is A, X147 is G and X153 is A; X85 is S, X153 is A and X233 is T; X85 is A, X153 is S and X417 is S; X95 is T, X153 is A and X417 is C; X113 is C, X385 is R and X417 is C; X153 is A, X317 is L and X318 is G; X153 is A, X233 is T and X417 is C; X153 is S, X318 is R and X417 is E; X153 is C, X233 is L and X318 is R; X153 is T, X228 is G and X321 is L; X153 is S, X317 is L and X417 is C; X153 is T, X319 is V and X417 is I; X153 is S, X228 is G and X417 is V; X153 is C, X317 is Y and X319 is Q; X153 is T, X228 is G and X417 is A; X228 is G, X317 is L and X417 is C; X228 is G, X318 is G and X417 is C; X233 is L, X321 is L and X417 is I; and X317 is L, X318 is R and X417 is T.

9. The engineered transaminase polypeptide of claim 5, wherein the transaminase polypeptide comprises the amino acid sequence of SEQ ID NO: 178.

10. The engineered transaminase polypeptide of claim 1, wherein the transaminase polypeptide converts an amine acceptor substrate to a corresponding amine product with improved R-enantioselectivity at a greater rate compared to the polypeptide set forth in SEQ ID NO: 18.

11. The engineered transaminase polypeptide of claim 10, wherein the transaminase polypeptide sequence further comprises at least one substitution selected from: X57 is L, X81 is D, X82 is H, X85 is A, C, N, T, or V; X95 is T; X112 is I; X147 is G; X153 is A, S, N, G, or T; X233 is S or T; X317 is L, X318 is G or R; and X319 is V.

12. The engineered transaminase polypeptide of claim 10, wherein the transaminase polypeptide sequence further comprises at least one substitution or substitution set selected from: X85 is A; X85 is A and X153 is A; and X85 is S and X153 is A.

13. The engineered transaminase polypeptide of claim 10, wherein the transaminase polypeptide sequence is SEQ ID NO: 104.

14. The engineered transaminase polypeptide of claim 1, wherein the transaminase enzyme polypeptide converts an amine acceptor substrate selected from 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, and 1-(4-bromophenyl)ethanone to the corresponding amine product at a rate that is greater than the polypeptide of SEQ ID NO: 2.

15. The engineered transaminase polypeptide of claim 14, wherein the transaminase polypeptide sequence comprises at least one additional substitution or substitution set selected from: X30 is A; X31 is A; X57 is I; X82 is H; X85 is V; X85 is C; X153 is S; X177 is L; X317 is M; X317 is Y; X417 is A; X319 is Q; X320 is A; X417 is I; X113 is H and X407 is S; X44 is A and X166 is S; X314 is V and X409 is G; X153 is S and X233 is S; X311 is V and X314 is T; X153 is S, X318 is R and X417 is E; X153 is C, X233 is L and X318 is R; X153 is S, X317 is L and X417 is C; X233 is L, X321 is L, and X417 is I; and X153 is C, X317 is Y and X319 is Q.

16. The engineered transaminase polypeptide of claim 14, wherein the transaminase polypeptide sequence is SEQ ID NO: 172.

17. The engineered transaminase polypeptide of claim 14, wherein the transaminase polypeptide converts the amine acceptor substrate 1-phenylbutan-2-one to the amine product (S)-1-phenylbutan-2-amine with improved S-enantioselectivity as compared to SEQ ID NO: 2.

* * * * *

SEQUENCE LISTING

<160> NUMBER OF SEQ ID NOS: 198

<210> SEQ ID NO 1
<211> LENGTH: 1362
<212> TYPE: DNA
<213> ORGANISM: Artificial Sequence
<220> FEATURE:
<223> OTHER INFORMATION: transaminase from V. fluvialis

<400> SEQUENCE: 1

```
atgaacaaac cgcagagctg ggaagcgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcgcctgtg gaacatggtg     180 gcgggctttg atcataaagg cctgattgat gcggcgaaag cgcagtatga acgttttccg     240
ggctatcatg cgtttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catgcgtga ccgcggtgag cgcgagcatg     480
accggcaaac cgtataacag cgtgtttggc ctgccgctgc cgggctttgt gcatctgacc     540
```

```
tgcccgcatt attggcgtta tggcgaagaa ggcgaaaccg aagaacagtt tgtggcgcgt      600
ctggcccgtg aactggaaga aaccattcag cgtgaaggcg cggataccat tgcgggcttt      660
tttgcggaac cggtgatggg tgcgggcggt gttattccgc cggcgaaagg ctatttcag       720 gcgattctgc cgatcctgcg caaatatgat attccggtga tcagcgatga agtgatttgc      780
ggctttggcc gtaccggcaa cacctggggc tgcgtgacct atgattttac cccggatgcg      840
attattagca gcaaaaacct gaccgcgggt ttttttccga tgggcgcggt gattctgggt      900
ccggaactga gcaaacgtct ggaaaccgcg attgaagcga tcgaagaatt ccgcatggt      960 tttaccgcga gcggccatcc ggtgggttgt gcgattgcgc tgaaagcgat tgatgtggtg     1020
atgaacgaag gcctggccga aaacgtgcgt cgtctggccc gcgttttga gaacgtctg      1080 aaacatattg cggaacgtcc gaacattggc gaatatcgtg cattggctt tatgtgggcg     1140 ctggaagcgg tgaaagataa agcgagcaaa accccgtttg atggcaacct gagcgtgagc     1200
gaacgtattg cgaacacctg caccgatctg ggcctgattt gcgtccgct gggccagagc     1260 gtggttctgt gcccgccgtt tattctgacc gaagcgcaga tggatgaaat gttcgataaa     1320
ctggaaaaag cgctggataa agtgtttgcg gaagtggcgt aa                        1362

<210> SEQ ID NO 2
<211> LENGTH: 453
<212> TYPE: PRT
<213> ORGANISM: Artificial Sequence
<220> FEATURE:
<223> OTHER INFORMATION: transaminase from V. fluvialis

<400> SEQUENCE: 2

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
```

```
                    210                 215                 220
Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Met Gly Ala Val Ile Leu Gly Pro Glu Leu Ser
                290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
                370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 3
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 3
atgaacaaac cgcagagttg ggaagcgcgt gcggaaacct atagcctgta tggctttacc        60
gatatgccga gcctgcatca gcgtggcacc gtggtggtga cccatggcga aggcccgtat       120
atcgtggatg tgaacggccg tcgttatctg gatgcgaaca gcggcctgtg gaacatggtg       180
gcgggctttg atcataaagg cctgattgat gcggcgaaag cgcagtatga acgttttccg       240
ggctatcatg cgtttttttgg ccgtatgagc gatcagaccg tgatgttgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac cgtataacag cgtgtttggc ctgccgctgc cgggctttgt gcatctgacc       540 tgccccgcatt attggcgtta tggcgaagaa ggcgaaaccg aagaacagtt gtgggcgcgt       600 ctggccgtg aactggaaga aaccattcag cgtgaaggcg cggataccat tgcgggcttt       660
```

```
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctgggc  tgcgtgacct atgattttac cccggatgcg    840
attattagca gcaaaaacct gaccgcgggt ttttttccga tgggcgcggt gattctgggt    900
ccggaactga gcaaacgtct ggaaaccgcg attgaagcga tcgaaaaatt tccgcatggt    960
tttaccgcga gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg cattggctt  tatgtgggcg   1140 ctggaagcgg tgaaagataa agcgagcaaa accccgtttg atggcaacct gagcgtgagc   1200
gaacgtattg cgaacacctg caccgatctg ggcctgattt gcgtccgct  gggccagagc   1260 gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 4
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 4

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240
```

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
        260                 265                 270

Thr Tyr Asp Phe Thr Pro Asp Ala Ile Ile Ser Ser Lys Asn Leu Thr
    275                 280                 285

Ala Gly Phe Phe Pro Met Gly Ala Val Ile Leu Gly Pro Glu Leu Ser
290                 295                 300

Lys Arg Leu Glu Thr Ala Ile Glu Ala Ile Glu Lys Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 5
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 5
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg aacatggtg     180 gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttgt gcatctgacc     540 tgccgcatt attggcgtta tggcgaagaa ggcgaaaccg aagaacagtt tgtggcgcgt     600
ctggcccgtg aactggaaga aaccattcag cgtgaaggcg cggataccat tgcgggcttt     660
tttgcggaac cggtgatggg tgcggcggt gttattccgc cggcgaaagg ctattttcag     720
gcgattctgc cgatcctgcg caaatatgat attccggtga tcagcgatga agtgatttgc     780
ggctttggcc gtaccggcaa cacctgggc tgcgtgacct atgatttac cccggatgcg     840

```
attattagca gtaaaaacct aaccgcgggt ttttttccga tgggcgcggt gattctgggt      900
ccggaactga gcaaacgtct ggaaaccgcg attgaagcga tcgaagaatt tccgcatggt      960
tttaccgcga gcggccatcc ggtgggttgt gcgattgcgc tgaaagcgat tgatgtggtg     1020
atgaacgaag gcctggccga aaacgtgcgt cgtctggccc gcgttttga agaacgtctg     1080 aaacatattg cggaacgtcc gaacattggc gaatatcgtg gcattggctt tatgtgggcg     1140
ctggaagcgg tgaaagataa agcgagcaaa accccgtttg atggcaacct gagcgtgagc     1200
gaacgtattg cgaacacctg caccgatctg ggcctgattt gccgtccgct gggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 6
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 6

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 7
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 7
atgaacaaac ggcagagctg ggaagcgcgt gcggaaacct atagcctgta tggctttacc        60
gatatgccga gcctgcatca gcgtggcacc gtggtggtga cccatggcga aggcccgtat       120
atcgtggatg tgaacggccg tcgttatctg gatgcgaaca gcggcctgtg aacatggtg       180 gcgggctttg atcataaagg cctgattgat gcggcgaaag cgcagtatga acgttttccg       240
ggctatcatg cgttttttgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac gtataacag cgtgtttggc ctgccgctgc cgggctttgt gcatctgacc       540 tgccgcatt attggcgtta tggcgaagaa ggcgaaaccg aagaacagtt tgtggcgcgt       600
ctggcccgtg aactggaaga aaccattcag cgtgaaggcg cggataccat tgcgggcttt       660
tttgcggaac cggtgatggg tgcggcggt gttattccgc ggcgaaagg ctattttcag       720 gcgattctgc cgatcctgcg caaatatgat attccggtga tcagcgatga agtgatttgc       780
ggctttggcc gtaccggcaa cacctggggc tgcgtgacct atgatttac cccggatgcg       840 attattagca gcaaaaacct gaccgcgggt tttttttccga tgggcgcggt cattctgggt       900
ccggaactga gcaaacgtct ggaaaccgcg attgaagcga tcgaagaatt tccgcatggt       960

```
tttaccgcga gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt atgtgggcg    1140 ctggaagcgg tgaaagataa agcgagcaaa accccgtttg atggcaacct gagcgtgagc    1200
gaacgtattg cgaacaccctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 8
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 8

```
Met Asn Lys Arg Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
```

290                 295                 300
Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                    340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 9
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 9
atgaacaaac cgcagagctg gaaaacgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gccgtttcga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttgt gcatctgacc     540
tgcccgcatt attggcgtta tggcgaagaa ggcgaaaccg aagaacagtt gtgtggcgcgt     600
ctggcccgtg aactggaaga accattcag cgtgaaggcg cggataccat tgcgggcttt     660
tttgcggaac cggtgatggg tgcggcggt gttattccgc cggcgaaagg ctatttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt ttttttccga tgggcgcggt gattctgggt     900
ccggaactga gcaaacgtct ggaaaccgcg attgaagcga tcgaagaatt tccgcatggt     960
tttaccgcga gcggccatcc ggtgggttgt gcgattgcgc tgaaagcgat tgatgtggtg    1020
atgaacgaag gcctgccgga aaacgtgcgt cgtctggccc cgcgttttga agaacgtctg    1080
aaacatattg cggaacgtcc gaacattggc gaatatcgtg gcattggctt tatgtgggcg    1140

```
ctggaagcgg tgaaagataa agcgagcaaa accccgtttg atggcaacct gcgcgtgagc    1200
gaacgtattg cgaacacctg caccgatctg ggcctgattt gccgtccgct gggtcagaat    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 10
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 10

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320
```

```
Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Arg Val Ser
385                 390                 395                 400

Glu Arg Ile Ala Asn Thr Cys Thr Asp Leu Gly Leu Ile Cys Arg Pro
                405                 410                 415

Leu Gly Gln Asn Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 11
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 11
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttgt gcatctgacc     540 tgccccgcatt attggcgtta tggcgaagaa ggcgaaaccg aagaacagtt tgtggcgcgt     600
ctggcccgtg aactggaaga aaccattcag cgtgaaggcg cggataccat tgcgggcttt     660
tttgcggaac cggtgatggg tgcgggcggt gttattccgc cggcgaaagg ctatttcag     720 gcgattctgc cgatcctgcg caaatatgat attccggtga tcagcgatga agtgatttgc     780
ggctttggcc gtaccggcaa cacctggggc tgcgtgacct atgatttac cccggatgcg     840 attattagca gtaaaaacct aaccgcgggt ttttttccgg taggcgcggt gattctgggt     900
ccggaactga gcaaacgtct ggaaaccgcg attgaagcga tcgaagaatt ccgcatggt     960 tttaccgcga gcggccatcc ggtgggttgt gcgattgcgc tgaaagcgat tgatgtggtg    1020
atgaacgaag gcctggccga aaacgtgcgt cgtctggccc gcgttttga agaacgtctg    1080 aaacatattg cggaacgtcc gaacattggc gaatatcgtg gcattggctt tatgtgggcg    1140
ctggaagcgg tgaaagataa agcgagcaaa acccgtttg atggcaacct gagcgtgagc    1200
gaacgtattg cgaacacctg caccgatctg ggcctgattt gcgtcccgct gggccagagc    1260
```

```
gtggttctgt gcccgccgtt tattctgacc gaagcgcaga tggatgaaat gttcgataaa      1320
ctggaaaaag cgctggataa agtgtttgcg gaagtggcgt aa                         1362
```

<210> SEQ ID NO 12
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 12

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 13
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 13

```
atgaacaaac cacaaagttg ggaagcgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg atgcgaaca gcggcctgtg aacatggtg      180
gcgggctttg atcataaagg cctgattgat gcggcgaaag cgcagtatga cgttttccg     240
ggctatcatg cgttttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttgt gcatctgacc     540
tgcccgcatt attggcgtta tggcgaagaa ggcgaaaccg aagaacagtt tgtggcgcgt     600
ctggcccgtg aactggaaga aaccattcag cgtgaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctgggc tgcgtgacct atgatttac cccggatgcg     840
attattagca gcaaaaacct gaccgcgggt ttttttccga tgggcgcggt gattctgggt     900
ccggaactga gcaaacgtct ggaaaccgcg attgaagcga tcgaagaatt ccgcatggt     960
tttaccgcga gcggccatcc ggtgggttgt gcgattgcgc tgaaagcgat tgatgtggtg    1020
atgaacgaag gcctggccga aacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa acccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

```
<210> SEQ ID NO 14
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 14
```

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val 370             375             380
Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 15
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 15
atgaacaaac cgcagagctg ggaaacgcgt gcggaaacct atagcctgta tggctttacc        60
aatatgccga gcctgcatca gcgtggcacc gtggtggtga cccatggcga aggcccgtat       120
atcgtggatg tgaacggccg tcgttatctg gatgcgaaca gcggcctgtg gaacatggtg       180
gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac cgtataacag cgtgtttggc ctgccgctgc cgggctttgt gcatctgacc       540
tgcccgcatt attggcgtta tggcgaagaa ggcgaaaccg aagaacagtt tgtggcgcgt       600
ctggcccgtg aactggaaga aatcattcag cgtgaaggcg cggataccat tgcgggcttt       660
tttgcggaac cggtgatggg tgcgggcggt gttattccgc cggcgaaagg ctattttcag       720
gcgattctgc cgatcctgcg caaatatgat attccggtga tcagcgatga agtgatttgc       780
ggctttggcc gtaccggcaa cacctggggc tgcgtgacct atgattttac cccggatgcg       840
attattagca gtaaaaacct aaccgcgggt ttttttccgg taggcgcggt gattctgggt       900
ccggaactga gcaaacgtct ggaaaccgcg attgaagcga tcgaagaatt ccgcatggt        960
tttaccgcga gcggccatcc ggtgggttgt gcgattgcgc tgaaagcgat tgatgtggtg      1020
atgaacgaag gctggccga aaacgtgcgt cgtctggccc gcgtttttga agaacgtctg      1080
aaacatattg cggaacgtcc gaacattggc gaatatcgtg gcattggctt tatgtgggcg      1140
ctggaagcgg tgaaagataa agcgagcaaa acccgtttg atggcaacct gagcgtgagc      1200
gaacgtattg cgaacacctg caccgatctg ggcctgattt gccgtccgct gggccagagc      1260
gtggttctgt gcccgccgtt tattctgacc gaagcgcaga tggatgaaat gttcgataaa      1320
ctggaaaaag cgctggataa agtgtttgcg gaagtggcgt aa                         1362

<210> SEQ ID NO 16
<211> LENGTH: 453
<212> TYPE: PRT
<213> ORGANISM: Artificial Sequence
<220> FEATURE:

<223> OTHER INFORMATION: variant of transaminase from V. fluvialis

<400> SEQUENCE: 16

```
Met Asn Lys Pro Gln Ser Trp Glu Thr Arg Ala Glu Thr Tyr Ser Leu
1               5                   10                  15

Tyr Gly Phe Thr Asn Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Ile
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400
```

```
Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 17
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 17
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaaa cggtgatggg tgcgggcggt gttattccgc cggcgaaagg ctatttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaag cgctggataa agtgtttgcg gaagtggcgt aa                       1362

<210> SEQ ID NO 18
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 18

Met Asn Lys Pro Gln Ser Trp Glu Thr Arg Ala Glu Thr Tyr Ser Leu
```

-continued

```
1               5                   10                  15
Tyr Gly Phe Thr Asp Met Pro Ser Leu His Gln Arg Gly Thr Val Val
                20                  25                  30
Val Thr His Gly Glu Gly Pro Tyr Ile Val Asp Val His Gly Arg Arg
                35                  40                  45
Tyr Leu Asp Ala Asn Ser Gly Leu Trp Asn Met Val Ala Gly Phe Asp
    50                  55                  60
His Lys Gly Leu Ile Asp Ala Lys Ala Gln Tyr Glu Arg Phe Pro
65                  70                  75                  80
Gly Tyr His Ala Phe Tyr Gly Arg Met Ser Asp Gln Thr Val Met Leu
                85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Met Leu
                115                 120                 125
Trp Phe Leu His Ala Ala Glu Gly Lys Pro Gln Lys Arg Lys Ile Leu
    130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
    210                 215                 220
Val Met Gly Ala Gly Gly Val Ile Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
    275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
                420                 425                 430
```

Gln Met Asp Glu Met Phe Asp Lys Leu Glu Lys Ala Leu Asp Lys Val
          435                 440                 445

Phe Ala Glu Val Ala
    450

<210> SEQ ID NO 19
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 19

```
atgaacaaac cgcagagctg ggaaacgcgt gcggaaacct atagcctgta tggctttacc     60
gatatgccga gcctgcatca gcgtggcacc gtggtggtga cccatggcga aggcccgtat    120
atcgtggatg tgcatggccg tcgttatctg gatgcgaaca gcggcctgtg aacatggtg     180
gcgggctttg atcataaagg cctgattgat gcggcgaaag cgcagtatga acgttttccg    240
ggctatcatg cgttttcggg ccgtatgagc gatcagaccg tgatgctgtc tgaaaaactg    300
gtggaagtga gccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgtga ccgcggtgag cgcgagcatg    480
accggcaaac gtataacag cgtgtttggc ctgccgctgc cgggctttct gcatctgacc     540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcggccggt gttattccgc cggcgaaagg ctattttcag    720
gcgattctgc cgatcctgcg caaatatgat attccggtga tcagcgatga agtgatttgc    780
ggctttggcc gtaccggcaa cacctgggcc tgcgtgacct atgattttac cccggatgcg    840
attattagca gtaaaaacct aaccgcgggt tttttttccgg taggcgcggt gattctgggt    900
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc gcgtttttga gaacgtctg    1080
aaacatattg cggaacgtcc gaacattggc gaatatcgtg gcattggctt atgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                      1362
```

<210> SEQ ID NO 20
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 20

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

```
Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Ser Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
```

<210> SEQ ID NO 21
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 21

```
atgaacaaac cgcagagctg ggaaacgcgt gcggaaacct atagcctgta tggctttacc     60
gatatgccga gcctgcatca gcgtggcacc gtggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
gactatcatg cgtttcatgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgtga ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga accattcag aaggaaggcg cggataccat tgcgggcttt    660
tttgcggaac cggtgatggg tgcgggcggt gttattccgc cggcgaaagg ctattttcag    720
gcgattctgc cgatcttgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt tttttttccgg taggcgcggt gattctgggt    900
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 22
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 22

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Lys Ala Gln Tyr Glu Arg Phe Pro
 65                  70                  75                  80

Asp Tyr His Ala Phe His Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
450

<210> SEQ ID NO 23
<211> LENGTH: 1362

<212> TYPE: DNA
<213> ORGANISM: Artificial Sequence
<220> FEATURE:
<223> OTHER INFORMATION: variant of transaminase from V. fluvialis

<400> SEQUENCE: 23

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgtttaatgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt tttttccgg taggcgcggt gattctgggt     900
ccggaactga gcaaacgtct ggaaaccgcg attgaagcga tcgaagaatt ccgcatggt     960
tttaccgcgg cggccatcc ggtgggttgt gcgattgcgc tgaaagcgat tgatgtggtg    1020
atgaacgaag gcctggccga aacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 24
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 24

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asn Gly Arg Met Ser Asp Gln Thr Val Met Leu
```

```
                    85                  90                  95
Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
            130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
            210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 25
<211> LENGTH: 1362
<212> TYPE: DNA
<213> ORGANISM: Artificial Sequence
<220> FEATURE:
<223> OTHER INFORMATION: variant of transaminase from V. fluvialis
```

<400> SEQUENCE: 25

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggcttttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt tttttttccgg taggcgcggt gattctgggt     900
ccggaactga gcaaacgtct ggaaaccgcg attgaagcga tcgaagaatt ccgcatggtg     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 26
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 26

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110
```

```
Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 27
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 27
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
```

```
atcgtggatg tgcatggccg tcgttatctg gatgcgaaca gcggcctgct gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgtga ccgcggtgag cgcgagcatg    480
accggcaaac cgtataacag cgtgtttggc ctgccgctgc cgggcttcct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctatttcag    720 gcgattctgc cgatcctgcg caaatatgat attccggtga tcagcgatga agtgatttgc    780
ggctttggcc gtaccggcaa cacctggggc tgcgtgaccc tgattttac cccggatgcg    840 attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt atgtgggcg   1140 ctggaagcgg tgaaagataa agcgagcaaa gccccgttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 28
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 28

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140
```

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

```
<210> SEQ ID NO 29
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 29
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg aacatggtg        180 gcgggctttg atcataaagg cctgattgat gcggcgaaag cgcagtatga acgttttccg       240
```

```
ggccatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgtga ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt tttttccgg taggcgcggt gattctgggt    900
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg   1080 aaacatattg cggaacgtcc gaacattggc gaatatcgtg cattggcctt atgtggggcg   1140
ctggaagcgg tgaaagataa agcgagcaaa gccccgtttg atggcaacct gagcgtgagc   1200
gaacgtattg cgaacacctg caccgatctg ggcctgattt gccgtccgtt cggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 30
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 30

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
50                  55                  60

His Lys Gly Leu Ile Asp Ala Ala Lys Ala Gln Tyr Glu Arg Phe Pro
65                  70                  75                  80

Gly His His Ala Phe Tyr Gly Arg Met Ser Asp Gln Thr Val Met Leu
                85                  90                  95

Ser Glu Lys Leu Val Glu Val Ser Pro Phe Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
```

```
                165                 170                 175
Leu His Leu Thr Cys Pro His Tyr Trp Arg Tyr Gly Glu Glu Gly Glu
                    180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Phe Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 31
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 31
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cggcgtacgg ccgtatgagc gatcagaccg tgatgctgtc tgaaaaactg     300
gtggaagtga gcccgtttga tagcggccgt gtgtttttata ccaacagcgg cagcgaagcg     360
aacgatacca tggtgaaaat gctgtggttt ctgcatgcgg cggaaggcaa accgcagaaa     420
```

```
cgtaaaattc tgacccgttg aacgcgtat catggcgtga ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctatttcag      720 gcgattctgc cgatcctgcg caaatatgat attccggtga tcagcgatga agtgatttgc      780
ggctttggcc gtaccggcaa cacctggggc tgcgtgacct atgatttac cccggatgcg      840 attattagca gtaaaaacct aaccgcgggt ttttttccgg taggcgcggt gattctgggt      900
ccggaactga gcaaacgtct ggaaaccgcg attgaagcga tcgaagaatt gccccatggt      960
tttaccgcgg gcggccatcc ggtgggttgt gcgattgcgc tgaaagcgat tgatgtggtg     1020
atgaacgaag gcctggccga aaacgtgcgt cgtctggccc cgcgttttga agaacgtctg     1080
aaacatattg cggaacgtcc gaacattggc gaatatcgtg cattggctt tatgtgggcg     1140 ctggaagcgg tgaaagataa agcgagcaaa gccccgtttg atggcaacct gagcgtgagc     1200
gaacgtattg cgaacacctg caccgatctg ggcctgattt gcgtccgct gggccagagc     1260 gtggttctgt gcccgccgtt tattctgacc gaagcgcaga tggatgaaat gttcgataaa     1320
ctggaaaaag cgctggataa agtgtttgcg gaagtggcgt aa                       1362
```

<210> SEQ ID NO 32
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 32

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Ala Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

Thr Glu Glu Gln Phe Val Ala Arg Leu Ala Arg Glu Glu Thr
    195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Leu Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 33
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 33

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg atgcgaaca gcggcctgtg aacatggtg      180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgcta ccgcggtgag cgcgagcatg     480
accggcaaac cgtataacag cgtgtttggc ctgccgctgc cgggctttct gcatctgacc     540
```

```
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgatttac cccggatgcg    840 attattagca gtaaaaacct aaccgcgggt ttttttccgg taggcgcggt gattctgggt    900
ccggaactga gcaaacgtct ggaaaccgcg attgaagcga tcgaagaatt gggtcatggt    960
tttaccgcgg cgggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg cattggcttt atgtgggcg    1140 ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 34
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 34

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

```
Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Leu Gly His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 35
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 35
atgaacaaac cgcagagctg ggaaacgcgt gcggaaacct atagtctcta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgtcatacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgcta ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactgaaaga aaccattcag aaggaaggcg cggataccat tgcgggcttt     660
tttgcggaac cggtgatggg tgcgggcggt gttattccgc cggcgaaagg ctatttcag     720
```

```
gcgattctgc cgatcctgcg caaatatgat attccggtga tcagcgatga agtgatttgc    780
ggctttggcc gtaccggcaa cacctggggc tgcgtgacct atgatttac  cccggatgcg    840 attattagca gtaaaaacct aaccgcgggt ttttttccgg taggcgcggt gattctgggt    900
ccggaactga gcaaacgtct ggaaaccgcg attgaagcga tcgaagaatt ccgcatggt     960 tttaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg    1080 aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 36
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 36

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ser Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
```

|  |  | 245 |  |  |  | 250 |  |  |  | 255 |  |
|---|---|---|---|---|---|---|---|---|---|---|---|

Glu Val Ile Cys Gly Phe Gly Arg Thr Gly Asn Thr Trp Gly Cys Val
    260                    265                  270

Thr Tyr Asp Phe Thr Pro Asp Ala Ile Ile Ser Ser Lys Asn Leu Thr
   275                    280                  285

Ala Gly Phe Phe Pro Val Gly Ala Val Ile Leu Gly Pro Glu Leu Ser
   290                    295                  300

Lys Arg Leu Glu Thr Ala Ile Glu Ala Ile Glu Glu Phe Pro His Gly
305                    310                  315                  320

Phe Thr Ala Gly Gly His Pro Val Gly Cys Ala Ile Ala Leu Lys Ala
            325                  330                  335

Ile Asp Val Val Met Asn Glu Gly Leu Ala Glu Asn Val Arg Arg Leu
            340                  345                  350

Ala Pro Arg Phe Glu Glu Arg Leu Lys His Ile Ala Glu Arg Pro Asn
            355                  360                  365

Ile Gly Glu Tyr Arg Gly Ile Gly Phe Met Trp Ala Leu Glu Ala Val
370                    375                  380

Lys Asp Lys Ala Ser Lys Ala Pro Phe Asp Gly Asn Leu Ser Val Ser
385                    390                  395                  400

Glu Arg Ile Ala Asn Thr Cys Thr Asp Leu Gly Leu Ile Cys Arg Pro
            405                  410                  415

Leu Gly Gln Ser Val Val Leu Cys Pro Pro Phe Ile Leu Thr Glu Ala
            420                  425                  430

Gln Met Asp Glu Met Phe Asp Lys Leu Glu Lys Ala Leu Asp Lys Val
            435                  440                  445

Phe Ala Glu Val Ala
   450

<210> SEQ ID NO 37
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 37

```
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg aacatggtg       180
gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgtttcata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactgaagaa aaccattcag aaggaaggcg cggataccat tgcgggcttt       660
tttgcggaac cggtgatggg tgcgggcggt gttattccgc cggcgaaagg ctatttttcag    720
gcgattctgc cgatcctgcg caaatatgat attccggtga tcagcgatga agtgatttgc       780
ggctttggcc gtaccggcaa cacctggggc tgcgtgacct atgattttac cccggatgcg       840
```

```
attattagca gtaaaaacct aaccgcgggt tttttccgg taggcgcggt gattctgggt    900
ccagaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacaccag caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 38
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 38

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

His Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Ser Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
    435                 440                 445

Phe Ala Glu Val Ala
    450
```

<210> SEQ ID NO 39
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 39

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cggcgtacgg ccgtatgagc gatcagaccg tgatgctgtc tgaaaaactg     300
gtggaagtga gccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgcta ccgcggtgag cgcgagcatg     480
accggcaaac gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt     960
tttaccgcgg gcggccatcc ggtgggttgt gcgattgcgc tgaaagcgat tgatgtggtg    1020
```

```
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataag    1320
ctggaaaaag cgctggataa agtgtttgcg gaagtggcgt aa                       1362
```

<210> SEQ ID NO 40
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 40

```
Met Asn Lys Pro Gln Ser Trp Glu Thr Arg Ala Glu Thr Tyr Ser Leu
  1               5                  10                  15

Tyr Gly Phe Thr Asp Met Pro Ser Leu His Gln Arg Gly Thr Val Val
             20                  25                  30

Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
     50                  55                  60

His Lys Gly Leu Ile Asp Ala Ala Lys Ala Gln Tyr Glu Arg Phe Pro
 65                  70                  75                  80

Gly Tyr His Ala Ala Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300
```

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 41
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 41
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctat taacatggtg     180 gcgggctttg atcataaagg cctgattgat gcggcgaaag cgcagtatga acgttttccg     240
ggctatcatg cgttttacgg ccgtatgagc gatcagaccc tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540 tgccccgcatt attggcgtta tggcgaagaa ggcgaaaccg aagaacagtt tgtcgcgcgt     600
ctggcccgtg aactggaaga aaccattcag aaggaaggcg cggataccat gcgggctttt     660
tttgcggaac cggtgatggg tgcgggcggt gttattccgc cggcgaaagg ctatttttcag    720 gcgattctgc cgatcctgcg caaatatgat attccggtga tcagcgatga agtgatttgc     780
ggctttggcc gtaccggcaa cacctggggc tgcgtgacct atgatttttac cccggatgcg     840 attattagca gtaaaaacct aaccgcgggt ttttttccgg taggcgcggt gattctgggt     900
ccggaactga gcaaacgtct ggaaaccgcg attgaagcga tcgaagaatt ccgcatggt      960 tttaccgcgg cggccatccc ggtgggttgt gcgattgcgc tgaaagcgat tgatgtggtg    1020
atgaacgaag tcctggccga aaacgtgcgt cgtctggccc cgcgttttga agaacgtctg    1080
aaacatattg cggaacgtcc gaacattggc gaatatcgtg gcattggctt tatgtgggcg    1140

```
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 42
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 42

| | | | | | | | | | | | | | | | |
|---|---|---|---|---|---|---|---|---|---|---|---|---|---|---|---|
| Met | Asn | Lys | Pro | Gln | Ser | Trp | Glu | Thr | Arg | Ala | Glu | Thr | Tyr | Ser | Leu |
| 1 | | | | 5 | | | | | 10 | | | | | 15 | |

Tyr Gly Phe Thr Asp Met Pro Ser Leu His Gln Arg Gly Thr Val Val
              20                  25                  30

Val Thr His Gly Glu Gly Pro Tyr Ile Val Asp Val His Gly Arg Arg
 35                  40                  45

Tyr Leu Asp Ala Asn Ser Gly Leu Ile Asn Met Val Ala Gly Phe Asp
 50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala

```
                  325                 330                 335
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 43
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 43
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca cgggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcagta ccgcggtgag cgcgagcatg     480
accggcaaac gtataacagc gtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctatttttcag    720
gcgattctgc cgatcctgcg caaatatgat attccggtga tcagcgatga agtgatttgc     780
ggctttggcc gtaccggcaa cacctgggc tgcgtgacct atgattttac cccggatgcg      840
attattagca gtaaaaacct aaccgcgggt ttttttccgg taggcgcggt gattctgggt     900
ccggaactga gcaaacgtct ggaaaccgcg attgaagcga tcgaagaatt ccgcatggtg     960
tttaccgcgg gcggccatcc ggtgggttgt gcgattgcgc tgaaagcgat tgatgtggtg    1020
atgaacgaag cctggccgga aaacgtgcgt cgtctggccc gcgttttga agaacgtctg     1080
aaacatattg cggaacgtcc gaacattggc gaatatcgtg gcattggctt tatgtgggcg    1140
ctggaagcgg tgaaagataa agcgagcaaa gcccgtttg atggcaacct gagcgtgagc     1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
```
ctggaaaaag cgctggataa agtgtttgcg gaagtggcgt aa                        1362

<210> SEQ ID NO 44
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 44

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 45
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 45
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctcat taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcagta ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttac ccgggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt      960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg     1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc     1260
gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 46

```
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 46

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ile Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380
```

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 47
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 47
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttctgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcagta ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaaa cggtgatggg tgcgggcggt gttattccgc cggcgaaagg ctatttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt      960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 48
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 48

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
```

```
            405                 410                 415
Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 49
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 49
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctatttcag     720 gcgattctgc cgatcctgcg caaatatgat attccggtga tcagcgatga agtgatttgc     780
ggctttggcc gtaccggcaa cacctgggc tgcgtgacct atgatttac cccggatgcg     840 attattagca gtaaaaacct aaccgcgggt ttttttccgg taggcgcggt gattctgggt     900
ccggaactga gcaaacgtct ggaaaccgcg attgaagcga tcgaagaatt tggtcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt atgtgggcg    1140 ctggaagcgg tgaaagataa agcgagcaaa gccccgtttg atggcaacct gagcgtgagc    1200
gaacgtattg cgaacacctg cgccgatctg ggcctgattt gcgtccgct gggccagagc    1260 gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 50
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 50

Met Asn Lys Pro Gln Ser Trp Glu Thr Arg Ala Glu Thr Tyr Ser Leu
1               5                   10                  15
```

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Gly His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Ala Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 51
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 51

| | |
|---|---:|
| atgaacaaac cgcagagctg ggaaacgcgt gcggaaacct atagcctgta tggctttacc | 60 |
| gatatgccga gcctgcatca gcgtggcacc gtggtggtga cccatggcga aggcccgtat | 120 |
| atcgtggatg tgcatggccg tcgttatctg gatgcgaaca gcggcctgtg aacatggtg | 180 |
| gcgggctttg atcataaagg cctgattgat gcggcgaaag cgcagtatga acgttttccg | 240 |
| ggccatcatg cgttttacgg ccgtatgagc gatcagaccg tgatgctgtc tgaaaaactg | 300 |
| gtggaagtga gcccgtttga tagcggccgt gtgttttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg aacgcgtat catggcgtga ccgcggtgag cgcgagcatg | 480 |
| accggcaaac cgtataacag cgtgtttggc ctgccgctgc cgggctttct gcatctgacc | 540 |
| tgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggcaa cctgggc tgcgtgacct atgattttac cccggatgcg | 840 |
| attattagca gtaaaaacct aaccgcgggt tttttccgg taggcgcggt gattctgggt | 900 |
| ccggaactga gcaaacgtct ggaaaccgcg attgaagcga tcgaagaatt ccgcatggt | 960 |
| tttaccgcgg cggccatcc ggtgggttgt gcgattgcgc tgaaagcgat tgatgtggtg | 1020 |
| atgaacgaag gcctggccga aaacgtgcgt cgtctggccc cgcgttttga agaacgtctg | 1080 |
| aaacatattg cggaacgtcc gaacattggc gaatatcgtg cattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg ggcctgattt gcgtccgct gggcagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 52
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 52

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg

```
            35                  40                  45
Tyr Leu Asp Ala Asn Ser Gly Leu Trp Asn Met Val Ala Gly Phe Asp
 50                  55                  60
His Lys Gly Leu Ile Asp Ala Lys Ala Gln Tyr Glu Arg Phe Pro
 65                  70                  75                  80
Gly His His Ala Phe Tyr Gly Arg Met Ser Asp Gln Thr Val Met Leu
                     85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Met Leu
                115                 120                 125
Trp Phe Leu His Ala Ala Glu Gly Lys Pro Gln Lys Arg Lys Ile Leu
                130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                    165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                    245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
                275                 280                 285
Ala Gly Phe Phe Pro Val Gly Ala Val Ile Leu Gly Pro Glu Leu Ser
                290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                    325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Ala Val
                370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                    405                 410                 415
Leu Gly Gln Ser Val Val Leu Cys Pro Pro Phe Ile Leu Thr Glu Ala
                420                 425                 430
Gln Met Asp Glu Met Phe Asp Lys Leu Glu Lys Ala Leu Asp Lys Val
                435                 440                 445
Phe Ala Glu Val Ala
                450
```

<210> SEQ ID NO 53
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 53

```
atgaacaaac cgcagagctg ggaaacgcgt gcgggaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaaacct aaccgcgggt ttttttccgg taggcgcggt gattctgggt     900
ccggaactga gcaaacgtct ggaaaccgcg attgaagcga tcgaagaatt tccgcatggt     960
tttaccgcgg gcggccatcc ggtgggttgt gcgattgcgc tgaaagcgat tgatgtggtg    1020
atgaacgaag gcctggccga aacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcagg tggatgaaat gttcgataaa    1320
ctggaaaaag cgctggataa agtgtttgcg gaagtggcgt aa                       1362
```

<210> SEQ ID NO 54
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 54

Met Asn Lys Pro Gln Ser Trp Glu Thr Arg Ala Gly Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Val Asp Glu Met Phe Asp Lys Leu Glu Lys Ala Leu Asp Lys Val
        435                 440                 445

Phe Ala Glu Val Ala
    450

<210> SEQ ID NO 55
<211> LENGTH: 1362
<212> TYPE: DNA

```
<213> ORGANISM: Artificial Sequence
<220> FEATURE:
<223> OTHER INFORMATION: variant of transaminase from V. fluvialis

<400> SEQUENCE: 55
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cggtgtacgg ccgtatgagc gatcagaccg tgatgctgtc tgaaaaactg     300
gtggaagtga gcccgtttga tagcggccgt gtgtttata ccaacagcgg cagcgaagcg      360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt      660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt tttttccgg taggcgcggt gattctgggt      900
ccggaactga gcaaacgtct ggaaaccgcg attgaagcga tcgaagaatt ccgcatggt      960
tttaccgcgg gcggccatcc ggtgggttgt gcgattgcgc tgaaagcgat tgatgtggtg    1020
atgaacgaag cctggccga aaacgtgcgt cgtctggccc gcgttttga agaacgtctg     1080
aaacatattg cggaacgtcc gaacattggc gaatatcgtg gcattggctt tatgtgggcg    1140
ctggaagcgt tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 56
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 56

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Val Tyr Gly Arg Met Ser Asp Gln Thr Val Met Leu
                85                  90                  95
```

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130             135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
            210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 57
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 57

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgagctacgg ccgtatgagc gatcagaccg tgatgctgtc tgaaaaactg     300
gtggaagtga gcccgtttga tagcggccgt gtgtttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattccgc cggcgaaagg ctatttcag      720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaaacct aaccgcgggt ttttttccgg taggcgcggt gattctgggt     900
ccggaactga gcaaacgtct ggaaaccgcg attgaagcga tcgaagaatt ccgcatggt      960
tttaccgcgg cggccatcc ggtgggttgt gcgattgcgc tgaaagcgat tgatgtggtg    1020
atgaacgaag gctggccga aaacgtgcgt cgtctggccc gcgttttga agaacgtctg     1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacaccctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 58
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 58

```
Met Asn Lys Pro Gln Ser Trp Glu Thr Arg Ala Glu Thr Tyr Ser Leu
1               5                  10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ser Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
```

```
            115                 120                 125
Trp Phe Leu His Ala Ala Glu Gly Lys Pro Gln Lys Arg Lys Ile Leu
    130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
    210                 215                 220
Val Met Gly Ala Gly Gly Val Ile Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
                275                 280                 285
Ala Gly Phe Phe Pro Val Gly Ala Val Ile Leu Gly Pro Glu Leu Ser
                290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Ala Val
                370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
                420                 425                 430
Gln Met Asp Glu Met Phe Asp Lys Leu Glu Lys Ala Leu Asp Lys Val
                435                 440                 445
Phe Ala Glu Val Ala
        450

<210> SEQ ID NO 59
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 59
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
```

| | | | | |
|---|---|---|---|---|
| atcgtggatg | tgcatggccg | tcgttatctg | gatgcgaaca | gcggcctgtg gaacatggtg | 180 |
| gcgggctttg | atcataaagg | cctgattgat | gcggcgaaag | cgcagtatga acgttttccg | 240 |
| ggctatcatg | cgacctacgg | ccgtatgagc | gatcagaccg | tgatgctgtc tgaaaaactg | 300 |
| gtggaagtga | gcccgtttga | tagcggccgt | gtgtttttata | ccaacagcgg cagcgaagcg | 360 |
| aacgatacca | tggtgaaaat | gctgtggttt | ctgcatgcgg | cggaaggcaa accgcagaaa | 420 |
| cgtaaaattc | tgacccgttg | gaacgcgtat | catggcgtga | ccgcggtgag cgcgagcatg | 480 |
| accggcaaac | cgtataacag | cgtgtttggc | ctgccgctgc | cgggctttct gcatctgacc | 540 |
| tgcccgcatt | attggcgtta | tggcgaagaa | ggcgaaaccg | aagaacagtt tgtcgcgcgt | 600 |
| ctggcccgtg | aactggaaga | aaccattcag | aaggaaggcg | cggataccat tgcgggcttt | 660 |
| tttgcggaac | cggtgatggg | tgcggcggt | gttattccgc | cggcgaaagg ctattttcag | 720 |
| gcgattctgc | cgatcctgcg | caaatatgat | attccggtga | tcagcgatga agtgatttgc | 780 |
| ggctttggcc | gtaccggcaa | cacctggggc | tgcgtgacct | atgatttac cccggatgcg | 840 |
| attattagca | gtaaaaacct | aaccgcgggt | ttttttccgg | taggcgcggt gattctgggt | 900 |
| ccggaactga | gcaaacgtct | ggaaaccgcg | attgaagcga | tcgaagaatt tccgcatggt | 960 |
| tttaccgcgg | gcgccatcc | ggtgggttgt | gcgattgcgc | tgaaagcgat tgatgtggtg | 1020 |
| atgaacgaag | gcctggccga | aaacgtgcgt | cgtctggccc | cgcgttttga gaacgtctg | 1080 |
| aaacatattg | cggaacgtcc | gaacattggc | gaatatcgtg | cattggctt tatgtgggcg | 1140 |
| ctggaagcgg | tgaaagataa | agcgagcaaa | gccccgtttg | atggcaacct gagcgtgagc | 1200 |
| gaacgtattg | cgaacacctg | caccgatctg | ggcctgattt | gccgtccgct gggccagagc | 1260 |
| gtggttctgt | gcccgccgtt | tattctgacc | gaagcgcaga | tggatgaaat gttcgataaa | 1320 |
| ctggaaaaag | cgctggataa | agtgtttgcg | gaagtggcgt | aa | 1362 |

<210> SEQ ID NO 60
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 60

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Thr Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140
```

```
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
            165                 170                 175
Leu His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
        195                 200                 205
Ile Gln Lys Glu Gly Ala Asp Thr Ile Ala Gly Phe Phe Ala Glu Pro
        210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
            245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
        290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
            325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
        370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
            405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450
```

<210> SEQ ID NO 61
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 61

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cggcgtacgg ccgtatgagc gatcagaccg tgatgctgtc tgaaaaactg     300
```

```
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg aacgcgtat catggcgtga ccgcggtgag cgcgagcatg     480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga accattcag aaggaaggcg cggataccat tgcgggcttt     660
tttgcggaac cggtgatggg tgcgggcggt gttattccgc cggcgaaagg ctatttcag    720 gcgattctgc cgatcctgcg caaatatgat attccggtga tcagcgatga agtgatttgc    780
ggctttggcc gtaccggcaa cacctggggc tgcgtgacct atgatttac cccggatgcg     840 attattagca gtaaaaacct aaccgcgggt tttttccgg taggcgcggt gattctgggt       900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg  1080
aaacatattg cggaacgtcc gaacattggc gaatatcgtg cattggcttt atgtgggcg   1140 ctggaagcgg tgaaagataa agcgagcaaa gccccgtttg atggcaacct gagcgtgagc  1200
gaacgtattg cgaacacctg caccgatctg ggcctgattt gccgtccgct gggccagagc  1260
gtggttctgt gcccgccgtt tattctgacc gaagcgcaga tggatgaaat gttcgataaa  1320
ctggaaaaag cgctggataa agtgtttgcg gaagtggcgt aa                       1362
```

<210> SEQ ID NO 62
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 62

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Ala Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175
```

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Lys Gly Tyr Phe Gln
225                 230                 235                 240

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
        260                 265                 270

Thr Tyr Asp Phe Thr Pro Asp Ala Ile Ile Ser Ser Lys Asn Leu Thr
    275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 63
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 63
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgaactacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgc cggaaggcaa accgcagaaa     420

```
cgtaaaattc tgacccgttg gaacgcgtat catggcgtga ccgcggtgag cgcgagcatg    480
accggcaaac cgtataacag cgtgtttggc ctgccgctgc cgggcttttct gcatctgacc    540 tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctgtggc tgcgtgacct atgattttac cccggatgcg    840
attattagca gtaaaaacct aaccgcgggt tttttccgg taggcgcggt gattctgggt    900
ccggaactga gcaaacgtct ggaaaccgcg attgaagcga tcgaagaatt ccgcatggt    960 tttaccgcgg cggccatcc ggtgggttgt gcgattgcgc tgaaagcgat tgatgtggtg    1020
atgaacgaag gcctggccga aacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 64
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 64

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Asn Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
```

```
                 195                 200                 205
Ile Gln Lys Glu Gly Ala Asp Thr Ile Ala Gly Phe Phe Ala Glu Pro
    210                 215                 220

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 65
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 65
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg aacatggtg        180 gcgggctttg atcataaagg cctgattgat gcggcgaaag cgcagtatga acgttttccg       240
ggctatcatg cgtgctacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttt gaacgcgtat catggcgtga ccgcggtgag cgcgagcatg       480
accggcaaac cgtataacag cgtgtttggc ctgccgctgc cgggctttct gcatctgacc       540
tgcccgcatt attggcgtta tggcgaagaa ggcgaaaccg aagaacagtt tgtcgcgcgt       600
```

```
ctggcccgtg aactggaaga aaccattcag aaggaaggcg cggataccat tgcgggcttt      660
tttgcggaac cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggcaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt ccgcatggt      960 tttaccgcgg gcggccatcc ggtgggttgt gcgattgcgc tgaaagcgat tgatgtggtg     1020
atgaacgaag gctggccga aaacgtgcgt cgtctggccc gcgttttga agaacgtctg      1080 aaacatattg cggaacgtcc gaacattggc gaatatcgtg gcattggctt tatgtgggcg     1140
ctggaagcgt tgaaagataa agcgagcaaa gccccgtttg atggcaacct gagcgtgagc     1200
gaacgtattg cgaacaccctg caccgatctg ggcctgattt gccgtccgct gggccagagc     1260
gtggttctgt gcccgccgtt tattctgacc gaagcgcaga tggatgaaat gttcgataaa     1320
ctggaaaaag cgctggataa agtgtttgcg gaagtggcgt aa                          1362
```

<210> SEQ ID NO 66
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 66

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Cys Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
        260                 265                 270

Thr Tyr Asp Phe Thr Pro Asp Ala Ile Ile Ser Ser Lys Asn Leu Thr
    275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 67
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 67
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg      180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgtttata ccaacagcgg cagcgaagcg      360
aacgatacca tggtgaaaat gctgtggttt ctgcatgcgg cggaaggcaa accgcagaaa     420
cgtaaaattc tgacccgttg aacgcgtat catggcacca ccgcggtgag cgcgagcatg      480
accggcaaac cgtataacag cgtgtttggc ctgccgctgc cgggcttcct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720

| | | |
|---|---|---|
| gcgattctgc cgatcctgcg caaatatgat attccggtga tcagcgatga agtgatttgc | 780 | |
| ggctttggcc gtaccggcaa cacctggggc tgcgtgacct atgattttac cccggatgcg | 840 | |
| attattagca gtaaaaacct aaccgcgggt tttttccgg taggcgcggt gattctgggt | 900 | |
| ccggaactga gcaaacgtct ggaaaccgcg attgaagcga tcgaagaatt tccgcatggt | 960 | |
| tttaccgcgg gcggccatcc ggtgggttgt gcgattgcgc tgaaagcgat tgatgtggtg | 1020 | |
| atgaacgaag gcctggccga aaacgtgcgt cgtctggccc gcgttttga agaacgtctg | 1080 | |
| aaacatattg cggaacgtcc gaacattggc gaatatcgtg gcattggctt tatgtgggcg | 1140 | |
| ctggaagcgg tgaaagataa agcgagcaaa gccccgtttg atggcaacct gagcgtgagc | 1200 | |
| gaacgtattg cgaacacctg caccgatctg ggcctgattt gccgtccgct gggccagagc | 1260 | |
| gtggttctgt gcccgccgtt tattctgacc gaagcgcaga tggatgaaat gttcgataaa | 1320 | |
| ctggaaaaag cgctggataa agtgtttgcg gaagtggcgt aa | 1362 | |

<210> SEQ ID NO 68
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 68

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Thr Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Lys Gly Tyr Phe Gln
225                 230                 235                 240

Ala Ile Leu Pro Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 69
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 69

```
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg gaacatggtg       180
gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttg aacgcgtat catggcaaca ccgcggtgag cgcgagcatg       480
accggcaaac cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactggaaga accattcag aaggaaggcg cggataccat tgcgggcttt       660
tttgcggaac cggtgatggg tgcgggcggt gttattccgc cggcgaaagg ctattttcag       720
gcgattctgc cgatcctgcg caaatatgat attccggtga tcagcgatga agtgatttgc       780
ggctttggcc gtaccggcaa cacctggggc tgcgtgacct atgatttac cccggatgcg       840 attattagca gtaaaaacct aaccgcgggt ttttttccgg taggcgcggt gattctgggt       900
```

```
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg cattggcttt atgtgggcg    1140 ctggaagcgg tgaaagataa agcgagcaaa gccccgtttg atggcaacct gagcgtgagc   1200
gaacgtattg cgaacacctg caccgatctg ggcctgattt gcgtccgct gggccagagc    1260 gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 70
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 70

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Asn Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
```

```
                    275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
            355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
                420                 425                 430
Gln Met Asp Glu Met Phe Asp Lys Leu Glu Lys Ala Leu Asp Lys Val
            435                 440                 445
Phe Ala Glu Val Ala
    450

<210> SEQ ID NO 71
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 71
atgaacaaac cgcagagctg ggaaacgcgt gcggaaacct atagcctgta tggctttacc     60
gatatgccga gcctgcatca gcgtggcacc gtggtggtga cccatggcga aggcccgtat    120
atcgtggatg tgcatggccg tcgttatctg gatgcgaaca cgcgcctgtg aacatggtg    180 gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgtttata ccaacagcgg cagcgaagcg    360
aacgatacca tggtgaaaat gctgtggttt ctgcatgcgg cggaaggcaa accgcagaaa    420
cgtaaaattc tgacccgttt gaacgcgtat catggcggca ccgcggtgag cgcgagcatg    480
accggcaaac gtataacag cgtgtttggc ctgccgctgc cgggctttct gcatctgacc    540 tgccccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctatttcag    720 gcgattctgc cgatcctgcg caaatatgat attccggtga tcagcgatga agtgatttgc    780
ggctttggcc gtaccggcaa cacctggggc tgcgtgacct atgatttac cccggatgcg    840 attattagca gtaaaaaacct aaccgcgggt ttttttccgg taggcgcggt gattctgggt    900
ccggaactga gcaaacgtct ggaaaccgcg attgaagcga tcgaagaatt ccgcatggtt    960
tttaccgcgg gcggccatcc ggtgggttgt gcgattgcgc tgaaagcgat tgatgtggtg   1020
```

```
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc     1260 gtggttctgt gcccgccgtt tattctgacc gaagcgcaga tggatgaaat gttcgataaa    1320
ctggaaaaag cgctggataa agtgtttgcg aagtggcgt aa                        1362
```

<210> SEQ ID NO 72
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 72

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Gly Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300
```

Lys Arg Leu Glu Thr Ala Ile Glu Ala Ile Glu Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 73
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 73

| | | | | | |
|---|---|---|---|---|---|
| atgaacaaac | cgcagagctg | ggaaacgcgt | gcggaaacct | atagcctgta | tggctttacc | 60 |
| gatatgccga | gcctgcatca | gcgtggcacc | gtggtggtga | cccatggcga | aggcccgtat | 120 |
| atcgtggatg | tgcatggccg | tcgttatctg | gatgcgaaca | gcggcctgtg | gaacatggtg | 180 |
| gcgggctttg | atcataaagg | cctgattgat | gcggcgaaag | cgcagtatga | acgttttccg | 240 |
| ggctatcatg | tgttttacgg | ccgtatgagc | gatcagaccg | tgatgctgtc | tgaaaaactg | 300 |
| gtggaagtga | gcccgtttga | tagcggccgt | gtgttttata | ccaacagcgg | cagcgaagcg | 360 |
| aacgatacca | tggtgaaaat | gctgtggttt | ctgcatgcgg | cggaaggcaa | accgcagaaa | 420 |
| cgtaaaattc | tgacccgttg | gaacgcgtat | catggcgtga | ccgcggtgag | cgcgagcatg | 480 |
| accggcaaac | cgtataacag | cgtgtttggc | ctgccgctgc | cgggctttct | gcatctgacc | 540 |
| tgcccgcatt | attggcgtta | tggcgaagaa | ggcgaaaccg | aagaacagtt | tgtcgcgcgt | 600 |
| ctggcccgtg | aactggaaga | aaccattcag | aaggaaggcg | cggataccat | tgcgggcttt | 660 |
| tttgcggaac | cggtgatggg | tgcgggcggt | gttattccgc | cggcgaaagg | ctattttcag | 720 |
| gcgattctgc | cgatcctgcg | caaatatgat | attccggtga | tcagcgatga | agtgatttgc | 780 |
| ggctttggcc | gtaccggcaa | cacctggggc | tgcgtgacct | atgattttac | cccggatgcg | 840 |
| attattagca | gtaaaaacct | aaccgcgggt | ttttttccgg | taggcgcggt | gattctgggt | 900 |
| ccggaactga | gcaaacgtct | ggaaaccgcg | attgaagcga | tcgaagaaat | gccgcatggt | 960 |
| tttaccgcgg | gcggccatcc | ggtgggttgt | gcgattgcgc | tgaaagcgat | tgatgtggtg | 1020 |
| atgaacgaag | gcctggccga | aaacgtgcgt | cgtctggccc | gcgttttga | agaacgtctg | 1080 |
| aaacatattg | cggaacgtcc | gaacattggc | gaatatcgtg | gcattggctt | tatgtgggcg | 1140 |
| ctggaagcgg | tgaaagataa | agcgagcaaa | gccccgtttg | atggcaaccct | gagcgtgagc | 1200 |

```
gaacgtattg cgaacacctg caccgatctg ggcctgattt gccgtccgct gggccagagc    1260
gtggttctgt gcccgccgtt tattctgacc gaagcgcaga tgatgaaat gttcgataaa     1320 ctggaaaaag cgctggataa agtgtttgcg gaagtggcgt aa                       1362
```

<210> SEQ ID NO 74
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 74

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Met Pro His Gly
305                 310                 315                 320

Phe Thr Ala Gly Gly His Pro Val Gly Cys Ala Ile Ala Leu Lys Ala
                325                 330                 335
```

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 75
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 75

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgtttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcgaaac cggtgatggg tgcggccggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaata tccgcatggt     960
tttaccgcgg gcggccatcc ggtggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt atgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc    1260
gtggttctgt gcccgccgtt tattctgacc gaagcgcaga tggatgaaat gttcgataaa    1320
```
ctggaaaaag cgctggataa agtgtttgcg gaagtggcgt aa                    1362

<210> SEQ ID NO 76
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 76

```
Met Asn Lys Pro Gln Ser Trp Glu Thr Arg Ala Glu Thr Tyr Ser Leu
1               5                   10                  15
Tyr Gly Phe Thr Asp Met Pro Ser Leu His Gln Arg Gly Thr Val Val
            20                  25                  30
Val Thr His Gly Glu Gly Pro Tyr Ile Val Asp Val His Gly Arg Arg
        35                  40                  45
Tyr Leu Asp Ala Asn Ser Gly Leu Trp Asn Met Val Ala Gly Phe Asp
    50                  55                  60
His Lys Gly Leu Ile Asp Ala Ala Lys Ala Gln Tyr Glu Arg Phe Pro
65                  70                  75                  80
Gly Tyr His Ala Phe Tyr Gly Arg Met Ser Asp Gln Thr Val Met Leu
                85                  90                  95
Ser Glu Lys Leu Val Glu Val Ser Pro Phe Asp Ser Gly Arg Val Phe
            100                 105                 110
Tyr Thr Asn Ser Gly Ser Glu Ala Asn Asp Thr Met Val Lys Met Leu
        115                 120                 125
Trp Phe Leu His Ala Ala Glu Gly Lys Pro Gln Lys Arg Lys Ile Leu
    130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
        195                 200                 205
Ile Gln Lys Glu Gly Ala Asp Thr Ile Ala Gly Phe Phe Ala Glu Pro
    210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Tyr Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
```

Ile Gly Glu Tyr Arg Gly Ile Gly Phe Met Trp Ala Leu Glu Ala Val
            355                 360                 365

Lys Asp Lys Ala Ser Lys Ala Pro Phe Asp Gly Asn Leu Ser Val Ser
370                 375                 380

Glu Arg Ile Ala Asn Thr Cys Thr Asp Leu Gly Leu Ile Cys Arg Pro
385                 390                 395                 400

Leu Gly Gln Ser Val Val Leu Cys Pro Pro Phe Ile Leu Thr Glu Ala
            405                 410                 415

Gln Met Asp Glu Met Phe Asp Lys Leu Glu Lys Ala Leu Asp Lys Val
        420                 425                 430

Phe Ala Glu Val Ala
        435                 440                 445

450

<210> SEQ ID NO 77
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 77
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaaa cggtgatggg tgcggcggt gttattccgc cggcgaaagg ctatttttcag     720
gcgattctgc cgatcctgcg caaatatgat attccggtga tcagcgatga agtgatttgc     780
ggctttggcc gtaccggcaa cacctggggc tgcgtgacct atgatttttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt tccgcatggt     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt atgtgggcg    1140
ctggaagcgg tgaaagataa agcgagcaaa gccccgtttg atggcaacct gagcgtgagc    1200
gaacgtattg cgaacacctg caccgatctg ggcctgattt gcagaccggc cggcagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 78
<211> LENGTH: 453

```
<212> TYPE: PRT
<213> ORGANISM: Artificial Sequence
<220> FEATURE:
<223> OTHER INFORMATION: variant of transaminase from V. fluvialis

<400> SEQUENCE: 78
```

| | | | | | | | | | | | | | | |
|---|---|---|---|---|---|---|---|---|---|---|---|---|---|---|
| Met | Asn | Lys | Pro | Gln | Ser | Trp | Glu | Thr | Arg | Ala | Glu | Thr | Tyr | Ser | Leu |
| 1 | | | | 5 | | | | | 10 | | | | | 15 | |

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
                35                  40                  45

Tyr Leu Asp Ala Asn Ser Gly Leu Trp Asn Met Val Ala Gly Phe Asp
    50                  55                  60

His Lys Gly Leu Ile Asp Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Ala Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 79
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 79
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg aacatggtg       180 gcgggctttg atcataaagg cctgattgat gcggcgaaag cgcagtatga acgttttccg       240
ggctatcatg cgttttacgg ccgtatgagc gatcagaccg tgatgctgtc tgaaaaactg       300
gtggaagtga gcccgtttga tagcggccgt gtgttttata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac cgtataacag cgtgtttggc ctgccgctgc cgggctttct gcatctgacc       540 tgccccgcatt attggcgtta tggcgaagaa ggcgaaaccg aagaacagtt tgtcgcgcgt       600
ctggcccgtg aactggaaga aaccattcag aaggaaggcg cggataccat tgcgggcttt       660
tttgcggaac cggtgatggg tgcggccggt gttattccgc cggcgaaagg ctatttccag       720
gcgattctgc cgatcctgcg caaatatgat attccggtga tcagcgatga agtgatttgc       780
ggctttggcc gtaccggcaa cacctggggc tgcgtgacct atgattttac cccggatgcg       840
attattagca gtaaaaacct aaccgcgggt tttttttccgg taggcgcggt gattctgggt       900
ccggaactga gcaaacgtct ggaaaccgcg attgaagcga tcgaagaatt ccgcagggt       960 tttaccgcgg gtggccatcc ggtgggttgt gcgattgcgc tgaaagcgat tgatgtggtg      1020
atgaacgaag cctggccga aaacgtgcgt cgtctggccc gcgttttga agaacgtctg      1080 aaacatattg cggaacgtcc gaacattggc gaatatcgtg gcattggctt atgtggggcg      1140
ctggaagcgg tgaaagataa agcgagcaaa gccccgtttg atggcaacct gagcgtgagc      1200
gaacgtattg cgaacacctg caccgatctg ggcctgattt gcgtccgct gggccagagc      1260 gtggttctgt gcccgccgtt tattctgacc gaagcgcaga tggatgaaat gttcgataaa      1320
ctggaaaaag cgctggataa agtgtttgcg gaagtggcgt aa                         1362

<210> SEQ ID NO 80
<211> LENGTH: 453
<212> TYPE: PRT
<213> ORGANISM: Artificial Sequence
<220> FEATURE:
<223> OTHER INFORMATION: variant of transaminase from V. fluvialis

```
<400> SEQUENCE: 80

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro Gln Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415
```

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 81
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 81

| | | |
|---|---|---:|
| atgaacaaac cgcagagctg ggaaacgcgt gcggaaacct atagcctgta tggctttacc | | 60 |
| gatatgccga gcctgcatca gcgtggcacc gtggtggtga cccatggcga aggcccgtat | | 120 |
| atcgtggatg tgcatggccg tcgttatctg gatgcgaaca gcggcctgtg aacatggtg | | 180 |
| gcgggctttg atcataaagg cctgattgat gcggcgaaag cgcagtatga acgttttccg | | 240 |
| ggctatcatg cgttttacgg ccgtatgagc gatcagaccg tgatgctgtc tgaaaaactg | | 300 |
| gtggaagtga cccgtttga tagcggccgt gtgttttata ccaacagcgg cagcgaagcg | | 360 |
| aacgatacca tggtgaaaat gctgtggttt ctgcatgcgg cggaaggcaa accgcagaaa | | 420 |
| cgtaaaattc tgacccgttg gaacgcgtat catggcgtga ccgcggtgag cgcgagcatg | | 480 |
| accggcaaac cgtataacag cgtgtttggc ctgccgctgc cgggctttct gcatctgacc | | 540 |
| tgcccgcatt attggcgtta tggcgaagaa ggcgaaaccg aagaacagtt tgtcgcgcgt | | 600 |
| ctggcccgtg aactggaaga aaccattcag aaggaaggcg cggataccat tgcgggcttt | | 660 |
| tttgcggaac cggtgatggg tgcgggcggt gttattccgc cggcgaaagg ctattttcag | | 720 |
| gcgattctgc cgatcctgcg caaatatgat attccggtga tcagcgatga agtgatttgc | | 780 |
| ggctttggcc gtaccggcaa cacctggggc tgcgtgacct atgattttac cccggatgcg | | 840 |
| attattagca gtaaaaacct aaccgcgggt tttttttccgg taggcgcggt gattctgggt | | 900 |
| ccggaactga gcaaacgtct ggaaaccgcg attgaagcga tcgaagaatt ccgcatgcg | | 960 |
| tttaccgcgg gcgccatcc ggtgggttgt gcgattgcgc tgaaagcgat tgatgtggtg | | 1020 |
| atgaacgaag gcctggccga aaacgtgcgt cgtctggccc cgcgttttga agaacgtctg | | 1080 |
| aaacatattg cggaacgtcc gaacattggc gaatatcgtg gcattggctt tatgtgggcg | | 1140 |
| ctggaagcgg tgaaagataa agcgagcaaa gccccgtttg atggcaacct gagcgtgagc | | 1200 |
| gaacgtattg cgaacacctg caccgatctg ggcctgattt gccgtccgct gggccagagc | | 1260 |
| gtggttctgt gcccgccgtt tattctgacc gaagcgcaga tggatgaaat gttcgataaa | | 1320 |
| ctggaaaaag cgctggataa agtgtttgcg gaagtggcgt aa | | 1362 |

<210> SEQ ID NO 82
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 82

Met Asn Lys Pro Gln Ser Trp Glu Thr Arg Ala Glu Thr Tyr Ser Leu
1               5                   10                  15

```
Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
         35                  40                  45

Tyr Leu Asp Ala Asn Ser Gly Leu Trp Asn Met Val Ala Gly Phe Asp
     50                  55                  60

His Lys Gly Leu Ile Asp Ala Ala Lys Ala Gln Tyr Glu Arg Phe Pro
 65                  70                  75                  80

Gly Tyr His Ala Phe Tyr Gly Arg Met Ser Asp Gln Thr Val Met Leu
                 85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
             115                 120                 125

Trp Phe Leu His Ala Ala Glu Gly Lys Pro Gln Lys Arg Lys Ile Leu
     130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
             180                 185                 190

Thr Glu Glu Gln Phe Val Ala Arg Leu Ala Arg Glu Leu Glu Glu Thr
         195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
             260                 265                 270

Thr Tyr Asp Phe Thr Pro Asp Ala Ile Ile Ser Ser Lys Asn Leu Thr
         275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Ala
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
             340                 345                 350

Ala Pro Arg Phe Glu Glu Arg Leu Lys His Ile Ala Glu Arg Pro Asn
         355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
             420                 425                 430

Gln Met Asp Glu Met Phe Asp Lys Leu Glu Lys Ala Leu Asp Lys Val
```

Phe Ala Glu Val Ala
    450

<210> SEQ ID NO 83
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 83

| | | | | | |
|---|---|---|---|---|---|
| atgaacaaac | cgcagagctg | ggaaacgcgt | gcggaaacct | atagcctgta | tggctttacc | 60 |
| gatatgccga | gcctgcatca | gcgtggcacc | gtggtggtga | cccatggcga | aggcccgtat | 120 |
| atcgtggatg | tgcatggccg | tcgttatctg | gatgcgaaca | gcggcctgtg | aacatggtg | 180 |
| gcgggctttg | atcataaagg | cctgattgat | gcggcgaaag | cgcagtatga | acgttttccg | 240 |
| ggctatcatg | cgttttacgg | ccgtatgagc | gatcagaccg | tgatgctgtc | tgaaaaactg | 300 |
| gtggaagtga | gcccgtttga | tagcggccgt | gtgttttata | ccaacagcgg | cagcgaagcg | 360 |
| aacgatacca | tggtgaaaat | gctgtggttt | ctgcatgcgg | cggaaggcaa | accgcagaaa | 420 |
| cgtaaaattc | tgacccgttg | aacgcgtat | catggcgtga | ccgcggtgag | cgcgagcatg | 480 |
| accggcaaac | cgtataacag | cgtgtttggc | ctgccgctgc | cgggctttct | gcatctgacc | 540 |
| tgcccgcatt | attggcgtta | tggcgaagaa | ggcgaaaccg | aagaacagtt | tgtcgcgcgt | 600 |
| ctggcccgtg | aactggaaga | aaccattcag | aaggaaggcg | cggataccat | tgcgggcttt | 660 |
| tttgcggaac | cggtgatggg | tgcgggcggt | gttattccgc | cggcgaaagg | ctattttcag | 720 |
| gcgattctgc | cgatcctgcg | caaatatgat | attccggtga | tcagcgatga | agtgatttgc | 780 |
| ggctttggcc | gtaccggcaa | cacctggggc | tgcgtgacct | atgattttac | cccggatgcg | 840 |
| attattagca | gtaaaaacct | aaccgcgggt | tttttttccgg | taggcgcggt | gattctgggt | 900 |
| ccggaactga | gcaaacgtct | ggaaaccgcg | attgaagcga | tcgaagaatt | tccgcatggt | 960 |
| tttaccgcgg | gcggccatcc | ggtgggttgt | gcgattgcgc | tgaaagcgat | tgatgtggtg | 1020 |
| atgaacgaag | gcctggccga | aaacgtgcgt | cgtctggccc | gcgttttga | agaacgtctg | 1080 |
| aaacatattg | cggaacgtcc | gaacattggc | gaatatcgtg | gcattggctt | tatgtgggcg | 1140 |
| ctggaagcgg | tgaaagataa | agcgagcaaa | gccccgtttg | atggcaacct | gagcgtgagc | 1200 |
| gaacgtattg | cgaacacctg | caccgatctg | ggcctgattt | gccgtccgat | tggccagagc | 1260 |
| gtggttctgt | gcccgccgtt | tattctgacc | gaagcgcaga | tggatgaaat | gttcgataaa | 1320 |
| ctggaaaaag | cgctggataa | agtgtttgcg | gaagtggcgt | aa | | 1362 |

<210> SEQ ID NO 84
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 84

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50              55                  60

His Lys Gly Leu Ile Asp Ala Ala Lys Ala Gln Tyr Glu Arg Phe Pro
65              70              75                  80

Gly Tyr His Ala Phe Tyr Gly Arg Met Ser Asp Gln Thr Val Met Leu
                85              90                  95

Ser Glu Lys Leu Val Glu Val Ser Pro Phe Asp Ser Gly Arg Val Phe
            100             105                 110

Tyr Thr Asn Ser Gly Ser Glu Ala Asn Asp Thr Met Val Lys Met Leu
            115             120             125

Trp Phe Leu His Ala Ala Glu Gly Lys Pro Gln Lys Arg Lys Ile Leu
    130             135                 140

Thr Arg Trp Asn Ala Tyr His Gly Val Thr Ala Val Ser Ala Ser Met
145             150             155                 160

Thr Gly Lys Pro Tyr Asn Ser Val Phe Gly Leu Pro Leu Pro Gly Phe
                165             170             175

Leu His Leu Thr Cys Pro His Tyr Trp Arg Tyr Gly Glu Glu Gly Glu
            180             185                 190

Thr Glu Glu Gln Phe Val Ala Arg Leu Ala Arg Glu Leu Glu Glu Thr
        195                 200             205

Ile Gln Lys Glu Gly Ala Asp Thr Ile Ala Gly Phe Phe Ala Glu Pro
    210             215                 220

Val Met Gly Ala Gly Gly Val Ile Pro Pro Ala Lys Gly Tyr Phe Gln
225             230             235                 240

Ala Ile Leu Pro Ile Leu Arg Lys Tyr Asp Ile Pro Val Ile Ser Asp
                245             250                 255

Glu Val Ile Cys Gly Phe Gly Arg Thr Gly Asn Thr Trp Gly Cys Val
            260             265                 270

Thr Tyr Asp Phe Thr Pro Asp Ala Ile Ile Ser Ser Lys Asn Leu Thr
            275             280             285

Ala Gly Phe Phe Pro Val Gly Ala Val Ile Leu Gly Pro Glu Leu Ser
    290             295             300

Lys Arg Leu Glu Thr Ala Ile Glu Ala Ile Glu Glu Phe Pro His Gly
305             310             315                 320

Phe Thr Ala Gly Gly His Pro Val Gly Cys Ala Ile Ala Leu Lys Ala
                325             330                 335

Ile Asp Val Val Met Asn Glu Gly Leu Ala Glu Asn Val Arg Arg Leu
            340             345             350

Ala Pro Arg Phe Glu Glu Arg Leu Lys His Ile Ala Glu Arg Pro Asn
    355             360             365

Ile Gly Glu Tyr Arg Gly Ile Gly Phe Met Trp Ala Leu Glu Ala Val
    370             375             380

Lys Asp Lys Ala Ser Lys Ala Pro Phe Asp Gly Asn Leu Ser Val Ser
385             390             395                 400

Glu Arg Ile Ala Asn Thr Cys Thr Asp Leu Gly Leu Ile Cys Arg Pro
                405             410                 415

Ile Gly Gln Ser Val Val Leu Cys Pro Pro Phe Ile Leu Thr Glu Ala
            420             425             430

Gln Met Asp Glu Met Phe Asp Lys Leu Glu Lys Ala Leu Asp Lys Val
        435             440             445

Phe Ala Glu Val Ala
    450

<210> SEQ ID NO 85
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 85

| | | | | |
|---|---|---|---|---|
| atgaacaaac cgcagagctg ggaaacgcgt gcggaaacct atagcctgta tggctttacc | 60 |
| gatatgccga gcctgcatca gcgtggcacc gtggtggtga cccatggcga aggcccgtat | 120 |
| atcgtggatg tgcatggccg tcgttatctg gatgcgaaca gcggcctgtg gaacatggtg | 180 |
| gcgggctttg atcataaagg cctgattgat gcggcgaaag cgcagtatga acgttttccg | 240 |
| ggctatcatg cgttttacgg ccgtatgagc gatcagaccg tgatgctgtc tgaaaaactg | 300 |
| gtggaagtga gcccgtttga tagcggccgt gtgtttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg gaacgcgtat catggcgtga ccgcggtgag cgcgagcatg | 480 |
| accggcaaac cgtataacag cgtgtttggc ctgccgctgc cgggctttct gcatctgacc | 540 |
| tgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggcaa cacctggggc tgcgtgacct atgattttac cccggatgcg | 840 |
| attattagca gtaaaaacct aaccgcgggt tttttccgg taggcgcggt gattctgggt | 900 |
| ccggaactga gcaaacgtct ggaaaccgcg attgaagcga tcgaagaatt ccgcatggt | 960 |
| tttaccgcgg gcggccatcc ggtgggttgt gcgattgcgc tgaaagcgat tgatgtggtg | 1020 |
| atgaacgaag gcctggccga aaacgtgcgt cgtctggccc gcgttttga agaacgtctg | 1080 |
| aaacatattg cggaacgtcc gaacattggc gaatatcgtg gcattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg ggcctgattt gccgtccgtg cggccagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 86
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 86

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro

```
                65                  70                  75                  80
        Gly Tyr His Ala Phe Tyr Gly Arg Met Ser Asp Gln Thr Val Met Leu
                            85                  90                  95

Ser Glu Lys Leu Val Glu Val Ser Pro Phe Asp Ser Gly Arg Val Phe
                        100                 105                 110

Tyr Thr Asn Ser Gly Ser Glu Ala Asn Asp Thr Met Val Lys Met Leu
                        115                 120                 125

Trp Phe Leu His Ala Ala Glu Gly Lys Pro Gln Lys Arg Lys Ile Leu
                    130                 135                 140

Thr Arg Trp Asn Ala Tyr His Gly Val Thr Ala Val Ser Ala Ser Met
        145                 150                 155                 160

Thr Gly Lys Pro Tyr Asn Ser Val Phe Gly Leu Pro Leu Pro Gly Phe
                            165                 170                 175

Leu His Leu Thr Cys Pro His Tyr Trp Arg Tyr Gly Glu Glu Gly Glu
                        180                 185                 190

Thr Glu Glu Gln Phe Val Ala Arg Leu Ala Arg Glu Leu Glu Glu Thr
                        195                 200                 205

Ile Gln Lys Glu Gly Ala Asp Thr Ile Ala Gly Phe Phe Ala Glu Pro
                    210                 215                 220

Val Met Gly Ala Gly Gly Val Ile Pro Pro Ala Lys Gly Tyr Phe Gln
        225                 230                 235                 240

Ala Ile Leu Pro Ile Leu Arg Lys Tyr Asp Ile Pro Val Ile Ser Asp
                            245                 250                 255

Glu Val Ile Cys Gly Phe Gly Arg Thr Gly Asn Thr Trp Gly Cys Val
                        260                 265                 270

Thr Tyr Asp Phe Thr Pro Asp Ala Ile Ile Ser Ser Lys Asn Leu Thr
                        275                 280                 285

Ala Gly Phe Phe Pro Val Gly Ala Val Ile Leu Gly Pro Glu Leu Ser
                    290                 295                 300

Lys Arg Leu Glu Thr Ala Ile Glu Ala Ile Glu Glu Phe Pro His Gly
        305                 310                 315                 320

Phe Thr Ala Gly Gly His Pro Val Gly Cys Ala Ile Ala Leu Lys Ala
                            325                 330                 335

Ile Asp Val Val Met Asn Glu Gly Leu Ala Glu Asn Val Arg Arg Leu
                        340                 345                 350

Ala Pro Arg Phe Glu Glu Arg Leu Lys His Ile Ala Glu Arg Pro Asn
                        355                 360                 365

Ile Gly Glu Tyr Arg Gly Ile Gly Phe Met Trp Ala Leu Glu Ala Val
                    370                 375                 380

Lys Asp Lys Ala Ser Lys Ala Pro Phe Asp Gly Asn Leu Ser Val Ser
        385                 390                 395                 400

Glu Arg Ile Ala Asn Thr Cys Thr Asp Leu Gly Leu Ile Cys Arg Pro
                            405                 410                 415

Cys Gly Gln Ser Val Val Leu Cys Pro Pro Phe Ile Leu Thr Glu Ala
                        420                 425                 430

Gln Met Asp Glu Met Phe Asp Lys Leu Glu Lys Ala Leu Asp Lys Val
                        435                 440                 445

Phe Ala Glu Val Ala
            450

<210> SEQ ID NO 87
<211> LENGTH: 1362
<212> TYPE: DNA
<213> ORGANISM: Artificial Sequence
```

<220> FEATURE:
<223> OTHER INFORMATION: variant of transaminase from V. fluvialis

<400> SEQUENCE: 87

```
atgaacaaac cgcagagctg ggaaacgcgt gcggaaacct atagcctgta tggctttacc      60
gatatgccga gcctgcatca gcgtggcacc gtggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgtttcatgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgcca ccgcggtgag cgcgagcatg    480
accggcaaac cgtataacag cgtgtttggc ctgccgctgc cgggctttct gcatctgacc    540
tgcccgcatt attggcgtta tgcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgatttac cccgatgcg    840
attattagca gtaaaaacct aaccgcgggt tttttccgg taggcgcggt gattctgggt    900
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg  1020
atgaacgaag gcctggccga aaacgtgcgt cgtctggccc gcgttttga agaacgtctg  1080
aaacatattg cggaacgtcc gaacattggc gaatatcgtg gcattggctt tatgtgggcg  1140
ctggaagcgg tgaaagataa agcgagcaaa gccccgtttg atggcaacct gagcgtgagc  1200
gaacgtattg cgaacacctg caccgatctg ggcctgattt gccgtccgtg tggccagagc  1260
gtggttctgt gcccgccgtt tattctgacc gaggcgcaga tggatgaaat gttcgataaa  1320
ctggaaaaag cgctggataa agtgtttgcg gaagtggcgt aa                     1362
```

<210> SEQ ID NO 88
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 88

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95
```

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
        130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
        210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 89
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 89

-continued

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg      180
gcgggctttg atcataaagg cctgattgat gcggcgaaag cgcagtatga acgttttccg     240
ggctatcatg cgtttcatgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgcca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg cattggcctt atgtgggcg     1140
ctggaagcgg tgaaagataa agcgagcaaa gccccgtttg atggcaacct gagcgtgagc    1200
gaacgtattg cgaacacctg caccgatctg ggcctgatct gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 90
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 90

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125
```

```
Trp Phe Leu His Ala Ala Glu Gly Lys Pro Gln Lys Arg Lys Ile Leu
            130                 135                 140
Thr Arg Trp Asn Ala Tyr His Gly Ala Thr Ala Val Ser Ala Ser Met
145                 150                 155                 160
Thr Gly Lys Pro Tyr Asn Ser Val Phe Gly Pro Leu Pro Gly Phe
                165                 170                 175
Leu His Leu Thr Cys Pro His Tyr Trp Arg Tyr Gly Glu Gly Glu
            180                 185                 190
Thr Glu Glu Gln Phe Val Ala Arg Leu Ala Arg Glu Leu Glu Thr
        195                 200                 205
Ile Gln Lys Glu Gly Ala Asp Thr Ile Ala Gly Phe Phe Ala Glu Pro
210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450
```

<210> SEQ ID NO 91
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 91

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
```

-continued

```
gcgggctttg atcataaagg cctgattgat gcggcgaaag cgcagtatga acgttttccg    240
ggctatcatg cgtttcatgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggctcca ccgcggtgag cgcgagcatg    480
accggcaaac gtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga accattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgatttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt ccgcatggt    960
tttaccgcgg cgccatcc ggtggttgt gcgattgcgc tgaaagcgat tgatgtggtg    1020
atgaacgaag gcctggccga aacgtgcgt cgtctggccc gcgttttga agaacgtctg    1080
aaacatattg cggaacgtcc gaacattggc gaatatcgtg cattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgtg tggccagagc    1260
gtggttctgt gcccgccgtt tattctgacc gaagcgcaga tggatgaaat gttcgataaa    1320
ctggaaaaag cgctggataa agtgtttgcg gaagtggcgt aa    1362
```

<210> SEQ ID NO 92
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 92

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
```

```
            145                 150                 155                 160
Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 93
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 93
atgaacaaac cgcagagctg ggaaacgcgt gcggaaacct atagcctgta tggctttacc      60
gatatgccga gcctgcatca gcgtggcgcc gtggtggtga cccatggcga aggcccgtat     120
atcgtggatg tgcatggccc tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
```

```
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg aacgcgtat catggcgtga ccgcggtgag cgcgagcatg     480
accggcaaac cgtataacag cgtgtttggc ctgccgctgc cgggcttcct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 94
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 94

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Ala Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175
```

```
Leu His Leu Thr Cys Pro His Tyr Trp Arg Tyr Gly Glu Gly Glu
            180                 185                 190

Thr Glu Glu Gln Phe Val Ala Arg Leu Ala Arg Glu Leu Glu Thr
        195                 200                 205

Ile Gln Lys Glu Gly Ala Asp Thr Ile Ala Gly Phe Phe Ala Glu Pro
    210                 215                 220

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 95
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 95
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg cgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgtga ccgcggtgag cgcgagcatg     480
```

```
accggcaaac cgtatagcag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgatttac cccggatgcg    840 attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg   1080 aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacaccctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 96
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 96

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Ala His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Ser Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205
```

Ile Gln Lys Glu Gly Ala Asp Thr Ile Ala Gly Phe Phe Ala Glu Pro
210                 215                 220

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 97
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 97
atgaacaaac cgcagagctg ggaaacgcgt gcggaaacct atagcctgta tggctttacc      60
gatatgccga gcctgcatca gcgtggcacc gcggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600

```
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg    1080 aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                       1362
```

<210> SEQ ID NO 98
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 98

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Ala Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
```

```
            225                 230                 235                 240
Ala Ile Leu Pro Ile Leu Arg Lys Tyr Asp Ile Pro Val Ile Ser Asp
                        245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 99
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 99
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
```

```
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcgg tcgaagaatt ccgcatggt    960 tttaccgcgg cggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg cattggcttt atgtgggcg    1140 ctggaagcgg tgaaagataa agcgagcaaa gccccgtttg atggcaacct gagcgtgagc    1200
gaacgtattg cgaacacctg caccggtctg ggcctgatttt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                      1362
```

<210> SEQ ID NO 100
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 100

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
            275                 280                 285
Ala Gly Phe Phe Pro Val Gly Ala Val Ile Leu Gly Pro Glu Leu Ser
        290                 295                 300
Lys Arg Leu Glu Thr Ala Ile Glu Ala Val Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Gly Leu Gly Leu Ile Cys Arg Pro
                405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450
```

<210> SEQ ID NO 101
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 101

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgcca ccgcggtgag cgcgagcatg     480
accggcaaac cgtataacag cgtgtttggc ctgccgctgc cgggctttct gcatctgacc     540
tgccccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattacac cggcgaaagg ctatttttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt tttttttccgg taggcgcggt gattctgggt     900
```

```
ccggaactga gcaaacgtct ggaaaccgcg attgaagcga tcgaagaatt tccgcatggt   960
tttaccgcgg gcggccatcc ggtgggttgt gcgattgcgc tgaaagcgat tgatgtggtg  1020
atgaacgaag gcctggccga aacgtgcgt cgtctggccc cgcgttttga agaacgtctg  1080
aaacatattg cggaacgtcc gaacattggc gaatatcgtg cattggcctt tatgtgggcg  1140
ctggaagcgg tgaaagataa agcgagcaaa gccccgtttg atggcaacct gagcgtgagc  1200
gaacgtattg cgaacaccctg caccgatctg ggcctgattt gccgtccgtg tggccagagc  1260
gtggttctgt gcccgccgtt tattctgacc gaagcgcaga tggatgaaat gttcgataaa  1320
ctggaaaaag cgctggataa agtgtttgcg gaagtggcgt aa                     1362
```

<210> SEQ ID NO 102
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 102

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

Ala Gly Phe Pro Val Gly Ala Val Ile Leu Gly Pro Glu Leu Ser
            290                 295                 300

Lys Arg Leu Glu Thr Ala Ile Glu Ala Ile Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 103
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 103

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggctcca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttatttcgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
```

```
aaacatattg cggaacgtcc gaacattggc gaatatcgtg gtattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 104
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 104

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Ser Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
```

```
            305                 310                 315                 320
        Phe Thr Ala Gly Gly His Pro Val Gly Cys Ala Ile Ala Leu Lys Ala
                        325                 330                 335
        Ile Asp Val Val Met Asn Glu Gly Leu Ala Glu Asn Val Arg Arg Leu
                        340                 345                 350
        Ala Pro Arg Phe Glu Glu Arg Leu Lys His Ile Ala Glu Arg Pro Asn
                        355                 360                 365
        Ile Gly Glu Tyr Arg Gly Ile Gly Phe Met Trp Ala Leu Glu Ala Val
                        370                 375                 380
        Lys Asp Lys Ala Ser Lys Ala Pro Phe Asp Gly Asn Leu Ser Val Ser
        385                 390                 395                 400
        Glu Arg Ile Ala Asn Thr Cys Thr Asp Leu Gly Leu Ile Cys Arg Pro
                        405                 410                 415
        Leu Gly Gln Ser Val Val Leu Cys Pro Pro Phe Ile Leu Thr Glu Ala
                        420                 425                 430
        Gln Met Asp Glu Met Phe Asp Lys Leu Glu Lys Ala Leu Asp Lys Val
                        435                 440                 445
        Phe Ala Glu Val Ala
            450

<210> SEQ ID NO 105
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 105
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg aacatggtg        180 gcgggctttg atcataaagg cctgattgat gcggcgaaag cgcagtatga acgttttccg       240
ggctatcatg cgtttcatgg ccgtatgagc gatcagaccg tgatgctgtc tgaaaaactg       300
gtggaagtga gcccgtttga tagcggccgt gtgtttttata ccaacagcgg cagcgaagcg      360
aacgatacca tggtgaaaat gctgtggttt ctgcatgcgg cggaaggcaa accgcagaaa       420
cgtaaaattc tgacccgttg gaacgcgtat catggcgcca ccgcggtgag cgcgagcatg       480
accggcaaac cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactggaaga accattcag aaggaaggcg cggataccat tgcgggcttt       660
tttgcggaaa cggtgatggg tggggcggt gttattccac cggcgaaagg ctattttcag       720
gcgattctgc cgatcctgcg caaatatgat attccggtga tcagcgatga agtgatttgc       780
ggctttggcc gtaccggcaa cacctggggc tgcgtgacct atgattttac cccggatgcg       840
attattagca gtaaaaacct aaccgcgggt ttttttccgg taggcgcggt gattctgggt       900
ccggaactga gcaaacgtct ggaaaccgcg attgaagcga tcgaagaatt tccgcatggt       960
tttaccgcgg gcgccatcc ggtgggttgt gcgattgcgc tgaaagcgat tgatgtggtg      1020
atgaacgaag gcctggccga aaacgtgcgt cgtctggccc cgcgttttga agaacgtctg      1080
aaacatattg cggaacgtcc gaacattggc gaatatcgtg gcattggctt atgtgggcg       1140 ctggaagcgg tgaaagataa agcgagcaaa gccccgtttg atggcaacct gagcgtgagc      1200
```

```
gaacgtattg cgaacacctg caccgatctg ggcctgattt gccgtccgat cggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 106
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 106

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Ile Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 107
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 107

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga acgttttccg     240
ggctatcatg cgttttacgg ccgtatgagc gatcagaccg tgacgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgcca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggcggt gttattccgc cggcgaaagg ctatttcag     720
gcgattctgc cgatcctgcg caaatatgat attccggtga tcagcgatga agtgatttgc     780
ggctttggcc gtaccggcaa cacctggggc tgcgtgacct atgatttac cccggatgcg     840
attattagca gtaaaaacct aaccgcgggt tttttccgg taggcgcggt gattctgggt     900
ccggaactga gcaaacgtct ggaaaccgcg attgaagcga tcgaagaatt tccgcatggt     960
tttaccgcgg gcggccatcc ggtgggttgt gcgatagcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccatttg atggcaacct gagcgtgagc    1200
gaacgtattg cgaacacctg caccgatctg ggcctgattt gcgtccgtg tggccagagc    1260
gtggttctgt gcccgccgtt tattctgacc gaagcgcaga tggatgaaat gttcgataaa    1320
ctggaaaaag cgctggataa agtgtttgcg gaagtggcgt aa                      1362
```

<210> SEQ ID NO 108
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 108

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Thr Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365
```

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 109
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 109

| | | |
|---|---|---|
| atgaacaaac cgcagagctg ggaaacgcgt gcggaaacct atagcctgta tggctttacc | 60 |
| gatatgccga gcctgcatca gcgtggcacc gtggtggtga cccatggcga aggcccgtat | 120 |
| atcgtggatg tgcatggccg tcgttatctg gatgcgaaca gcggcctgtg aacatggtg | 180 |
| gcgggctttg atcataaagg cctgattgat gcggcgaaag cgcagtatga acgttttccg | 240 |
| ggctatcatg cgtttcatgg ccgtatgagc gatcagaccg tgatgctgtc tgaaaaactg | 300 |
| gtggaagtga gcccgtttga tagcggccgt gtgttttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg gaacgcgtat catggctcca ccgcggtgag cgcgagcatg | 480 |
| accggcaaac cgtataacag cgtgtttggc ctgccgctgc cgggctttct gcatctgacc | 540 |
| cgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggcaa cacctggggc tgcgtgacct atgatttac cccggatgcg | 840 |
| attattagca gtaaaaacct aaccgcgggt ttttttccgg taggcgcggt gattctgggt | 900 |
| ccggaactga gcaaacgtct ggaaaccgcg attgaagcga tcgaagaatt ccgcatggt | 960 |
| tttaccgcgg gcggccatcc ggtgggttgt gcgattgcgc tgaaagcgat tgatgtggtg | 1020 |
| atgaacgaag gcctggccga aaacgtgcgt cgtctggccc cgcgttttga agaacgtctg | 1080 |
| aaacatattg cggaacgtcc gaacattggc gaatatcgtg cattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg ggcctgattt gcgtccgac cggccagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 110
<211> LENGTH: 453
<212> TYPE: PRT

<213> ORGANISM: Artificial Sequence
<220> FEATURE:
<223> OTHER INFORMATION: variant of transaminase from V. fluvialis

<400> SEQUENCE: 110

| | | | | | | | | | | | | | | |
|---|---|---|---|---|---|---|---|---|---|---|---|---|---|---|
| Met | Asn | Lys | Pro | Gln | Ser | Trp | Glu | Thr | Arg | Ala | Glu | Thr | Tyr | Ser | Leu |
| 1 | | | | 5 | | | | | 10 | | | | | 15 | |

Tyr Gly Phe Thr Asp Met Pro Ser Leu His Gln Arg Gly Thr Val Val
              20                  25                  30

Val Thr His Gly Glu Gly Pro Tyr Ile Val Asp Val His Gly Arg Arg
          35                  40                  45

Tyr Leu Asp Ala Asn Ser Gly Leu Trp Asn Met Val Ala Gly Phe Asp
          50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
              85                  90                  95

Ser Glu Lys Leu Val Glu Val Ser Pro Phe Asp Ser Gly Arg Val Phe
              100                 105                 110

Tyr Thr Asn Ser Gly Ser Glu Ala Asn Asp Thr Met Val Lys Met Leu
              115                 120                 125

Trp Phe Leu His Ala Ala Glu Gly Lys Pro Gln Lys Arg Lys Ile Leu
              130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
              165                 170                 175

Leu His Leu Thr Arg Pro His Tyr Trp Arg Tyr Gly Glu Glu Gly Glu
              180                 185                 190

Thr Glu Glu Gln Phe Val Ala Arg Leu Ala Arg Glu Leu Glu Glu Thr
              195                 200                 205

Ile Gln Lys Glu Gly Ala Asp Thr Ile Ala Gly Phe Phe Ala Glu Pro
              210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
              245                 250                 255

Glu Val Ile Cys Gly Phe Gly Arg Thr Gly Asn Thr Trp Gly Cys Val
              260                 265                 270

Thr Tyr Asp Phe Thr Pro Asp Ala Ile Ile Ser Ser Lys Asn Leu Thr
              275                 280                 285

Ala Gly Phe Phe Pro Val Gly Ala Val Ile Leu Gly Pro Glu Leu Ser
              290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
              325                 330                 335

Ile Asp Val Val Met Asn Glu Gly Leu Ala Glu Asn Val Arg Arg Leu
              340                 345                 350

Ala Pro Arg Phe Glu Glu Arg Leu Lys His Ile Ala Glu Arg Pro Asn
              355                 360                 365

Ile Gly Glu Tyr Arg Gly Ile Gly Phe Met Trp Ala Leu Glu Ala Val
              370                 375                 380

Lys Asp Lys Ala Ser Lys Ala Pro Phe Asp Gly Asn Leu Ser Val Ser

```
                385                 390                 395                 400
Glu Arg Ile Ala Asn Thr Cys Thr Asp Leu Gly Leu Ile Cys Arg Pro
                    405                 410                 415

Thr Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 111
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 111
atgaacaaac cgcagagctg ggaaacgcgt gcggaaacct atagcctgta tggctttacc       60
gatatgccga gcctgcatca gcgtggcacc gtggtggtga cccatggcga aggcccgtat      120
atcgtggatg tgcatggccg tcgttatctg atgcgaaca gcggcctgtg aacatggtg       180
gcgggctttg atcataaagg cctgattgat gcggcgaaag cgcagtatga acgttttccg      240
ggctatcatg cgttttacgg ccgtatgagc gatcagaccg tgatgctgtc tgaaaaactg      300
gtggaagtga gcccgtttga tagcggccgt gtgttttgta ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggcgtga ccgcggtgag cgcgagcatg      480
accggcaaac cgtataacag cgtgtttggc ctgccgctgc cgggctttct gcatctgacc      540
tgccccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctatttttcag     720
gcgattctgc cgatcctgcg caaatatgat attccggtga tcagcgatga agtgatttgc      780
ggctttggcc gtaccggcaa cacctggggc tgcgtgacct atgatttac cccggatgcg      840
attattagca gtaaaaaacct aaccgcgggt tttttttccgg taggcgcggt gattctgggt     900
ccggaactga gcaaacgtct ggaaaccgcg attgaagcga tcgaagaatt ccgcatggt      960
tttaccgcgg cggccatcc ggtgggttgt gcgattgcgc tgaaagcgat tgatgtggtg     1020
atgaacgaag gcctggccga aaacgtgcgt cgtctggccc gcgttttga agaacgtctg     1080
aaacatattg cggaacgtcc gaacattggc gaatatcgtg gcattggctt tatgtgggcg     1140
ctggaagcgg tgagagataa agcgagcaaa gccccgtttg atggcaacct gagcgtgagc     1200
gaacgtattg cgaacacctg caccgatctg ggcctgattt gccgtccgtg tggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362

<210> SEQ ID NO 112
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 112
```

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
            35                  40              45

Tyr Leu Asp Ala Asn Ser Gly Leu Trp Asn Met Val Ala Gly Phe Asp
        50                  55              60

His Lys Gly Leu Ile Asp Ala Ala Lys Ala Gln Tyr Glu Arg Phe Pro
65                  70              75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Cys Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
        210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Arg Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415
```

Cys Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 113
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 113

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgct taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacagc gtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt tttttttccgg taggcgcggt gattctgggt     900
ccggaactga gcaaacgtct ggaaaccgcg attgaagcga tcgaagaatt ccgcatggt     960
tttaccgcgg gcggccatcc ggtgggttgt gcgattgcgc tgaaagcgat tgatgtggtg    1020
atgaacgaag gcctggccga aacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacaccctg caccgatctg gcctgatttt gccgtccgtg tggccagagc    1260
gtggttctgt gcccgccgtt tattctgacc gaagcgcaga tggatgaaat gctcgataaa    1320
ctggaaaaag cgctggataa agtgtttgcg gaagtggcgt aa                       1362
```

<210> SEQ ID NO 114
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 114

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val

-continued

```
                20                  25                  30
Val Thr His Gly Glu Gly Pro Tyr Ile Val Asp Val His Gly Arg Arg
            35                  40                  45
Tyr Leu Asp Ala Asn Ser Gly Leu Leu Asn Met Val Ala Gly Phe Asp
        50                  55                  60
His Lys Gly Leu Ile Asp Ala Ala Lys Ala Gln Tyr Glu Arg Phe Pro
65                  70                  75                  80
Gly Tyr His Ala Phe Tyr Gly Arg Met Ser Asp Gln Thr Val Met Leu
                85                  90                  95
Ser Glu Lys Leu Val Glu Val Ser Pro Phe Asp Ser Gly Arg Val Phe
            100                 105                 110
Tyr Thr Asn Ser Gly Ser Glu Ala Asn Asp Thr Met Val Lys Met Leu
        115                 120                 125
Trp Phe Leu His Ala Ala Glu Gly Lys Pro Gln Lys Arg Lys Ile Leu
    130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
        195                 200                 205
Ile Gln Lys Glu Gly Ala Asp Thr Ile Ala Gly Phe Phe Ala Glu Pro
    210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Cys Gly Gln Ser Val Val Leu Cys Pro Pro Phe Ile Leu Thr Glu Ala
            420                 425                 430
Gln Met Asp Glu Met Leu Asp Lys Leu Glu Lys Ala Leu Asp Lys Val
        435                 440                 445
```

Phe Ala Glu Val Ala
    450

<210> SEQ ID NO 115
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 115

```
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgtt taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaatt gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tgcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacga tgattttac cccggatgcg     840
attattagca gtaaaaacct aaccgcgggt tttttttccgg taggcgcggt gattctgggt     900
ccggaactga gcaaacgtct ggaaaccgcg attgaagcga tcgaagaatt ccgcatggt      960
tttaccgcgg gcggccatcc ggtgggttgt gcgattgcgc tgaaagcgat tgatgtggtg    1020
atgaacgaag gctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg gcctgattt gccgtccgtg tggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 116
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 116

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

```
Tyr Leu Asp Ala Asn Ser Gly Leu Phe Asn Met Val Ala Gly Phe Asp
 50                  55                  60
His Lys Gly Leu Ile Asp Ala Lys Ala Gln Tyr Glu Arg Phe Pro
 65                  70                  75                  80
Gly Tyr His Ala Phe Tyr Gly Arg Met Ser Asp Gln Thr Val Met Leu
                 85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Leu Leu
                115                 120                 125
Trp Phe Leu His Ala Ala Glu Gly Lys Pro Gln Lys Arg Lys Ile Leu
130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
                275                 280                 285
Ala Gly Phe Phe Pro Val Gly Ala Val Ile Leu Gly Pro Glu Leu Ser
                290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Gly Arg Pro Asn
                355                 360                 365
Ile Gly Glu Tyr Arg Gly Ile Gly Phe Met Trp Ala Leu Glu Ala Val
                370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Cys Gly Gln Ser Val Val Leu Cys Pro Pro Phe Ile Leu Thr Glu Ala
                420                 425                 430
Gln Met Asp Glu Met Phe Asp Lys Leu Glu Lys Ala Leu Asp Lys Val
                435                 440                 445
Phe Ala Glu Val Ala
                450
```

<210> SEQ ID NO 117
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 117

```
atgaacaaac cgcagagctg ggaaacgcgt gcggaaacct atagcctgta tggctttacc     60
gatatgccga gcctgcatca gcgtggcacc gtggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggcgtga ccgcggtgag cgcgagcatg    480
accggcaaac gtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaaa cggtgatggg tgcggcggt gttattccgc cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg gttgaagcga ccgaagaatt cccgcacggt    960
ttcaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atgcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt ga                      1362
```

<210> SEQ ID NO 118
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 118

```
Met Asn Lys Pro Gln Ser Trp Glu Thr Arg Ala Glu Thr Tyr Ser Leu
 1               5                  10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80
```

Gly Tyr His Ala Phe Tyr Arg Met Ser Asp Gln Thr Val Met Leu
                85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
                115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
                210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
    290                 295                 300

Lys Arg Leu Glu Thr Ala Val Glu Ala Thr Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 119
<211> LENGTH: 1362
<212> TYPE: DNA
<213> ORGANISM: Artificial Sequence
<220> FEATURE:

<223> OTHER INFORMATION: variant of transaminase from V. fluvialis

<400> SEQUENCE: 119

| | |
|---|---|
| atgaacaaac cgcagagctg ggaaacgcgt gcggaaacct atagcctgta tggctttacc | 60 |
| gatatgccga gcctgcatca gcgtggcacc gtggtggtga cccatggcga aggcccgtat | 120 |
| atcgtggatg tgcatggccg tcgttatctg gatgcgaaca gcggcctgtg gaacatggtg | 180 |
| gcgggctttg atcataaagg cctgattgat gcggcgaaag cgcagtatga acgttttccg | 240 |
| ggctatcatg cgttttacgg ccgtatgagc gatcagaccg tgatgctgtc cgaaaaactg | 300 |
| gtggaagtga gcccgtttga tagcggccgt gtgatttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg gaacgcgtat catggcgtga ccgcggtgag cgcgagcatg | 480 |
| accggcaaac cgtataacag cgtgtttggc ctgccgctgc cgggctttct gcatctgacc | 540 |
| tgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc ggcgaaaagg ctattttcag | 720 |
| gcgattctgc cgatcctgcg caaatatgat attccggtga tcagcgatga agtgatttgc | 780 |
| ggctttggcc gtaccggcaa cacctggggc tgcgtgacct atgattttac cccggatgcg | 840 |
| attattagca gtaaaaacct aaccgcgggt ttttttccgg taggcgcggt gattctgggt | 900 |
| ccggaactga gcaaacgtct ggaaaccgcg attgaagcga tcgaagaact cccgcatggt | 960 |
| tttaccgcgg gcggccatcc ggtgggttgt gcgattgcgc tgaaagcgat tgatgtggtg | 1020 |
| atgaacgaag gcctggccga aaacgtgcgt cgtctggccc cgcgttttga agaacgtctg | 1080 |
| aaacatattg cggaacgtcc gaacattggc gaatatcgtg gcattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg ggcctgattt gcgtccgct gggccagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 120
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 120

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Ile 100                 105                 110
Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Leu Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 121
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 121
atgaacaaac cgcagagctg ggaaacgcgt gcggaaacct atagcctgta tggctttacc    60

```
gatatgccga gcctgcatca gcgtggcacc gtggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cggcatacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgtgg gaacgcgtat catggcgcca ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccac cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgatttac cccggatgcg    840 attattagca gtaaaaacct aaccgcgggt tttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080 aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc    1260 gtggttctgt gcccgccgtt tattctgacc gaagcgcaga tggatgaaat gttcgataaa    1320
ctggaaaaag cgctggataa agtgtttgcg aagtggcgt aa                        1362
```

<210> SEQ ID NO 122  
<211> LENGTH: 453  
<212> TYPE: PRT  
<213> ORGANISM: Artificial Sequence  
<220> FEATURE:  
<223> OTHER INFORMATION: variant of transaminase from V. fluvialis

<400> SEQUENCE: 122

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ala Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125
```

Trp Phe Leu His Ala Ala Glu Gly Lys Pro Gln Lys Arg Lys Ile Leu
130                 135                 140

Thr Arg Gly Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 123
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 123
atgaacaaac cgcagagctg ggaaacgcgt gcggaaacct atagcctgta tggctttacc        60
gatatgccga gcctgcatca gcgtggcacc gtggtggtga cccatggcga aggcccgtat       120
atcgtggatg tgcatggccg tcgttatctg gatgcgaaca gcggcctgtg gaacatggtg       180

```
gcgggctttg atcataaagg cctgattgat gcggcgaaag cgcagtatga gcgttttccg    240
ggctatcatg cgtcttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg aacgcgtat catggctcca ccgcggtgag cgcgagcatg    480
accggcaaac gtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctatttcag    720
gcgattctgc cgatcctgcg caaatatgat attccggtga tcagcgatga agtgatttgc    780
ggctttggcc gtaccggcaa cacctggggc tgcgtgacct atgatttac cccggatgcg    840
attattagca gtaaaaacct aaccgcgggt tttttccgg taggcgcggt gattctgggt    900
ccggaactga gcaaacgtct ggaaaccgcg attgaagcga tcgaagaatt ccgcatggt    960
tttaccgcgg cggccatcc ggtgggttgt gcgattgcgc tgaaagcgat tgatgtggtg   1020
atgaacgaag gcctggccga aacgtgcgt cgtctggccc cgcgttttga agaacgtctg   1080
aaacatattg cggaacgtcc gaacattggc gaatatcgtg cattggcctt tatgtgggcg   1140
ctggaagcgt gaaagataa agcgagcaaa gccccgtttg atggcaacct gagcgtgagc   1200
gaacgtattg cgaacaccctg caccgatctg ggcctgattt gccgtccgct gggccagagc   1260
gtggttctgt gcccgccgtt tattctgacc gaagcgcaga tggatgaaat gttcgataaa   1320
ctggaaaagg cgctggataa agtgtttgcg gaagtggcgt aa                      1362
```

<210> SEQ ID NO 124
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 124

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ser Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160
```

```
Thr Gly Lys Pro Tyr Asn Ser Val Phe Gly Leu Pro Leu Pro Gly Phe
            165                 170                 175
Leu His Leu Thr Cys Pro His Tyr Trp Arg Tyr Gly Glu Glu Gly Glu
        180                 185                 190
Thr Glu Glu Gln Phe Val Ala Arg Leu Ala Arg Glu Leu Glu Glu Thr
    195                 200                 205
Ile Gln Lys Glu Gly Ala Asp Thr Ile Ala Gly Phe Phe Ala Glu Pro
210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 125
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 125
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcaaaca gcggcctgct aacatggtg     180 gcgggctttg atcataaagg cctgattgat gcggcgaaag cgcagtatga acgttttccg     240
ggctatcatg cgtttttcgg ccgtatgagc gatcagaccg tgatgctgtc tgaaaaactg     300
gtggaagtga gcccgtttga tagcggccgt gtgtttata ccaacagcgg cagcgaagcg     360
```

```
aacgatacca tggtgaaaat gctgtggttt ctgcatgcgg cggaaggcaa accgcagaaa    420
cgtaaaattc tgacccgttg gaacgcgtat catggctcca ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattacac cggcgaaagg ctattttcag    720
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg    1020
atgaacgaag gctggccgaa aacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgac cggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 126
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 126

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Leu Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
```

```
            180             185             190
Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
        210                 215                 220

Val Met Gly Ala Gly Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 127
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 127
atgaacaaac cgcagagctg gaaacgcgt gcggaaacct atagcctgta tggctttacc        60
gatatgccga gcctgcatca gcgtggcacc gtggtggtga cccatggcga aggcccgtat      120
atcgtggatg tgcatggccg tcgttatctg gatgcgaaca gcggcctgtg aacatggtg      180 gcgggctttg atcataaagg cctgattgat gcggcgaaag cgcagtatga acgttttccg      240
ggctatcatg cgtcttacgg ccgtatgagc gatcagaccg tgatgctgtc tgaaaaactg      300
gtggaagtga gcccgtttga tagcggccgt gtgtttata ccaacagcgg cagcgaagcg       360
aacgatacca tggtgaaaat gctgtggttt ctgcatgcgg cggaaggcaa accgcagaaa      420
cgtaaaattc tgacccgttg gaacgcgtat catggcgcca ccgcggtgag cgcgagcatg      480
```

-continued

```
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattacac cggcgaaagg ctattttcag      720
gcgattctgc cgatcctgcg caaatatgat attccggtga tcagcgatga agtgatttgc      780
ggctttggcc gtaccggcaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt ccgcatggt      960 tttaccgcgg cggccatcc ggtgggttgt gcgattgcgc tgaaagcgat tgatgtggtg      1020
atgaacgaag gcctggccga aaacgtgcgt cgtctggccc gcgttttga agaacgtctg      1080 aaacatattg cggaacgtcc gaacattggc gaatatcgtg cattggcttt atgtgggcg      1140 ctggaagcgg tgaaagataa agcgagcaaa gccccgtttg atggcaacct gagcgtgagc      1200
gaacgtattg cgaacacctg caccgatctg ggcctgattt gccgtccgct gggccagagc      1260
gtggttctgt gcccgccgtt tattctgacc gaagcgcaga tggatgaaat gttcgataaa      1320
ctggaaaaag cgctggataa agtgtttgcg gaagtggcgt aa                         1362
```

<210> SEQ ID NO 128
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 128

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ser Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205
```

Ile Gln Lys Glu Gly Ala Asp Thr Ile Ala Gly Phe Ala Glu Pro
210                 215                 220

Val Met Gly Ala Gly Val Ile Thr Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Arg Leu Lys His Ile Ala Glu Arg Pro Asn
355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 129
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 129
atgaacaaac cgcagagctg ggaaacgcgt gcggaaacct atagcctgta tggctttacc      60
gatatgccga gcctgcatca gcgtggcacc gtggtggtga cccatggcga aggcccgtat     120
atcgtggatg tgcatggccg tcgttatctg gatgcgaaca gcggcctgat taacatggtg     180
gcgggctttg atcataaagg cctgattgat gcggcgaaag cgcagtatga acgttttccg     240
ggctatcatg cggcacatgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt gtcgcgcgt      600 ctggcccgtg aactggaaga aaccattcag aaggaaggcg cggataccat tgcgggctt      660

-continued

```
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt      960 tttaccgcgg cggccatcc ggtgggttgt gcgattgcgc tgaaagcgat tgatgtggtg     1020
atgaacgaag gcctggccga aaacgtgcgt cgtctggccc cgcgttttga agaacgtctg    1080
aaacatattg cggaacgtcc gaacattggc gaatatcgtg cattggcttt atgtgggcg     1140 ctggaagcgg tgaaagataa agcgagcaaa gccccgtttg atggcaacct gagcgtgagc    1200
gaacgtattg cgaacacctg caccgatctg ggcctgattt gccgtccgtg tggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 130
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 130

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Ile Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Ala His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240
```

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
        260                 265                 270

Thr Tyr Asp Phe Thr Pro Asp Ala Ile Ile Ser Ser Lys Asn Leu Thr
    275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 131
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 131
atgaacaaac cgcagagctg ggaaacgcgt gcggaaacct atagcctgta tggctttacc    60
gatatgccga gcctgcatca gcgtggcacc gtggtggtga cccatggcga aggcccgtat   120
atcgtggatg tgcatggccg tcgttatctg gatgcgaaca gcggcctgtg aacatggtg   180 gcgggctttg atcataaagg cctgattgat gcggcgaaag cgcagtatga acgttttccg   240
ggctatcatg cggcatacgg ccgtatgagc gatcagaccg tgatgctgtc tgaaaaactg   300
gtggaagtga gcccgtttga tagcggccgt gtgtttttata ccaacagcgg cagcgaagcg   360
aacgatacca tggtgaaaat gctgtggttt ctgcatgcgg cggaaggcaa accgcagaaa   420
cgtaaaattc tgacccgttg aacgcgtat catggctcga ccgcggtgag cgcgagcatg   480
accggcaaac cgtataacag cgtgtttggc ctgccgctgc cgggctttct gcatctgacc   540
tgcccgcatt attggcgtta tggcgaagaa ggcgaaaccg aagaacagtt tgtcgcgcgt   600
ctggcccgtg aactggaaga aaccattcag aaggaaggcg cggataccat tgcgggcttt   660
tttgcggaaa cggtgatggg tgcggcggt gttattccgc cggcgaaagg ctattttcag   720
gcgattctgc cgatcctgcg caaatatgat attccggtga tcagcgatga agtgatttgc   780

```
ggctttggcc gtaccggcaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt ccgcatggt    960 tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg cattggcctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gcgtccgag cggccagagc   1260 gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 132
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 132

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Ala Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
```

```
            260                265                270
Thr Tyr Asp Phe Thr Pro Asp Ala Ile Ile Ser Ser Lys Asn Leu Thr
            275                280                285
Ala Gly Phe Phe Pro Val Gly Ala Val Ile Leu Gly Pro Glu Leu Ser
            290                295                300
Lys Arg Leu Glu Thr Ala Ile Glu Ala Ile Glu Glu Phe Pro His Gly
305                310                315                320
Phe Thr Ala Gly Gly His Pro Val Gly Cys Ala Ile Ala Leu Lys Ala
                325                330                335
Ile Asp Val Val Met Asn Glu Gly Leu Ala Glu Asn Val Arg Arg Leu
                340                345                350
Ala Pro Arg Phe Glu Glu Arg Leu Lys His Ile Ala Glu Arg Pro Asn
            355                360                365
Ile Gly Glu Tyr Arg Gly Ile Gly Phe Met Trp Ala Leu Glu Ala Val
            370                375                380
Lys Asp Lys Ala Ser Lys Ala Pro Phe Asp Gly Asn Leu Ser Val Ser
385                390                395                400
Glu Arg Ile Ala Asn Thr Cys Thr Asp Leu Gly Leu Ile Cys Arg Pro
                405                410                415
Ser Gly Gln Ser Val Val Leu Cys Pro Pro Phe Ile Leu Thr Glu Ala
                420                425                430
Gln Met Asp Glu Met Phe Asp Lys Leu Glu Lys Ala Leu Asp Lys Val
            435                440                445
Phe Ala Glu Val Ala
    450

<210> SEQ ID NO 133
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 133
atgaacaaac cgcagagctg ggaaacgcgt gcggaaacct atagcctgta tggttttacc    60
gatatgccga gcctgcatca gcgtggcacc gtggtggtga cccatggcga aggcccgtat   120
atcgtggatg tgcatggccg tcgttatctg gatgcgaaca gcggcctgag caacatggtg   180
gcgggctttg atcataaagg cctgattgat gcggcgaaag cgcagtatga acgttttccg   240
ggctatcatg cgttttacgg ccgtatgagc gatcagaccg tgatgctgtc tgaaaaactg   300
gtggaagtga gcccgtttga tagcggccgt gtgttttata ccaacagcgg cagcgaagcg   360
aacgatacca tggtgaaaat gctgtggttt ctgcatgcgg cggaaggcaa accgcagaaa   420
cgtaaaattc tgacccgttg aacgcgtat catggcgtga ccgcggtgag cgcgagcatg   480
accggcaaac cgtataacag cgtgtttggc ctgccgctgc cgggctttct gcatctgacc   540
tgcccgcatt attggcgtta tggcgaagaa ggcgaaaccg aagaacagtt tgtcgcgcgt   600
ctggcccgtg aactggaaga aaccattcag aaggaaggcg cggataccat tgcgggcttt   660
tttgcggaac cggtgatggg tgcggcggt gttattctgc cggcgaaagg ctatttcag    720
gcgattctgc cgatcctgcg caaatatgat attccggtga tcagcgatga agtgatttgc   780
ggctttggcc gtaccggtaa cacctggggc tgcgtgacct atgattttac cccggatgcg   840
attattagca gtaaaaacct aaccgcgggt ttttttccgg taggcgcggt gattctgggt   900
ccggaactga gcaaacgtct ggaaaccgcg attgaagcga tcgaagaatt ccgcatggt   960
```

-continued

```
tttaccgcgg cggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccggt gggccagagc    1260 gtggttctgt gcccgccgtt tattctgacc gaagcgcaga tggatgaaat gttcgataaa    1320
ctggaaaaag cgctggataa agtgtttgcg gaagtggcgt aa                        1362
```

<210> SEQ ID NO 134
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 134

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ser Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Leu Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

```
Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Val Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 135
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 135
atgaacaaac cgcagagctg ggaaacgcgt gcggaaacct atagcctgta tggttttacc        60
gatatgccga gcctgcatca gcgtggcacc gtggtggtga cccatggcga aggcccgtat       120
atcgtggatg tgcatggccg tcgttatctg gatgcgaaca gcggcctgag caacatggtg       180
gcgggctttg atcataaagg cctgattgat gcggcgaaag cgcagtatga cgttttccg        240 ggctatcatg cgtttggcgg ccgtatgagc gatcagaccg tgatgctgtc tgaaaaactg       300
gtggaagtga gcccgtttga tagcggccgt gtgtttata ccaacagcgg cagcgaagcg       360
aacgatacca tggtgaaaat gctgtggttt ctgcatgcgg cggaaggcaa accgcagaaa       420
cgtaaaattc tgacccgttg gaacgcgtat catggcgtga ccgcggtgag cgcgagcatg       480
accggcaaac cgtataacag cgtgtttggc ctgccgctgc cgggctttct gcatctgacc       540
tgcccgcatt attggcgtta tggcgaagaa ggcgaaaccg aagaacagtt tgtcgcgcgt       600
ctggcccgtg aactggaaga accattcag aaggaaggcg cggataccat tgcgggcttt       660
tttgcggaaa cggtgatggg tgcggcggt gttattccgc cggcgaaagg ctattttcag       720
gcgattctgc cgatcctgcg caaatatgat attccggtga tcagcgatga agtgatttgc       780
ggctttggcc gtaccggtaa cacctggggc tgcgtgacct atgatttac cccggatgcg       840 attattagca gtaaaaacct aaccgcgggt tttttccgg taggcgcggt gattctgggt       900
ccggaactga gcaaacgtct ggaaaccgcg attgaagcga tcgaagaatt tccgcatggt       960
tttaccgcgg gcggccatcc ggtgggttgt gcgattgcgc tgaaagcgat tgatgtggtg      1020
atgaacgaag gcctggccga aaacgtgcgt cgtctggccc cgcgttttga agaacgtctg      1080
```

```
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacaccct gcaccgatctg ggcctgattt gccgtccgtg cggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 136
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 136

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ser Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Gly Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320
```

```
Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 137
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 137
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaaa ccggtgatgg gtggcggcgg ttattccgc cggcgaaagg ctatttcag     720 gcgattctgc cgatcctgcg caaatatgat attccggtga tcagcgatga agtgatttgc     780
ggctttggcc gtaccggtaa cacctggggc tgcgtgacct atgatttac cccggatgcg     840 attattagca gtaaaaaccct aaccgcgggt ttttttccgg taggcgcggt gattctgggt     900
ccggaactga gcaaacgtct ggaaaccgcg attgaagcga tcgaagaact gccgcatggt     960
tttaccgcgg gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacaccct gaccgatctg ggcctgattt gccgtccgtg cggccagagc    1260
```

```
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 138
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 138

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Leu Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
```

```
                 340                 345                 350
Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 139
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 139
atgaacaaac cgcagagctg gaaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctggc gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttt gaacgcgtat catggcagca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattccgc ggcgaaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt tggccatggt     960
tttaccgcgg gcggccatcc ggtgggttgt gcgattgcgc tgaaagcgat tgatgtggtg    1020
atgaacgaag gcctggccga aacgtgcgt cgtctggccc gcgttttga agaacgtctg    1080 aaacatattg cggaacgtcc gaacattggc aatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gcgtccgct gggccagagc    1260 gtggttctgt gccgccgtt tattctgacc gaagcgcaga tggatgaaat gttcgataaa    1320
ctggaaaaag cgctggataa agtgtttgcg gaagtggcgt aa                      1362
```

-continued

```
<210> SEQ ID NO 140
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 140

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ala Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Gly His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365
```

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 141
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 141

| | | |
|---|---|---|
| atgaacaaac cgcagagctg ggaaacgcgt gcggaaacct atagcctgta tggttttacc | 60 |
| gatatgccga gcctgcatca gcgtggcacc gtggtggtga cccatggcga aggcccgtat | 120 |
| atcgtggatg tgcatggccg tcgttatctg atgcgaaca gcggcctgtt aacatggtg | 180 |
| gcgggctttg atcataaagg cctgattgat gcggcgaaag cgcagtatga acgttttccg | 240 |
| ggctatcatg cgtttcatgg ccgtatgagc gatcagaccg tgatgctgtc tgaaaaactg | 300 |
| gtggaagtga gcccgtttga tagcggccgt gtgttttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg aacgcgtat catggccaga ccgcggtgag cgcgagcatg | 480 |
| accggcaaac gtataacag cgtgtttggc ctgccgctgc cgggctttct gcatctgacc | 540 |
| tgccccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggtaa cacctggggc tgcgtgacct atgatttac cccggatgcg | 840 |
| attattagca gtaaaaacct aaccgcgggt tttttttccgg taggcgcggt gattctgggt | 900 |
| ccggaactga gcaaacgtct ggaaaccgcg attgaagcga tcgaagaatt ccgcatggt | 960 |
| tttaccgcgg cgggccatcc ggtgggttgt gcgattgcgc tgaaagcgat tgatgtggtg | 1020 |
| atgaacgaag gcctggccga aaacgtgcgt cgtctggccc cgcgttttga agaacgtctg | 1080 |
| aaacatattg cggaacgtcc gaacattggc gaatatcgtg gcattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg ggcctgattt gcgtccgct gggccagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 142
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 142

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Gln Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400
```

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 143
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 143

| | | |
|---|---|---|
| atgaacaaac cgcagagctg ggaaacgcgt gcggaaacct atagcctgta tggttttacc | 60 |
| gatatgccga gcctgcatca gcgtggcacc gtggtggtga cccatggcga aggcccgtat | 120 |
| atcgtggatg tgcatggccg tcgttatctg atgcgaaca gcggcctgat taacatggtg | 180 |
| gcgggctttg atcataaagg cctgattgat gcggcgaaag cgcagtatga acgttttccg | 240 |
| ggctatcatg cgttttttgg ccgtatgagc gatcagaccg tgatgctgtc tgaaaaactg | 300 |
| gtggaagtga gcccgtttga tagcggccgt gtgttttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg aacgcgtat catggcgtga ccgcggtgag cgcgagcatg | 480 |
| accggcaaac cgtataacag cgtgtttggc ctgccgctgc cgggcttttct gcatctgacc | 540 |
| tgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggtaa cacctggggc tgcgtgacct atgattttac cccggatgcg | 840 |
| attattagca gtaaaaacct aaccgcgggt tttttttccgg taggcgcggg gattctgggt | 900 |
| ccggaactga gcaaacgtct ggaaaccgcg attgaagcga tcgaagaatt ccgcatgcg | 960 |
| tttaccgcgg cggccatcc ggtgggttgt gcgattgcgc tgaaagcgat tgatgtggtg | 1020 |
| atgaacgaag gctggccga aaacgtgcgt cgtctggccc gcgtttttga agaacgtctg | 1080 |
| aaacatattg cggaacgtcc gaacattggc gaatatcgtg gcattggctt tatgtgggcg | 1140 |
| ctggaagcgt gaaagataa agcgagcaaa gccccgtttg atggcaacct gagcgtgagc | 1200 |
| gaacgtattg cgaacacctg caccgatctg ggcctgattt gccgtccgct gggccagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 144
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 144

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ile Asn Met Val Ala Gly Phe Asp
    50              55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Ala
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Gly Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
```

```
                420             425             430
Gln Met Asp Glu Met Phe Asp Lys Leu Glu Lys Ala Leu Asp Lys Val
         435                 440                 445

Phe Ala Glu Val Ala
    450

<210> SEQ ID NO 145
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 145
atgaacaaac cgcagagctg ggaaacgcgt gcggaaacct atagcctgta tggttttacc       60
gatatgccga gcctgcatca gcgtggcacc gtggtggtga cccatggcga aggcccgtat      120
atcgtggatg tgcatggccg tcgttatctg gatgcgaaca gcggcctgtt taacatggtg      180
gcgggctttg atcataaagg cctgattgat gcggcgaaag cgcagtatga acgttttccg      240
ggctatcatg cgttttttgg ccgtatgagc gatcagaccg tgatgctgtc tgaaaaactg      300
gtggaagtga gcccgtttga tagcggccgt gtgttttata ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggccaga ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga accattcag aaggaaggcg cggataccat tgcgggcttt      660
tttgcggaaa cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt tcgcatggt       960 tttaccgcgg gcggccatcc ggtgggttgt gcgattgcgc tgaaagcgat tgatgtggtg     1020
atgaacgaag gcctggccga aaacgtgcgt cgtctggccc gcgttttga agaacgtctg      1080 aaacatattg cggaacgtcc gaacattggc gaatatcgtg gcattggctt atgtgggcg      1140 ctggaagcgg tgaaagataa agcgagcaaa gccccgtttg atggcaacct gagcgtgagc     1200
gaacgtattg cgaacaccctg caccgatctg ggcctgattt gccgtccgct gggccagagc    1260
gtggttctgt gcccgccgtt tattctgacc gaagcgcaga tggatgaaat gttcgataaa     1320
ctggaaaaag cgctggataa agtgtttgcg gaagtggcgt aa                        1362

<210> SEQ ID NO 146
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 146

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30
```

Val Thr His Gly Glu Gly Pro Tyr Ile Val Asp Val His Gly Arg Arg
         35                  40                  45

Tyr Leu Asp Ala Asn Ser Gly Leu Phe Asn Met Val Ala Gly Phe Asp
 50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                 85                  90                  95

Ser Glu Lys Leu Val Glu Val Ser Pro Phe Asp Ser Gly Arg Val Phe
             100                 105                 110

Tyr Thr Asn Ser Gly Ser Glu Ala Asn Asp Thr Met Val Lys Met Leu
             115                 120                 125

Trp Phe Leu His Ala Ala Glu Gly Lys Pro Gln Lys Arg Lys Ile Leu
         130                 135                 140

Thr Arg Trp Asn Ala Tyr His Gly Gln Thr Ala Val Ser Ala Ser Met
145                 150                 155                 160

Thr Gly Lys Pro Tyr Asn Ser Val Phe Gly Leu Pro Leu Pro Gly Phe
                 165                 170                 175

Leu His Leu Thr Cys Pro His Tyr Trp Arg Tyr Gly Glu Glu Gly Glu
             180                 185                 190

Thr Glu Glu Gln Phe Val Ala Arg Leu Ala Arg Glu Leu Glu Glu Thr
             195                 200                 205

Ile Gln Lys Glu Gly Ala Asp Thr Ile Ala Gly Phe Phe Ala Glu Pro
         210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                 245                 250                 255

Glu Val Ile Cys Gly Phe Gly Arg Thr Gly Asn Thr Trp Gly Cys Val
             260                 265                 270

Thr Tyr Asp Phe Thr Pro Asp Ala Ile Ser Ser Lys Asn Leu Thr
             275                 280                 285

Ala Gly Phe Phe Pro Val Gly Ala Val Ile Leu Gly Pro Glu Leu Ser
         290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                 325                 330                 335

Ile Asp Val Val Met Asn Glu Gly Leu Ala Glu Asn Val Arg Arg Leu
             340                 345                 350

Ala Pro Arg Phe Glu Glu Arg Leu Lys His Ile Ala Glu Arg Pro Asn
             355                 360                 365

Ile Gly Glu Tyr Arg Gly Ile Gly Phe Met Trp Ala Leu Glu Ala Val
         370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                 405                 410                 415

Leu Gly Gln Ser Val Val Leu Cys Pro Pro Phe Ile Leu Thr Glu Ala
             420                 425                 430

Gln Met Asp Glu Met Phe Asp Lys Leu Glu Lys Ala Leu Asp Lys Val
             435                 440                 445

```
Phe Ala Glu Val Ala
    450
```

<210> SEQ ID NO 147
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 147

```
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctggc gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggctgca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcggccggt gttattccgc cggcgaaagg ctatttttcag    720
gcgattctgc cgatcctgcg caaatatgat attccggtga tcagcgatga agtgatttgc     780
ggctttggcc gtaccggtaa cacctgggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt      960
ctgaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg     1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg gcctgatttt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 148
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 148

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Ala Asn Met Val Ala Gly Phe Asp
```

```
              50                  55                  60
His Lys Gly Leu Ile Asp Ala Lys Ala Gln Tyr Glu Arg Phe Pro
 65                  70                  75                  80

Gly Tyr His Ala Phe Tyr Gly Arg Met Ser Asp Gln Thr Val Met Leu
                     85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
                115                 120                 125

Trp Phe Leu His Ala Ala Glu Gly Lys Pro Gln Lys Arg Lys Ile Leu
130                 135                 140

Thr Arg Trp Asn Ala Tyr His Gly Cys Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
                195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
                290                 295                 300

Lys Arg Leu Glu Thr Ala Ile Glu Ala Ile Glu Glu Phe Pro His Gly
305                 310                 315                 320

Leu Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
                370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 149
```

<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 149

| | |
|---|---:|
| atgaacaaac cgcagagctg gaaaacgcgt gcggaaacct atagcctgta tggttttacc | 60 |
| gatatgccga gcctgcatca gcgtggcacc gtggtggtga cccatggcga aggcccgtat | 120 |
| atcgtggatg tgcatggccg tcgttatctg gatgcgaaca gcggcctgtg gaacatggtg | 180 |
| gcgggctttg atcataaagg cctgattgat gcggcgaaag cgcagtatga acgttttccg | 240 |
| ggctatcatg cgttttttgg ccgtatgagc gatcagaccg tgatgctgtc tgaaaaactg | 300 |
| gtggaagtga gcccgtttga tagcggccgt gtgttttata ccaacagcgg cagcgaagcg | 360 |
| aacgatacca tggtgaaaat gctgtggttt ctgcatgcgg cggaaggcaa accgcagaaa | 420 |
| cgtaaaattc tgacccgttg gaacgcgtat catggcgtga ccgcggtgag cgcgagcatg | 480 |
| accggcaaac cgtataacag cgtgtttggc ctgccgctgc cgggctttct gcatctgacc | 540 |
| tgcccgcatt attggcgtta tggcgaagaa ggcgaaaccg aagaacagtt tgtcgcgcgt | 600 |
| ctggcccgtg aactggaaga aaccattcag aaggaaggcg cggataccat tgcgggcttt | 660 |
| tttgcggaac cggtgatggg tgcgggcggt gttattccgc cggcgaaagg ctattttcag | 720 |
| gcgattctgc cgatcctgcg caaatatgat attccggtga tcagcgatga agtgatttgc | 780 |
| ggctttggcc gtaccggtaa cacctggggc tgcgtgacct atgatttac cccggatgcg | 840 |
| attattagca gtaaaaacct aaccgcgggt tttttttccgg taggcgcggt gattctgggt | 900 |
| ccggaactga gcaaacgtct ggaaaccgcg attgaagcga tcgaagaatt tcgtcatggt | 960 |
| tttaccgcgg gcggccatcc ggtgggttgt gcgattgcgc tgaaagcgat tgatgtggtg | 1020 |
| atgaacgaag gcctggccga aaacgtgcgt cgtctggccc cgcgttttga gaacgtctg | 1080 |
| aaacatattg cggaacgtcc gaacattggc gaatatcgtg gcattggctt tatgtgggcg | 1140 |
| ctggaagcgg tgaaagataa agcgagcaaa gccccgtttg atggcaacct gagcgtgagc | 1200 |
| gaacgtattg cgaacacctg caccgatctg gcctgatttt gcgtccggc gggcagagc | 1260 |
| gtggttctgt gcccgccgtt tattctgacc gaagcgcaga tggatgaaat gttcgataaa | 1320 |
| ctggaaaaag cgctggataa agtgtttgcg gaagtggcgt aa | 1362 |

<210> SEQ ID NO 150
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 150

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
            85                  90                  95

Ser Glu Lys Leu Val Glu Val Ser Pro Phe Asp Ser Gly Arg Val Phe
        100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
        210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Arg His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Ala Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 151
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 151

```
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgtga ccgcggtgag cgcgagcatg     480
accggcaaac cgtataacag cgtgtttggc ctgccgctgc cgggcttttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tggcggcggt gttattccgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt tggccatggt     960
tttaccgcgg cgggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaaccct gagcgtgagc    1200
gaacgtattg cgaacacctg caccgatctg ggcctgattt gccgtccgtg cggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 152
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 152

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110
```

```
Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Gly His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 153
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 153
atgaacaaac cgcagagctg ggaaacgcgt gcggaaacct atagcctgta tggttttacc      60
```

```
gatatgccga gcctgcatca gcgtggcacc gtggtggtga cccatggcga aggcccgtat      120
atcgtggatg tgcatggccg tcgttatctg gatgcgaaca gcggcctgtg caacatggtg      180
gcgggctttg atcataaagg cctgattgat gcggcgaaag cgcagtatga acgttttccg      240
ggctatcatg cgtttagcgg ccgtatgagc gatcagaccg tgatgctgtc tgaaaaactg      300
gtggaagtga gcccgtttga tagcggccgt gtgttttata ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggcgtga ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt ccgcatggt      960
tttaccgcgg cggccatcc ggtgggttgt gcgattgcgc tgaaagcgat tgatgtggtg     1020
atgaacgaag gctggccga aaacgtgcgt cgtctggccc gcgtttttga agaacgtctg     1080
aaacatattg cggaacgtcc gaacattggc gaatatcgtg cattggcctt tatgtgggcg     1140
ctggaagcgg tgaaagataa agcgagcaaa gccccgtttg atggcaacct gagcgtgagc     1200
gaacgtattg cgaacacctg caccgatctg ggcctgattt gccgtccgac cggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 154
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 154

```
Met Asn Lys Pro Gln Ser Trp Glu Thr Arg Ala Glu Thr Tyr Ser Leu
 1               5                  10                  15

Tyr Gly Phe Thr Asp Met Pro Ser Leu His Gln Arg Gly Thr Val Val
             20                  25                  30

Val Thr His Gly Glu Gly Pro Tyr Ile Val Asp Val His Gly Arg Arg
         35                  40                  45

Tyr Leu Asp Ala Asn Ser Gly Leu Cys Asn Met Val Ala Gly Phe Asp
     50                  55                  60

His Lys Gly Leu Ile Asp Ala Ala Lys Ala Gln Tyr Glu Arg Phe Pro
 65                  70                  75                  80

Gly Tyr His Ala Phe Ser Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
```

-continued

```
             130                 135                 140
Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 155
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 155

| | | |
|---|---|---|
| atgaacaaac cgcagagctg gaaacgcgt gcggaaacct atagcctgta tggttttacc | | 60 |
| gatatgccga gcctgcatca gcgtggcacc gtggtggtga cccatggcga aggcccgtat | | 120 |
| atcgtggatg tgcatggccg tcgttatctg gatgcgaaca gcggcctgtg aacatggtg | | 180 |
| gcgggctttg atcataaagg cctgattgat gcggcgaaag cgcagtatga acgttttccg | | 240 |

```
ggctatcatg cgttttttgg ccgtatgagc gatcagaccg tgatgctgtc tgaaaaactg      300
gtggaagtga gcccgtttga tagcggccgt gtgtttata  ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggctgca ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt tttttccgg  taggcgcggc gattctgggt      900
ccggaactga gcaaacgtct ggaaaccgcg attgaagcga tcgaagaatt ccgcatggt       960 tttaccgcgg gcggccatcc ggtgggttgt gcgattgcgc tgaaagcgat tgatgtggtg     1020
atgaacgaag gcctggccga aaacgtgcgt cgtctggccc gcgttttga  agaacgtctg     1080 aaacatattg cggaacgtcc gaacattggc gaatatcgtg gcattggctt tatgtgggcg     1140
ctggaagcgg tgaaagataa agcgagcaaa gccccgtttg atggcaacct gagcgtgagc     1200
gaacgtattg cgaacacctg caccgatctg ggcctgattt gccgtccgct gggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 156
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 156

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Ala Val Ser Ala Ser Met
145                 150                 155                 160
```

```
Thr Gly Lys Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
        180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
        210                 215                 220

Val Met Gly Ala Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Ala Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Gly Arg Pro Asn
        355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 157
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 157
atgaacaaac cgcagagctg gaaacgcgt gcggaaacct atagcctgta tggttttacc      60
gatatgccga gcctgcatca gcgtggcacc gtggtggtga cccatggcga aggcccgtat    120
atcgtggatg tgcatggccg tcgttatctg gatgcgaaca gcggcctgtg aacatggtg    180 gcgggctttg atcataaagg cctgattgat gcggcgaaag cgcagtatga acgttttccg    240
ggctatcatg cgtttagcgg ccgtatgagc gatcagaccg tgatgctgtc tgaaaaactg    300
gtggaagtga gcccgtttga tagcggccgt gtgttttata ccaacagcgg cagcgaagcg    360
```

```
aacgatacca tggtgaaaat gctgtggttt ctgcatgcgg cggaaggcaa accgcagaaa    420
cgtaaaattc tgacccgttg aacgcgtat catggcacca ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctatttttcag    720 gcgattctgc cgatcctgcg caaatatgat attccggtga tcagcgatga agtgatttgc    780
ggctttggcc gtaccggtaa cacctggggc tgtgtgacct atgatttttac cccggatgcg    840 attattagca gtaaaaacct aaccgcgggt ttttttccgg taggcgcggc gattctgggt    900
ccggaactga gcaaacgtct ggaaaccgcg attgaagcga tcgaagaatt tccgcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gcgtccgct gggccagagc   1260 gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 158
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 158

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ser Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Thr Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

```
Thr Glu Glu Gln Phe Val Ala Arg Leu Ala Arg Glu Leu Glu Glu Thr
            195                 200                 205
Ile Gln Lys Glu Gly Ala Asp Thr Ile Ala Gly Phe Phe Ala Glu Pro
    210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
            260                 265                 270
Thr Tyr Asp Phe Thr Pro Asp Ala Ile Ile Ser Ser Lys Asn Leu Thr
        275                 280                 285
Ala Gly Phe Phe Pro Val Gly Ala Ala Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 159
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 159
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca cgggcctgtg aacatggtg     180 gcgggctttg atcataaagg cctgattgat gcggcgaaag cgcagtatga cgttttccg     240 ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcagca ccgcgtgag cgcgagcatg     480 accggcaaaac cgtataacag cgtgtttggc ctgccgctgc cgggctttct gcatctgacc     540
```

```
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaatt tcgtcatggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgga aggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 160
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 160

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
```

```
        210                 215                 220
Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Arg His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Glu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 161
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 161
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg atgcgaaca gcggcctgtg aacatggtg     180 gcgggctttg atcataaagg cctgattgat gcggcgaaag cgcagtatga acgttttccg     240
ggctatcatg cgtttcatgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
```

-continued

```
tttgcggaac cggtgatggg tgcgggcggt gttattctgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt ccgcatggt      960 tttaccgcgg gcggccatcc ggtgggttgt gcgattgcgc tgaaagcgat tgatgtggtg     1020
atgaacgaag gcctggccga aacgtgcgt cgtctggccc cgcgttttga agaacgtctg     1080
aaacatattg cggaacgtcc gaacattggc gaatatcgtg cattggctt tatgtgggcg     1140 ctggaagcgg tgaaagataa agcgagcaaa gccccgtttg atggcaacct gagcgtgagc     1200
gaacgtattg cgaacacctg caccgatctg ggcctgattt gccgtccggc gggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 162
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 162

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe His Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Leu Pro Ala Lys Gly Tyr Phe Gln
225                 230                 235                 240
```

```
Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
        260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Phe Pro His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Ala Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 163
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 163
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg aacgcgtat catggctgca ccgcgtgag cgcgagcatg     480 accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660 tttgcggaaac cggtgatggg tgcggcggt gttattctgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
```

```
attattagca gtaaaaacct aaccgcgggt ttttttccgg taggcgcggt gattctgggt    900
ccggaactga gcaaacgtct ggaaaccgcg attgaagcga tcgaagaatt tcgtcatggt    960
tttaccgcgg gcggccatcc ggtgggttgt gcgattgcgc tgaaagcgat tgatgtggtg   1020
atgaacgaag gcctggccga aaacgtgcgt cgtctggccc gcgttttga agaacgtctg   1080 aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 164
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 164

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Leu Pro Ala Lys Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Arg His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 165
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 165
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg caacatggtg     180
gcgggctttg atcataaagg cctgattgat gcggcgaaag cgcagtatga acgttttccg     240
ggctatcatg cgtttgcggg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgccccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc ggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgatttac cccggatgcg     840
attattagca gtaaaaacct aaccgcgggt tttttttccgg taggcgcggt gattctgggt     900
ccggaactga gcaaacgtct ggaaaccgcg attgaagcga tcgaagaact gccgcatggt     960

```
tttaccgcgg cggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gcattggctt atgtgggcg    1140 ctggaagcgg tgaaagataa agcgagcaaa gccccgtttg atggcaacct gagcgtgagc    1200
gaacgtattg cgaacaccctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                      1362
```

<210> SEQ ID NO 166
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 166

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Cys Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Ala Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
```

```
                290                 295                 300
Lys Arg Leu Glu Thr Ala Ile Glu Ala Ile Glu Leu Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
                355                 360                 365

Ile Gly Glu Tyr Arg Gly Ile Gly Phe Met Trp Ala Leu Glu Ala Val
                370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450
```

```
<210> SEQ ID NO 167
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 167
atgaacaaac cgcagagctg gaaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg      180
gcgggctttg atcataaagg cctgattgat gcggcgaaag cgcagtatga acgttttccg     240
ggctatcatg cgtttaacgg ccgtatgagc gatcagaccg tgatgctgtc tgaaaaactg     300
gtggaagtga gccgtttga tagcggccgt gtgtttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tggcggcggt gttattccgc cggcgaaagg ctattttcag     720
gcgattctgc cgatcctgcg caaatatgat attccggtga tcagcgatga agtgattgc      780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attaagcga tcgaagaact gccgcatggt      960
tttaccgcgg cggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
```

```
ctggaagcgg tgaaagataa agcgagcaaa gccccgtttg atggcaacct gagcgtgagc    1200
gaacgtattg cgaacacctg caccgatctg ggcctgattt ccgtccgct gggccagagc     1260 gtggttctgt gcccgccgtt tattctgacc gaagcgcaga tggatgaaat gttcgataaa    1320
ctggaaaaag cgctggataa agtgtttgcg gaagtggcgt aa                      1362
```

<210> SEQ ID NO 168
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 168

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Lys Ala Gln Tyr Glu Arg Phe Pro
65                  70                  75                  80

Gly Tyr His Ala Phe Asn Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Leu Pro His Gly
305                 310                 315                 320
```

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 169
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 169
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180 gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcacca ccgcggtgag cgcgagcatg     480
accggcaaac cgtataacag cgtgtttggc ctgccgctgc cgggctttct gcatctgacc     540 tgccccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tggcggcggt gttattccgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgatttac cccggatgcg     840 attattagca gtaaaaacct aaccgcgggt ttttttccgg taggcgcggt gattctgggt     900
ccggaactga gcaaacgtct ggaaaccgcg attgaagcga tcgaagaatt ccgcatggt     960 ctgaccgcgg gcggccatcc ggtgggttgt gcgattgcgc tgaaagcgat tgatgtggtg    1020
atgaacgaag gctggccga aacgtgcgt cgtctggccc gcgtttttga agaacgtctg    1080
aaacatattg cggaacgtcc gaacattggc gaatatcgtg gcattggctt tatgtgggcg    1140
ctggaagcgt tgaaagataa agcgagcaaa gccccgtttg atggcaacct gagcgtgagc    1200
gaacgtattg cgaacacctg caccgatctg ggcctgattt gcgtccgct gggccagagc    1260

```
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 170
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 170

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Thr Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Leu Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

```
Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 171
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 171
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca cgcctgtg aacatggtg       180 gcgggctttg atcataaagg cctgattgat gcggcgaaag cgcagtatga cgttttccg     240 ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg aacgcgtat catggcagca ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgattttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaact gccgcatggt    960
tttaccgcgg cggccatcc ggtgggttgt gcgattgcgc tgaaagcgat tgatgtggtg   1020
atgaacgaag gctggccga aacgtgcgt cgtctggccc cgcgttttga agaacgtctg    1080
aaacatattg cggaacgtcc gaacattggc gaatatcgtg gcattggctt tatgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgtg cggccagagc   1260
gtggttctgt gcccgccgtt tattctgacc gaagcgcaga tggatgaaat gttcgataaa   1320
ctggaaaaag cgctggataa agtgtttgcg gaagtggcgt aa                       1362
```

<210> SEQ ID NO 172
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 172

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Ser Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Leu Pro His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
```

```
              370               375               380
Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Cys Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 173
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 173
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtt taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt tttttttccgg taggcgcggt gattctgggt     900
ccggaactga gcaaacgtct ggaaccgcg attgaagcga tcgaagaatt ttttcatggt     960
tttaccgcgg cggccatcc ggtgggttgt gcgattgcgc tgaaagcgat tgatgtggtg    1020
atgaacgaag cctggccga aacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgag cggccagagc    1260
gtggttctgt gcccgccgtt tattctgacc gaagcgcaga tggatgaaat gttcgataaa    1320
ctggaaaaag cgctggataa agtgtttgcg gaagtggcgt aa                      1362

<210> SEQ ID NO 174
<211> LENGTH: 453
<212> TYPE: PRT
<213> ORGANISM: Artificial Sequence
<220> FEATURE:
```

<223> OTHER INFORMATION: variant of transaminase from V. fluvialis

<400> SEQUENCE: 174

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Phe His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400
```

```
Glu Arg Ile Ala Asn Thr Cys Thr Asp Leu Gly Leu Ile Cys Arg Pro
            405                 410                 415

Ser Gly Gln Ser Val Val Leu Cys Pro Pro Phe Ile Leu Thr Glu Ala
        420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 175
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 175
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg aacatggtg     180
gcgggctttg atcataaagg cctgattgat gcggcgaaag cgcagtatga cgttttccg     240
ggctatcatg cgttttacgg ccgtatgagc gatcagaccg tgatgctgtc tgaaaaactg     300
gtggaagtga gcccgtttga tagcggccgt gtgtttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcacca ccgcggtgag cgcgagcatg     480
accggcaaac cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccggtgggt     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgat tggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 176
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 176

Met Asn Lys Pro Gln Ser Trp Glu Thr Arg Ala Glu Thr Tyr Ser Leu
```

-continued

```
1               5                   10                  15
Tyr Gly Phe Thr Asp Met Pro Ser Leu His Gln Arg Gly Thr Val Val
                20                  25                  30
Val Thr His Gly Glu Gly Pro Tyr Ile Val Asp Val His Gly Arg Arg
                35                  40                  45
Tyr Leu Asp Ala Asn Ser Gly Leu Trp Asn Met Val Ala Gly Phe Asp
                50                  55                  60
His Lys Gly Leu Ile Asp Ala Lys Ala Gln Tyr Glu Arg Phe Pro
65              70                  75                  80
Gly Tyr His Ala Phe Tyr Gly Arg Met Ser Asp Gln Thr Val Met Leu
                85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Met Leu
                115                 120                 125
Trp Phe Leu His Ala Ala Glu Gly Lys Pro Gln Lys Arg Lys Ile Leu
130             135                 140
Thr Arg Trp Asn Ala Tyr His Gly Thr Thr Ala Val Ser Ala Ser Met
145             150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
                195                 200                 205
Ile Gln Lys Glu Gly Ala Asp Thr Ile Ala Gly Phe Phe Ala Glu Pro
210             215                 220
Val Met Gly Ala Gly Gly Val Ile Pro Ala Lys Gly Tyr Phe Gln
225             230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ser Ser Lys Asn Leu Thr
                275                 280                 285
Ala Gly Phe Phe Pro Val Gly Ala Val Ile Leu Gly Pro Glu Leu Ser
                290                 295                 300
Lys Arg Leu Glu Thr Ala Ile Glu Ala Ile Glu Glu Phe Pro Val Gly
305             310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
                340                 345                 350
Ala Pro Arg Phe Glu Glu Arg Leu Lys His Ile Ala Glu Arg Pro Asn
                355                 360                 365
Ile Gly Glu Tyr Arg Gly Ile Gly Phe Met Trp Ala Leu Glu Ala Val
                370                 375                 380
Lys Asp Lys Ala Ser Lys Ala Pro Phe Asp Gly Asn Leu Ser Val Ser
385             390                 395                 400
Glu Arg Ile Ala Asn Thr Cys Thr Asp Leu Gly Leu Ile Cys Arg Pro
                405                 410                 415
Ile Gly Gln Ser Val Val Leu Cys Pro Pro Phe Ile Leu Thr Glu Ala
                420                 425                 430
```

Gln Met Asp Glu Met Phe Asp Lys Leu Glu Lys Ala Leu Asp Lys Val
        435                 440                 445

Phe Ala Glu Val Ala
    450

<210> SEQ ID NO 177
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 177

```
atgaacaaac cgcagagctg gaaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgct gaacatggtg     180
gcgggctttg atcataaagg cctgattgat gcggcgaaag cgcagtatga acgttttccg     240
ggctatcatg cgtttagcgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgcga ccgcggtgag cgcgagcatg     480
accggcaaac gtataacagc gtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaaa ccggtgatgg gtgcggcggt gttattccgc cggcgaaagg ctatttcag     720
gcgattctgc cgatcctgcg caaatatgat attccggtga tcagcgatga agtgatttgc     780
ggctttggcc gtaccggtaa cacctggggc tgcgtgacct atgatttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt tccgcatggt     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg gcctgatttt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 178
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 178

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

```
Val Thr His Gly Glu Gly Pro Tyr Ile Val Asp Val His Gly Arg Arg
         35                  40                  45

Tyr Leu Asp Ala Asn Ser Gly Leu Leu Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Ser Gly Arg Met Ser Asp Gln Thr Val Met Leu
                 85                  90                  95

Ser Glu Lys Leu Val Glu Val Ser Pro Phe Asp Ser Gly Arg Val Phe
             100                 105                 110

Tyr Thr Asn Ser Gly Ser Glu Ala Asn Asp Thr Met Val Lys Met Leu
             115                 120                 125

Trp Phe Leu His Ala Ala Glu Gly Lys Pro Gln Lys Arg Lys Ile Leu
130                 135                 140

Thr Arg Trp Asn Ala Tyr His Gly Ala Thr Ala Val Ser Ala Ser Met
145                 150                 155                 160

Thr Gly Lys Pro Tyr Asn Ser Val Phe Gly Leu Pro Leu Pro Gly Phe
                 165                 170                 175

Leu His Leu Thr Cys Pro His Tyr Trp Arg Tyr Gly Glu Glu Gly Glu
             180                 185                 190

Thr Glu Glu Gln Phe Val Ala Arg Leu Ala Arg Glu Leu Glu Glu Thr
             195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                 245                 250                 255

Glu Val Ile Cys Gly Phe Gly Arg Thr Gly Asn Thr Trp Gly Cys Val
             260                 265                 270

Thr Tyr Asp Phe Thr Pro Asp Ala Ile Ile Ser Ser Lys Asn Leu Thr
             275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                 325                 330                 335

Ile Asp Val Val Met Asn Glu Gly Leu Ala Glu Asn Val Arg Arg Leu
             340                 345                 350

Ala Pro Arg Phe Glu Glu Arg Leu Lys His Ile Ala Glu Arg Pro Asn
             355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                 405                 410                 415

Leu Gly Gln Ser Val Val Leu Cys Pro Pro Phe Ile Leu Thr Glu Ala
             420                 425                 430

Gln Met Asp Glu Met Phe Asp Lys Leu Glu Lys Ala Leu Asp Lys Val
             435                 440                 445

Phe Ala Glu Val Ala
```

<210> SEQ ID NO 179
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 179

```
atgaacaaac cgcagagctg gaaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgct gaacatggtg     180
gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaagc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tgcgggcggt gttattccgc cggcgaaagg ctatttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ttttcatggt     960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg gcctgatttt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 180
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 180

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Leu Asn Met Val Ala Gly Phe Asp
        50                  55                  60

His Lys Gly Leu Ile Asp Ala Lys Ala Gln Tyr Glu Arg Phe Pro
65                  70                  75                  80

Gly Tyr His Ala Phe Gly Arg Met Ser Asp Gln Thr Val Met Leu
            85                  90                  95

Ser Glu Lys Leu Val Glu Val Ser Pro Phe Asp Ser Gly Arg Val Phe
        100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe His Gly
305                 310                 315                 320

Phe Thr Ala Gly Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
450

<210> SEQ ID NO 181
<211> LENGTH: 1362

```
<212> TYPE: DNA
<213> ORGANISM: Artificial Sequence
<220> FEATURE:
<223> OTHER INFORMATION: variant of transaminase from V. fluvialis

<400> SEQUENCE: 181
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcagca ccgcggtgag cgcgagcatg     480
accggcaaac cgtataacag cgtgtttggc ctgccgctgc cgggctttct gcatctgacc     540
tgcccgcatt attggcgtta tgcgaagaa ggcgaaaccg aagaacagtt tgtcgcgcgt     600
ctggcccgtg aactggaaga accattcag aaggaaggcg cggataccat tgcgggcttt     660
tttgcggaac cggtgatggg tggcggcggt gttattccgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggt      960
tttaccgcgg gcggccatcc ggtgggttgt gcgattgcgc tgaaagcgat tgatgtggtg    1020
atgaacgaag gcctggccga aaacgtgcgt cgtctggccc gcgttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacaccctg caccgatctg ggcctgattt gccgtccggt gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362

<210> SEQ ID NO 182
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 182

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
```

```
                    85                  90                  95
Ser Glu Lys Leu Val Glu Val Ser Pro Phe Asp Ser Gly Arg Val Phe
                100                 105                 110
Tyr Thr Asn Ser Gly Ser Glu Ala Asn Asp Thr Met Val Lys Met Leu
            115                 120                 125
Trp Phe Leu His Ala Ala Glu Gly Lys Pro Gln Lys Arg Lys Ile Leu
        130                 135                 140
Thr Arg Trp Asn Ala Tyr His Gly Ser Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Leu His Leu Thr Cys Pro His Tyr Trp Arg Tyr Gly Glu Glu Gly Glu
                180                 185                 190
Thr Glu Glu Gln Phe Val Ala Arg Leu Ala Arg Glu Leu Glu Glu Thr
            195                 200                 205
Ile Gln Lys Glu Gly Ala Asp Thr Ile Ala Gly Phe Phe Ala Glu Pro
        210                 215                 220
Val Met Gly Gly Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
                245                 250                 255
Glu Val Ile Cys Gly Phe Gly Arg Thr Gly Asn Thr Trp Gly Cys Val
                260                 265                 270
Thr Tyr Asp Phe Thr Pro Asp Ala Ile Ile Ser Ser Lys Asn Leu Thr
            275                 280                 285
Ala Gly Phe Phe Pro Val Gly Ala Val Ile Leu Gly Pro Glu Leu Ser
        290                 295                 300
Lys Arg Leu Glu Thr Ala Ile Glu Ala Ile Glu Glu Phe Pro His Gly
305                 310                 315                 320
Phe Thr Ala Gly Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Ala Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Val Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 183
<211> LENGTH: 1362
<212> TYPE: DNA
<213> ORGANISM: Artificial Sequence
<220> FEATURE:
<223> OTHER INFORMATION: variant of transaminase from V. fluvialis
```

<400> SEQUENCE: 183

```
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggcttcct gcatctgacc     540
tgcccgcatt attggcgtta tggcgaagaa ggcgaaaccg aagaacagtt tgtcgcgcgt     600
ctggcccgtg aactgaaga aaccattcag aaggaaggcg cggataccat tgcgggcttt     660
tttgcggaac cggtgatggg tgcgggcggt gttattctgc cggcgaaagg ctattttcag     720
gcgattctgc cgatcctgcg caaatatgat attccggtga tcagcgatga agtgatttgc     780
ggctttggcc gtaccggtaa cacctggggc tgcgtgacct atgattttac cccggatgcg     840
attattagca gtaaaaacct aaccgcgggt ttttttccgg taggcgcggt gattctgggt     900
ccggaactga gcaaacgtct ggaaaccgcg attgaagcga tcgaagaatt ccgcatggtg     960
ctgaccgcgg cggccatcc ggtgggttgt gcgattgcgc tgaaagcgat tgatgtggtg    1020
atgaacgaag gcctggccga aaacgtgcgt cgtctggccc gcgtttttga agaacgtctg    1080
aaacatattg cggaacgtcc gaacattggc gaatatcgtg gcattggctt tatgtgggcg    1140
ctggaagcgg tgaaagataa agcgagcaaa gccccgtttg atggcaacct gagcgtgagc    1200
gaacgtattg cgaacacctg caccgatctg ggcctgattt gccgtccgat tggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 184
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 184

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110
```

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
    195                 200                 205

Ile Gln Lys Glu Gly Ala Asp Thr Ile Ala Gly Phe Phe Ala Glu Pro
210                 215                 220

Val Met Gly Ala Gly Gly Val Ile Leu Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
    275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Leu Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
    355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Ile Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
    435                 440                 445

Phe Ala Glu Val Ala
    450

<210> SEQ ID NO 185
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 185
atgaacaaac cgcagagctg ggaaacgcgt gcggaaacct atagcctgta tggttttacc      60
gatatgccga gcctgcatca gcgtggcacc gtggtggtga cccatggcga aggcccgtat     120

```
atcgtggatg tgcatggccg tcgttatctg gatgcgaaca gcggcctgtg gaacatggtg      180
gcgggctttg atcataaagg cctgattgat gcggcgaaag cgcagtatga acgttttccg      240
ggctatcatg cgttttacgg ccgtatgagc gatcagaccg tgatgctgtc tgaaaaactg      300
gtggaagtga gcccgtttga tagcggccgt gtgtttttata ccaacagcgg cagcgaagcg      360
aacgatacca tggtgaaaat gctgtggttt ctgcatgcgg cggaaggcaa accgcagaaa      420
cgtaaaattc tgacccgttg gaacgcgtat catggcgtga ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaact gcgtcatggt      960
tttaccgcgg gcggccatcc ggtgggttgt gcgattgcgc tgaaagcgat tgatgtggtg     1020
atgaacgaag gcctggccga aaacgtgcgt cgtctggccc gcgtttttga agaacgtctg     1080
aaacatattg cggaacgtcc gaacattggc gaatatcgtg gcattggctt atgtgggcg     1140 ctggaagcgg tgaaagataa agcgagcaaa gccccgtttg atggcaacct gagcgtgagc     1200
gaacgtattg cgaacacctg caccgatctg ggcctgattt gccgtccgac cggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 186
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 186

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

```
Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
            165                 170                 175

Leu His Leu Thr Cys Pro His Tyr Trp Arg Tyr Gly Glu Glu Gly Glu
        180                 185                 190

Thr Glu Glu Gln Phe Val Ala Arg Leu Ala Arg Glu Leu Glu Thr
    195                 200                 205

Ile Gln Lys Glu Gly Ala Asp Thr Ile Ala Gly Phe Phe Ala Glu Pro
210                 215                 220

Val Met Gly Ala Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Leu Arg His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Thr Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 187
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 187

```
atgaacaaac cgcagagctg ggaaacgcgt gcggaaacct atagcctgta tggttttacc    60
gatatgccga gcctgcatca gcgtggcacc gtggtggtga cccatggcga aggcccgtat   120
atcgtggatg tgcatggccg tcgttatctg gatgcgaaca gcggcctgtg gaacatggtg   180
gcgggctttg atcataaagg cctgattgat gcggcgaaag cgcagtatga acgttttccg   240
```

```
ggctatcatg cgtttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
cgtaaaattc tgacccgttg gaacgcgtat catggctgca ccgcggtgag cgcgagcatg    480
accggcaaac cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcggccggt gttattccgc cggcgaaagg ctattttcag    720
gcgattctgc cgatcctgcg caaatatgat attccggtga tcagcgatga agtgatttgc    780
ggctttggcc gtaccggtaa cacctggggc tgcgtgacct atgatttac cccggatgcg    840
attattagca gtaaaaacct aaccgcgggt ttttttccgg taggcgcggt gattctgggt    900
ccggaactga gcaaacgtct ggaaaccgcg attgaagcga tcgaagaata tccgcagggt    960
tttaccgcgg gcggccatcc ggtgggttgt gcgattgcgc tgaaagcgat tgatgtggtg   1020
atgaacgaag gcctggccga aaacgtgcgt cgtctggccc cgcgttttga gaacgtctg   1080
aaacatattg cggaacgtcc gaacattggc gaatatcgtg cattggcttt atgtgggcg   1140
ctggaagcgg tgaaagataa agcgagcaaa gccccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 188
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 188

Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Cys Thr Ala Val Ser Ala Ser Met
145                 150                 155                 160

Thr Gly Lys Pro Tyr Asn Ser Val Phe Gly Leu Pro Leu Pro Gly Phe

```
                    165                 170                 175
Leu His Leu Thr Cys Pro His Tyr Trp Arg Tyr Gly Glu Glu Gly Glu
                180                 185                 190

Thr Glu Glu Gln Phe Val Ala Arg Leu Ala Arg Glu Leu Glu Glu Thr
            195                 200                 205

Ile Gln Lys Glu Gly Ala Asp Thr Ile Ala Gly Phe Phe Ala Glu Pro
        210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
290                 295                 300

Lys Arg Leu Glu Thr Ala Ile Glu Ala Ile Glu Glu Tyr Pro Gln Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 189
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 189
atgaacaaac cgcagagctg ggaaacgcgt gcggaaacct atagcctgta tggttttacc     60
gatatgccga gcctgcatca gcgtggcacc gtggtggtga cccatggcga aggcccgtat    120
atcgtggatg tgcatggccg tcgttatctg gatgcgaaca gcggcctgtg gaacatggtg    180 gcgggcttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatgcgg cggaaggcaa accgcagaaa    420
```

```
cgtaaaattc tgacccgttg gaacgcgtat catggcacca ccgcggtgag cgcgagcatg      480
accggcaaac cgtataacag cgtgtttggc ctgccgctgc cgggctttct gcatctgacc      540
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tggcggcggt gttattccgc cggcgaaagg ctatttcag      720 gcgattctgc cgatcctgcg caaatatgat attccggtga tcagcgatga agtgatttgc      780
ggctttggcc gtaccggtaa cacctggggc tgcgtgacct atgatttac cccggatgcg      840 attattagca gtaaaaacct aaccgcgggt ttttttccgg taggcgcggt gattctgggt      900
ccggaactga gcaaacgtct ggaaaccgcg attgaagcga tcgaagaatt ccgcatggt       960 tttaccgcgg gcggccatcc ggtgggttgt gcgattgcgc tgaaagcgat tgatgtggtg     1020
atgaacgaag gcctggccga aaacgtgcgt cgtctggccc cgcgttttga agaacgtctg     1080
aaacatattg cggaacgtcc gaacattggc gaatatcgtg cattggctt tatgtgggcg     1140 ctggaagcgg tgaaagataa agcgagcaaa gccccgtttg atggcaacct gagcgtgagc     1200
gaacgtattg cgaacacctg caccgatctg ggcctgattt gcgtccggc gggccagagc     1260 gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 190
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 190

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Thr Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

Thr Glu Glu Gln Phe Val Ala Arg Leu Ala Arg Glu Glu Thr
         195                 200                 205

Ile Gln Lys Glu Gly Ala Asp Thr Ile Ala Gly Phe Phe Ala Glu Pro
    210                 215                 220

Val Met Gly Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                    245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
                275                 280                 285

Ala Gly Phe Phe Pro Val Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Gly Gly His Pro Val Gly Cys Ala Ile Ala Leu Lys Ala
                    325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Ala Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 191
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 191
atgaacaaac cgcagagctg ggaaacgcgt gcggaaacct atagcctgta tggttttacc      60
gatatgccga gcctgcatca gcgtggcacc gtggtggtga cccatggcga aggcccgtat     120
atcgtggatg tgcatggccg tcgttatctg gatgcgaaca gcggcctgtt taacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgtttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttct gcatctgacc     540

```
tgcccgcatt attggcgtta tggcgaagaa ggcgaaaccg aagaacagtt tgtcgcgcgt      600
ctggcccgtg aactggaaga aaccattcag aaggaaggcg cggataccat tgcgggcttt      660
tttgcggaac cggtgatggg tgcgggcggt gttattccgc cggcgaaagg ctattttcag      720
gcgattctgc cgatcctgcg caaatatgat attccggtga tcagcgatga agtgatttgc      780
ggctttggcc gtaccggtaa cacctggggc tgcgtgacct atgattttac cccggatgcg      840
attattagca gtaaaaacct aaccgcgggt ttttttccgg taggcgcggt gattctgggt      900
ccggaactga gcaaacgtct ggaaaccgcg attgaagcga tcgaagaatt tggccatggt      960
tttaccgcgg cggccatcc ggtgggttgt gcgattgcgc tgaaagcgat tgatgtggtg     1020
atgaacgaag gcctggccga aaacgtgcgt cgtctggccc gcgttttga agaacgtctg     1080 aaacatattg cggaacgtcc gaacattggc gaatatcgtg cattggcctt tatgtgggcg     1140
ctggaagcgg tgaaagataa agcgagcaaa gccccgtttg atggcaacct gagcgtgagc     1200
gaacgtattg cgaacacctg caccgatctg ggcctgattt gccgtccgat tggccagagc     1260
gtggttctgt gcccgccgtt tattctgacc gaagcgcaga tggatgaaat gttcgataaa     1320
ctggaaaaag cgctggataa agtgtttgcg gaagtggcgt aa                        1362
```

<210> SEQ ID NO 192
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 192

```
Met Asn Lys Pro Gln Ser Trp Glu Thr Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

```
Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
            245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Val Gly Ala Val Ile Leu Gly Pro Glu Leu Ser
            290                 295                 300

Lys Arg Leu Glu Thr Ala Ile Glu Ala Ile Glu Phe Gly His Gly
305                 310                 315                 320

Phe Thr Ala Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
            370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Ile Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
    450

<210> SEQ ID NO 193
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 193
atgaacaaac cgcagagctg ggaagcgcgt gcgaaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg gaacatggtg     180
gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtta gcccgtttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttgt gcatctgacc     540
tgcccgcatt attggcgtta tggcgaagaa ggcgaaaccg aagaacagtt tgtggcgcgt     600
ctggcccgtg aactgaaga aaccattcag cgtgaaggcg cggataccat tgcgggcttt     660
tttgcggaac cggtgatggg tgcgggcggt gttattccgc cggcgaaagg ctattttcag     720
```

```
gcgattctgc cgatcctgcg caaatatgat attccggtga tcagcgatga agtgatttgc    780
ggctttggcc gtaccggcaa cacctggggc tgcgtgacct atgattttac cccggatgcg    840
attattagca gcaaaaacct gaccgcgggt ttttttccga tgggcgcggt gattctgggt    900
ccgaaactga gcaaacgtct ggaaaccgcg attgaagcga tcgaagaatt ccgcatggt     960
tttaccgcga gcggccatcc ggtgggttgt gcgattgcgc tgaaagcgat tgatgtggtg   1020
atgaacgaag gcctggccga aaacgtgcgt cgtctggccc gcgtttttga agaacgtctg   1080
aaacatattg cggaacgtcc gaacattggc gaatatcgtg gcattggctt tatgtgggcg   1140
ctggaagcgg tgaaagataa agcgagcaaa accccgtttg atggcaacct gagcgtgagc   1200
gaacgtattg cgaacacctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                     1362
```

<210> SEQ ID NO 194
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 194

```
Met Asn Lys Pro Gln Ser Trp Glu Ala Arg Ala Lys Thr Tyr Ser Leu
1               5                   10                  15
Tyr Gly Phe Thr Asp Met Pro Ser Leu His Gln Arg Gly Thr Val Val
            20                  25                  30
Val Thr His Gly Glu Gly Pro Tyr Ile Val Asp Val Asn Gly Arg Arg
        35                  40                  45
Tyr Leu Asp Ala Asn Ser Gly Leu Trp Asn Met Val Ala Gly Phe Asp
    50                  55                  60
His Lys Gly Leu Ile Asp Ala Ala Lys Ala Gln Tyr Glu Arg Phe Pro
65                  70                  75                  80
Gly Tyr His Ala Phe Phe Gly Arg Met Ser Asp Gln Thr Val Met Leu
                85                  90                  95
Ser Glu Lys Leu Val Glu Val Ser Pro Phe Asp Ser Gly Arg Val Phe
            100                 105                 110
Tyr Thr Asn Ser Gly Ser Glu Ala Asn Asp Thr Met Val Lys Met Leu
        115                 120                 125
Trp Phe Leu His Ala Ala Glu Gly Lys Pro Gln Lys Arg Lys Ile Leu
    130                 135                 140
Thr Arg Trp Asn Ala Tyr His Gly Val Thr Ala Val Ser Ala Ser Met
145                 150                 155                 160
Thr Gly Lys Pro Tyr Asn Ser Val Phe Gly Leu Pro Leu Pro Gly Phe
                165                 170                 175
Val His Leu Thr Cys Pro His Tyr Trp Arg Tyr Gly Glu Glu Gly Glu
            180                 185                 190
Thr Glu Glu Gln Phe Val Ala Arg Leu Ala Arg Glu Leu Glu Glu Thr
        195                 200                 205
Ile Gln Arg Glu Gly Ala Asp Thr Ile Ala Gly Phe Phe Ala Glu Pro
    210                 215                 220
Val Met Gly Ala Gly Gly Val Ile Pro Pro Ala Lys Gly Tyr Phe Gln
225                 230                 235                 240
Ala Ile Leu Pro Ile Leu Arg Lys Tyr Asp Ile Pro Val Ile Ser Asp
```

```
                    245                 250                 255
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Lys Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 195
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 195
atgaacaaac cgcagaggtg ggaagcgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg aacatggtg     180 gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatacgg cggaaggcaa accgcagaaa     420
cgtaaaattc tgacccgttg gaacgcgtat catggcgtga ccgcggtgag cgcgagcatg     480
accggcaaac cgtataacag cgtgtttggc ctgccgctgc cgggctttgt gcatctgacc     540
tgcccgcatt tttggcgtta cggcgaagaa ggcgaaaccg aagaacagtt tgtggcgcgt     600
ctggcccgtg aactggaaga aaccattcag cgtgaaggcg cggataccat tgcgggcttt     660
tttgcggaac cggtgatggg tgcgggcggt gttattccgc cggcgaaagg ctattttcag     720
gcgattctgc cgatcctgcg caaatatgat attcaggtga tcagcgatga agtgattttgc     780 ggctttggcc gtaccggcaa cacctggggc tgcgtgacct atgattttac cccggatgcg     840
```

```
attattagca gcaaaaacct gaccgcgggt ttttttccga tgggcgcggt gattctgggt    900
ccggaactga gcaaacgtct ggaaaccgcg attgaagcgt tcgaagaatt tccgcatggt    960
tttaccgcga gcggccatcc ggtgggttgt gcgattgcgc tgaaagcgat tgatgtggtg   1020
atgaacgaag gcctggccga aaacgtgcgt cgtctggccc gcgttttga agaacgtctg   1080 aaacatattg cggaacgtcc gaacattggc gaatatcgtg gcattggctt tatgtgggcg   1140
ctggaagcgg tgaaagataa agcgagcaaa accccgtttg atggcaacct gagcgtgagc   1200
gaacgtattg cgaacaccctg caccgatctg ggcctgattt gccgtccgct gggccagagc   1260
gtggttctgt gcccgccgtt tattctgacc gaagcgcaga tggatgaaat gttcgataaa   1320
ctggaaaaag cgctggataa agtgtttgcg gaagtggcgt aa                      1362
```

<210> SEQ ID NO 196
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 196

```
Met Asn Lys Pro Gln Arg Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Thr Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Phe Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Gln Val Ile Ser Asp
                245                 250                 255

Glu Val Ile Cys Gly Phe Gly Arg Thr Gly Asn Thr Trp Gly Cys Val
            260                 265                 270
```

Thr Tyr Asp Phe Thr Pro Asp Ala Ile Ile Ser Ser Lys Asn Leu Thr
            275                 280                 285

Ala Gly Phe Phe Pro Met Gly Ala Val Ile Leu Gly Pro Glu Leu Ser
290                 295                 300

Lys Arg Leu Glu Thr Ala Ile Glu Ala Phe Glu Glu Phe Pro His Gly
305                 310                 315                 320

Phe Thr Ala Ser Gly His Pro Val Gly Cys Ala Ile Ala Leu Lys Ala
            325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
    435                 440                 445

Phe Ala Glu Val Ala
    450

```
<210> SEQ ID NO 197
<211> LENGTH: 1362
<212> TYPE: DNA
<213> ORGANISM: Artificial Sequence
<220> FEATURE:
<223> OTHER INFORMATION: variant of transaminase from V. fluvialis

<400> SEQUENCE: 197
atgaacaaac cgcagatctg ggaagcgcgt gcggaaacct atagcctgta tggctttacc      60
gatatgccga gcctgcatca gcgtggcacc gtggtggtga cccatggcga aggcccgtat     120
atcgtggatg tgaacggccg tcgttatctg gatgcgaaca gcggcctgtg aacatggtg     180 gcgggctttg atcataaagg cctgattgat gcggcgaaag cgcagtatga acgttttccg     240
ggctatcatg cgttttttgg ccgtatgagc gatcagaccg tgatgctgtc tgaaaaactg     300
gtggaagtga gccgttttga tagcggccgt gtgttttata ccaacagcgg cagcgaagcg     360
aacgatacca tggtgaaaat gctgtggttt ctgcatgcgg cggaaggcaa accgcagaaa     420
cgtaaaattc tgacccgttg gaacgcgtat catggcgtga ccgcggtgag cgcgagcatg     480
accggcaaac gtataacag cgtgtttggc ctgccgctgc cgggctttgt gcatctgacc     540
tgcccgcatt attggcgtta tggcgaagaa ggcgaaaccg aagaacagtt tgtggcgcgt     600
ctggcccgtg aactgaaaga aaccattcag cgtgaaggcg cggataccat tgcgggcttt     660
tttgcggaac cggtgatggg tgcgggcggt gttattccgc cggcgaaagg ctattttcag     720
gcgattctgc cgatcctgcg caaatatgat attccggtga tcagcgatga agtgatttgc     780
ggctttggcc gtaccggcaa cacctggggc tgcgtgacct atgattttac cccggatgcg     840
attattagca gcaaaaacct gaccgcgggt ttttttccga tgggcgcggt gattctgggt     900
ccggaactga gcaaacgtct ggaaaccgcg attgaagcga tcgaagaatt ccgcatggt     960 tttaccgcga gcggccatcc ggtgggttgt gcgattgcgc tgaaagcgat tgatgtggtg    1020
```

```
atgaacgaag gcctggccga aaacgtgcgt cgtctggccc cgcgttttga agaacgtctg    1080
aaacatattg cggaacgtcc gaacattggc gaatatcgtg gcattggctt tatgtgggcg    1140
ctggaagcgg tgaaagataa agcgagcaaa accccgtttg atggcaacct gagcgtgagc    1200
gaacgtattg cgaacacctg caccgatctg ggcctgattt gccgtccgct gggccagagc    1260
gtggttctgt gcccgccgtt tattctgacc gaagcgcaga tggatgaaat gttcgataaa    1320
ctggaaaaag cgctggataa agtgtttgcg gaagtggcgt aa                       1362
```

<210> SEQ ID NO 198
<211> LENGTH: 453
<212> TYPE: PRT
<213> ORGANISM: Artificial Sequence
<220> FEATURE:
<223> OTHER INFORMATION: variant of transaminase from V. fluvialis

<400> SEQUENCE: 198

```
Met Asn Lys Pro Gln Ile Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300
```

```
Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
    450
```